United States Patent
Heinrich et al.

(10) Patent No.: US 9,249,140 B2
(45) Date of Patent: Feb. 2, 2016

(54) BICYCLIC HETEROAROMATIC COMPOUNDS

(75) Inventors: Timo Heinrich, Gross-Umstadt (DE); Felix Rohdich, Worfelden (DE); Christina Esdar, Mainz (DE); Mireille Krier, Darmstadt (DE); Hartmut Greiner, Weiterstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 14/240,584

(22) PCT Filed: Jul. 26, 2012

(86) PCT No.: PCT/EP2012/003171
§ 371 (c)(1),
(2), (4) Date: Feb. 24, 2014

(87) PCT Pub. No.: WO2013/026516
PCT Pub. Date: Feb. 28, 2013

(65) Prior Publication Data
US 2015/0218155 A1    Aug. 6, 2015

(30) Foreign Application Priority Data
Aug. 23, 2011   (DE) .................. 10 2011 111 400

(51) Int. Cl.
| A61K 31/535 | (2006.01) |
| C07D 471/02 | (2006.01) |
| C07D 471/04 | (2006.01) |
| C07D 487/04 | (2006.01) |
| C07D 473/34 | (2006.01) |

(52) U.S. Cl.
CPC ............ *C07D 471/04* (2013.01); *C07D 473/34* (2013.01); *C07D 487/04* (2013.01)

(58) Field of Classification Search
None
See application file for complete search history.

(56) References Cited

U.S. PATENT DOCUMENTS

| 5,411,929 | A  | 5/1995  | Ford et al.     |
| 6,187,777 | B1 | 2/2001  | Norman et al.   |
| 6,583,154 | B1 | 6/2003  | Norman et al.   |
| 6,770,643 | B2 | 8/2004  | Cox et al.      |
| 6,897,207 | B2 | 5/2005  | Cox et al.      |
| 7,227,020 | B2 | 6/2007  | Cox et al.      |
| 7,943,616 | B2 | 5/2011  | Cox et al.      |
| 8,592,581 | B2 | 11/2013 | Sheldrake et al.|
| 2004/0009983 | A1 | 1/2004 | Cox et al.   |
| 2004/0053931 | A1 | 3/2004 | Cox et al.   |
| 2004/0198737 | A1 | 10/2004 | Cox et al.  |
| 2005/0267304 | A1 | 12/2005 | Cox et al.  |
| 2008/0176892 | A1 | 7/2008 | Heinrich et al. |
| 2010/0093769 | A1 | 4/2010 | Sheldrake et al. |
| 2011/0282056 | A1 | 11/2011 | Askew et al. |

FOREIGN PATENT DOCUMENTS

| WO | 9940091 A1     | 8/1999  |
| WO | 0147922 A2     | 7/2001  |
| WO | 03000688 A1    | 1/2003  |
| WO | 2006114180 A1  | 11/2006 |
| WO | 2008122767 A2  | 10/2008 |
| WO | 2009094123 A1  | 7/2009  |
| WO | 2011149827 A1  | 12/2011 |

OTHER PUBLICATIONS

Panchal, T. et al., Bioorg. Med. Chem. Lett. (2009), 19(23), 6813-6817.*
Kim, J. et al., J. Amer. Chem. Soc. (2006),128(48), 15372-15373.*
International Search Report for PCT/EP2012/003171 dated Sep. 17, 2012.
Bullock, M. W. et al., "Syntheses of 6-Substituted Purines," Journal of the American Chemical Society, Aug. 5, 1956, vol. 78, No. 15, pp. 3693-3696.
Moravcova, D. et al., "Pyrazolo,3-d]pyrimidines as New Generation of Cyclin-Dependent Kinase Inhibitors," Bioorganic & Medcinal Chemistry Letters, 2003, vol. 13, pp. 2989-2992.
Henderson, J. L. et al., "Palladium-Catalyzed Amination of Unprotected Halo-7-azaindoles," Organic Letters, 2010, vol. 12, No. 20, pp. 4438-4441.
Sorum, C. et al., "1H, 13C and 19F NMR data of N-substituted 6-(4-methoxyphenyl)-7H-pyrrolo[2,3-d]pyrimidin-4-amines in DMSO-d6," Magn. Reson. Chem., 2010, vol. 48, pp. 244-248.
Medina, J. R. et al., "Discovery of a new series of Aurora inhibitors through truncation of GSK1070916," Bioorganic & Medicinal Chemistry Letters, 2010, vol. 20, pp. 2552-2555.
Wang, T. et al., "A novel chemotype of kinase inhibitors: Discovery of 3,4-ring fused 7-azaindoels and deazapurines as potent JAK2 inhibitors," Bioorganic & Medicinal Chemistry Letters, 2010, vol. 20, pp. 153-156.
Baizer, M. M. et al., "A New Synthesis of Kinetin and Its Analogs," Nov. 1956, pp. 1276-1277.
Carbon, J. A. et al., "The preparation of Several 4-substituted Imidazo [4,5-d] pyridazines as possible purine antimetabolites," Journal of the American Chemical Society, Nov. 20, 1958, vol. 80, No. 22, pp. 6083-6088.
Novotna, R. et al., "X-ray crystallographic and NMR study of the tautomerism in kinetin, kinetin riboside and their derivatives: A comparison between the solid state and solution," Journal of Molecular Structure, 2010, vol. 963, pp. 202-210.
Panchal, T. et al., "Evaluation of basic, heterocyclic ring systems as templates for use as potassium competitive acid blockers (pCABs)," Bioorganic & Medicinal Chemistry Letters, 2009, vol. 19, pp. 6813-6817.

(Continued)

*Primary Examiner* — Heidi Reese
(74) *Attorney, Agent, or Firm* — Millen White Zelano and Branigan, PC; John Sopp; Anthony Zelano

(57) ABSTRACT

Compounds of the formula I, in which X1, X2, X3, X4, X5, R1, R2, R3, R4, R5 and R6 have the meanings indicated in Claim 1, are kinase inhibitors and can be employed, inter alia, for the treatment of tumors.

3 Claims, No Drawings

(56) References Cited

OTHER PUBLICATIONS

Nisler, J. et al., "Cytokinin receptor antagonists derived from 6-benzylaminopurine," Phytochemistry, 2010, vol. 71, pp. 823-830.
Daly, J. W. et al., "Purines. IV. The preparation of Certain 6-substituted-and 6,9-disubstituted purines," Journal of Organic Chemistry, Feb. 1, 1956, vol. 21, No. 2, pp. 177-179.
Norman, M. H. et al., "Structure—Activity Relationships of a Series of Pyrrolo[3,2-d]pyrimidine Derivatives and Related Compounds as Neuropeptide Y5 Receptor Antagonists," J. Med. Chem., 2000, vol. 43, pp. 4288-4312.
Zatloukal, M. et al., "Novel potent inhibitors of A. thaliana cytokinin oxidase/dehydrogenase," Bioorganic & Medicinal Chemistry, 2008, vol. 16, pp. 9268-9275.

* cited by examiner

SEQUENCE LISTING

```
<160> NUMBER OF SEQ ID NOS: 4

<210> SEQ ID NO 1
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Biotin-Beta-Ala
```

```
<220> FEATURE:
<221> NAME/KEY: MOD_RES
<222> LOCATION: (2)..(2)
<223> OTHER INFORMATION: Beta-Ala

<400> SEQUENCE: 1

Ala Ala Lys Thr Phe Cys Gly Thr Pro Glu Tyr Leu Ala Pro Glu Val
1               5                   10                  15

Arg Arg Glu Pro Arg Ile Leu Ser Glu Glu Gln Glu Met Phe Arg
            20                  25                  30

Asp Phe Asp Tyr Ile Ala Asp Trp Cys
            35                  40

<210> SEQ ID NO 2
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Biotin-C6-C6-Gly

<400> SEQUENCE: 2

Gly Leu Lys Lys Glu Arg Leu Leu Asp Asp Arg His Asp Ser Gly Leu
1               5                   10                  15

Asp Ser Met Lys Asp Glu Glu
            20

<210> SEQ ID NO 3
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Biotin-amino hexanoic acid
<220> FEATURE:
<221> NAME/KEY: MOD_RES
<222> LOCATION: (2)..(2)
<223> OTHER INFORMATION: Amino hexanoic acid

<400> SEQUENCE: 3

Xaa Xaa Ala Lys Pro Lys Gly Asn Lys Asp Tyr His Leu Gln Thr Cys
1               5                   10                  15

Cys Gly Ser Leu Ala Tyr Arg Arg Arg
            20                  25

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 4

His His His His His His
1               5
```

BICYCLIC HETEROAROMATIC COMPOUNDS

SEQUENCE LISTING

The instant application contains a Sequence Listing which has been submitted electronically in ASCII format and is hereby incorporated by reference in its entirety. Said ASCII copy, created on Oct. 29, 2014, is named MERCK-4175_SL.txt and is 2,144 bytes in size.

BACKGROUND OF THE INVENTION

The invention had the object of finding novel compounds having valuable properties, in particular those which can be used for the preparation of medicaments.

The present invention relates to compounds in which the inhibition, regulation and/or modulation of signal transduction by kinases, in particular tyrosine kinases, plays a role, furthermore to pharmaceutical compositions which comprise these compounds, and to the use of the compounds for the treatment of tyrosine kinase-induced diseases.

Specifically, the present invention relates to compounds which inhibit, regulate and/or modulate tyrosine kinase signal transduction, to compositions which comprise these compounds, and to methods for the use thereof for the treatment of tyrosine kinase-induced diseases and conditions, such as cancer, tumour growth, arteriosclerosis, age-related macular degeneration, diabetic retinopathy, inflammatory diseases and the like, in mammals.

Tyrosine kinases are a class of enzymes which catalyse the transfer of the terminal phosphate of adenosine triphosphate to tyrosine residues in protein substrates. It is thought that tyrosine kinases, through substrate phosphorylation, play a crucial role in signal transduction for a number of cellular functions. Although the precise mechanisms of signal transduction are still unclear, tyrosine kinases have been shown to be important contributing factors in cell proliferation, carcinogenesis and cell differentiation.

Tyrosine kinases can be categorised as receptor-type tyrosine kinases or non-receptor-type tyrosine kinases. Receptor-type tyrosine kinases have an extracellular portion, a transmembrane portion and an intracellular portion, while non-receptor-type tyrosine kinases are exclusively intracellular. Non-receptor-type tyrosine kinases consist of a multiplicity of subfamilies, including Src, Frk, Btk, Csk, Abl, Zap70, Fes/Fps, Fak, Jak, Ack and LIMK. Each of these subfamilies is further sub-divided into different receptors. For a more detailed discussion of non-receptor-type tyrosine kinases, see the paper by Bolen *Oncogene*, 8:2025-2031 (1993), which is hereby incorporated by way of reference.

Both receptor-type tyrosine kinases and non-receptor-type tyrosine kinases are involved in cellular signalling pathways leading to numerous pathogenic conditions, including cancer, psoriasis and hyperimmune responses.

The present invention relates to the compounds as inhibitors of FAK (focal adhesion kinase).

FAK (encoded by the PTK2 gene) is a non-receptor tyrosine kinase which integrates signals from integrins and growth factor receptors. FAK has been reported to play a role in the regulation of cell survival, growth, spread, migration and invasion (McLean et al 2005, Nat Rev Cancer 5:505-515). Furthermore, FAK is regulated and activated by phosphorylation on multiple tyrosine residues. Overexpression of FAK mRNA and/or protein has been documented in many human tumours, including cancers of the breast, colon, thyroid, and prostate (Owens et al. 1995, Cancer Research 55: 2752-2755; Agochiya et al. 1999, Oncogene 18: 5646-5653; Gabarro-Niecko et al. 2003, Cancer Metastasis Rev. 22:359-374). More importantly, there is evidence that phosphorylated FAK is increased in malignant tissues compared with normal tissues (Grisaru-Granovsky et al. 2005, Int. J. Cancer 113: 372-378).

Inhibition of FAK by RNAi or expression of a dominant-negative FAK has been shown to induce loss of adhesion and cell death in human breast and melanoma cell lines and to increase docetaxel-mediated apoptosis in ovarian cancer cells (Beviglia et al 2003, Biochem J. 373:201-210, Smith et al 2005, Melanoma Res. 15:357-362, Haider et al 2005, Clin. Cancer Res. 11:8829-8836). However, inhibition of FAK in normal human fibroblasts or immortalized mammalian cells (MCFIOA) was found not to cause loss of attachment or apoptosis (Xu et al. 1996 Cell Growth and Diff 7:413-418). Inhibition of FAK by dominant-negative expression has also been shown to reduce tumour growth and eliminate lung metastasis of mammalian adenocarcinoma cells in a syngenetic rat model (van Nimwegen et al 2005, Cancer Res. 65:4698-4706). Likewise, inhibition of FAK by shRNA inhibited lung metastasis and reduced lethality by 40% in a syngenetic mouse model (Mitra et al 2006, Oncogene 25: 4429-4440). In this study, transient re-expression of wild-type, but not kinase-inactive FAK resulted in re-mutation of the shRNA phenotypes. Inhibition of FAK by dominant-negative expression in mouse 4TI carcinoma cells reduced tumour growth and angiogenesis in mice (Mitra et al 2006, Oncogene 25:5969-5984).

In addition, loss of FAK catalytic activity (reconstitution of FAK−/− cells with kinase-inactive FAK) reduced growth of v-Src tumours in mice and decreased angiogenesis.

Thus, there is strong evidence to suggest that inhibition of FAK activity induces apoptosis, loss of adhesion, inhibition of cell growth and migration and that such inhibition reduces angiogenesis. Accordingly, compounds which inhibit FAK activity would be useful for the treatment of cancer.

The compounds according to the invention also exhibit a certain action in the inhibition of the serine/threonine kinases PDK1, IKKε and TBK1.

PDK1 phosphorylates and activates a sub-group of the AGC protein kinase family, comprising PKB, SGK, S6K and PKC isoforms. These kinases are involved in the PI3K signal transduction pathway and control basic cellular functions, such as survival, growth and differentiation. PDK1 is thus an important regulator of diverse metabolic, proliferative and life-sustaining effects.

IKKε and TBK1 are serine/threonine kinases which are highly homologous to one another and to other IkB kinases. The two kinases play an integral role in the innate immune system. Double-stranded RNA viruses are recognised by the Toll-like receptors 3 and 4 and the RNA helicases RIG-I and MDA-5 and result in activation of the TRIF-TBK1/IKKε-IRF3 signalling cascade, which results in a type I interferon response.

In 2007, Boehm et al. described IKKε as a novel breast cancer oncogene [J. S. Boehm et al., Cell 129, 1065-1079, 2007]. 354 kinases were investigated with respect to their ability to recapitulate the Ras-transforming phenotype together with an activated form of the MAPK kinase Mek. IKKε was identified here as a cooperative oncogene.

In addition, the authors were able to show that IKBKE is amplified and overexpressed in numerous breast cancer cell lines and tumour samples. The reduction in gene expression by means of RNA interference in breast cancer cells induces apoptosis and impairs the proliferation thereof. Eddy et al. obtained similar findings in 2005, which underlines the importance of IKKε in breast cancer diseases [S. F. Eddy et al., Cancer Res. 2005; 65 (24), 11375-11383].

A protumorigenic effect of TBK1 was reported for the first time in 2006. In a screening of a gene library comprising 251,000 cDNA, Korherr et al. identified precisely three genes, TRIF, TBK1 and IRF3, which are typically involved in the innate immune defense as proangiogenic factors [C. Korherr et al., PNAS, 103, 4240-4245, 2006]. In 2006, Chien et al. [Y. Chien et al., Cell 127, 157-170, 2006] published that TBK1−/− cells can only be transformed to a limited extent using oncogenic Ras, which suggests an involvement of TBK1 in the Ras-mediated transformation. Furthermore, they were able to show that an RNAi-mediated knockdown of TBK1 triggers apoptosis in MCF-7 and Panc-1 cells. Barbie et al. recently published that TBK1 is of essential importance in numerous cancer cell lines with mutated K-Ras, which suggests that TBK1 intervention could be of therapeutic importance in corresponding tumours [D. A. Barbie et al., Nature Letters 1-5, 2009].

The identification of small compounds which specifically inhibit, regulate and/or modulate FAK signal transduction is therefore desirable and an aim of the present invention.

It has been found that the compounds of the formula I and salts thereof have very valuable pharmacological properties while being well tolerated.

The present invention furthermore relates to the use of one or more compounds according to the invention in the treatment and/or prophylaxis of diseases, preferably the diseases described herein, that are caused, mediated and/or propagated by Raf kinases and in particular diseases that are caused, mediated and/or propagated by FAK.

The diseases discussed herein are usually divided into two groups, hyperproliferative and non-hyperproliferative diseases. In this connection, psoriasis, arthritis, inflammation, endometriosis, scarring, benign prostatic hyperplasia, immunological diseases, autoimmune diseases and immunodeficiency diseases are to be regarded as non-cancerous diseases, of which arthritis, inflammation, immunological diseases, autoimmune diseases and immunodeficiency diseases are usually regarded as non-hyperproliferative diseases. In this connection, brain cancer, lung cancer, squamous cell cancer, bladder cancer, gastric cancer, pancreatic cancer, hepatic cancer, renal cancer, colorectal cancer, breast cancer, head cancer, neck cancer, oesophageal cancer, gynecological cancer, thyroid cancer, lymphoma, chronic leukaemia and acute leukaemia are to be regarded as cancerous diseases, all of which are usually regarded as hyperproliferative diseases. In particular, cancerous cell growth is a disease which is a target of the present invention. The present invention therefore relates to compounds according to the invention as medicaments and/or medicament active compounds in the treatment and/or prophylaxis of the said diseases and to the use of compounds according to the invention for the preparation of a pharmaceutical for the treatment and/or prophylaxis of the said diseases as well as to a method for the treatment of the said diseases which comprises the administration of one or more compounds according to the invention to a patient in need of such an administration.

It can be shown that the compounds according to the invention have an antiproliferative action in vivo. The compounds according to the invention are administered to a patient having a hyperproliferative disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treatment" is used to refer to both prevention of diseases and treatment of pre-existing conditions. The prevention of proliferation is achieved by administration of the compounds according to the invention prior to the development of overt disease, for example to prevent the growth of tumours, prevent metastatic growth, diminish restenosis associated with cardiovascular surgery, etc. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow the active agents to induce cell death or to inhibit migration, usually between about one hour and one week. In vitro testing can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For the identification of kinase inhibitors, various assay systems are available. In scintillation proximity assay (Sorg et al., J. of. Biomolecular Screening, 2002, 7, 11-19) and flash-plate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody (Ross et al., 2002, Biochem. J., 366: 977-981).

There are many diseases associated with deregulation of cellular proliferation and cell death (apoptosis). The conditions of interest include, but are not limited to, the following. The compounds according to the invention are suitable for the treatment of a number of conditions where there is proliferation and/or migration of smooth muscle cells and/or inflammatory cells into the intimal layer of a vessel, resulting in restricted blood flow through that vessel, for example in the case of neointimal occlusive lesions. Occlusive vascular diseases of interest include atherosclerosis, graft coronary vascular disease after transplantation, vein graft stenosis, peri-anastomatic prosthetic restenosis, restenosis after angioplasty or stent placement, and the like.

PRIOR ART

Other bicyclic heterocycles are described in WO 2003/035065 and in WO 2006/114180.

Pyridine derivatives are described as FAK inhibitors in WO 2009/105498 and in WO 2008/115369.

Other pyrimidine derivatives for combating cancer are described in WO 2004/056807 and in WO 2010/055117.

SUMMARY OF THE INVENTION

The invention relates to compounds of the formula I

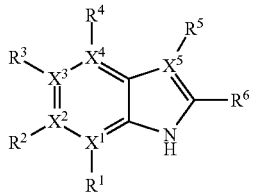

I in which
$X^1$ denotes C or N,
$X^2$ denotes C or N,
$X^3$ denotes C or N,
$X^4$ denotes C or N,
$X^5$ denotes C or N,
$R^1$ is absent if $X^1$=N
or
denotes NH(CH$_2$)$_n$Het or NH(CH$_2$)$_n$Ar,
$R^2$ is absent if $X^2$=N
or
denotes H or Het$^1$,
$R^3$ is absent if $X^3$=N,
or
denotes H, N, A, Hal, Cyc, OH or OA,
$R^4$ is absent if $X^4$=N
or
denotes H, NH(CH$_2$)$_n$Het$^1$, Het$^1$, O(CH$_2$)$_n$Het$^1$, NH(CH$_2$)$_n$Ar$^1$, ═══Ar$^1$, (CH$_2$)$_n$Ar$^1$ or NH-Cyc,
$R^5$ is absent if $X^5$=N
or
denotes H or Hal,
$R^6$ denotes H, Ar$^2$, A, Het$^2$, COHet$^3$, CONH$_2$, CONHA, CONA$_2$ or Cyc,
$R^7$ denotes H or alkyl having 1, 2, 3 or 4 C atoms,
Het denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, quinolinyl, quinoxalinyl, quinazolinyl, pyrrolopyridinyl, purinyl, indolyl, dihydroindolyl, indazolyl, tetrahydroquinolyl, dihydrobenzoxazolyl, dihydropyridyl, dihydropyridazinyl, dihydrobenzimidazolyl, dihydrobenzothiazolyl, piperidinyl, pyrrolidinyl, morpholinyl, piperazinyl, imidazolidinyl, oxazolidinyl or tetrahydropyranyl, each of which is unsubstituted or mono-, di- or trisubstituted by A and/or ═O,
Ar denotes phenyl which is unsubstituted or mono-, di-, tri-, tetra or pentasubstituted by Hal, A, (CH$_2$)$_n$OH, (CH$_2$)$_n$OA, (CH$_2$)$_n$CN, NO$_2$, SO$_2$A, COOH, COOA, NH$_2$, NHA, NA$_2$, CHO, COA, (CH$_2$)$_n$CONH$_2$, (CH$_2$)$_n$CONHA, (CH$_2$)$_n$CONA$_2$, Het$^3$, NHCOHet$^3$, SO$_2$NH$_2$, SO$_2$NHA and/or NHCOA, Het$^1$ denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, quinolinyl, quinoxalinyl, quinazolinyl, pyrrolopyridinyl, purinyl, indolyl, dihydroindolyl, indazolyl, tetrahydroquinolyl, dihydrobenzoxazolyl, dihydropyridyl, dihydropyridazinyl, dihydrobenzimidazolyl, dihydrobenzothiazolyl, piperidinyl, pyrrolidinyl, morpholinyl, piperazinyl, imidazolidinyl, oxazolidinyl or tetrahydropyranyl, each of which is unsubstituted or mono-, di- or trisubstituted by A, OH, NR$^7$SO$_2$A and/or ═O, Ar$^1$ denotes phenyl which is unsubstituted or mono-, di-, tri-, tetra or pentasubstituted by Hal, A, (CH$_2$)$_n$OH, (CH$_2$)$_n$OA, (CH$_2$)$_n$CN, NO$_2$, SO$_2$A, COOH, COOA, NH$_2$, NHA, NA$_2$, CHO, COA, (CH$_2$)$_n$CONR$^7$, Het$^3$, NHCOHet$^3$, NR$^7$SO$_2$A and/or NHCOA, Het$^2$ denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, quinolinyl, quinoxalinyl, quinazolinyl, pyrrolopyridinyl, purinyl, indolyl, indolinyl, dihydroindolyl, indazolyl, tetrahydroquinolyl, dihydrobenzoxazolyl, dihydropyridyl, dihydropyridazinyl, dihydrobenzimidazolyl, dihydrobenzothiazolyl, piperidinyl, pyrrolidinyl, morpholinyl, piperazinyl, imidazolidinyl, 6,7-dihydro-5H-cyclopenta[b]pyridinyl, oxazolidinyl or tetrahydropyranyl, each of which is unsubstituted or mono-, di- or trisubstituted by A, NR$^7$SO$_2$A, Het$^3$ and/or ═O, Ar$^2$ denotes phenyl which is unsubstituted or mono-, di-, tri-, tetra or pentasubstituted by Hal, A, (CH$_2$)$_n$OH, (CH$_2$)$_n$OA, (CH$_2$)$_n$CN, NO$_2$, SO$_2$A, COOH, COOA, NH$_2$, NHA, NA$_2$, CHO, COA, (CH$_2$)$_n$CONH$_2$, (CH$_2$)$_n$CONHA, (CH$_2$)$_n$CONA$_2$, CONHHet$^3$, COHet$^3$, Het$^3$, NHCOHet$^3$, NR$^7$SO$_2$A and/or NHCOA, or indanyl, which may be substituted by ═O, Het$^3$ denotes piperidinyl, pyrrolidinyl, morpholinyl, piperazinyl, imidazolidinyl, oxazolidinyl, tetrahydropyranyl, indanyl, dihydropyridazinyl, pyridazinyl, pyridyl, pyrimidinyl, triazolyl, tetrazolyl, 6,7-dihydro-5H-cyclopenta[b]pyridinyl, dihydroindoyl, dihydropyridyl, indolyl, indazolyl, oxazolyl, isoxazolyl, furyl, thienyl, pyrrolyl, imidazolyl, pyrazolyl, quinolyl, quinoxalinyl, quinazolinyl or tetrahydroquinolyl, each of which is unsubstituted or mono- or disubstituted by A, (CH$_2$)$_n$N(R$^7$)$_2$ and/or ═O, A denotes unbranched or branched alkyl having 1-10 C atoms, in which 1-7 H atoms may be replaced by F and/or in which one or two non-adjacent CH and/or CH$_2$ groups may be replaced by O, NH and/or NA', A' denotes unbranched or branched alkyl having 1-6 C atoms, Cyc denotes cyclic alkyl having 3, 4, 5, 6 or 7 C atoms which is unsubstituted or monosubstituted by CON(R$^7$)$_2$ or NR$^7$SO$_2$A, Hal denotes F, Cl, Br or I, n denotes 0, 1 or 2, with the proviso that
a) at least one of $X^1$, $X^2$, $X^3$ and $X^4$ denotes N and a maximum of two simultaneously denote N,
b) if $X^1$=N, then $X^4$≠N and $R^4$≠H,
c) if $X^4$=N, then $X^1$≠N, and pharmaceutically usable salts, tautomers and stereoisomers thereof, including mixtures thereof in all ratios.

The invention relates to the compounds of the formula I and salts thereof and to a process for the preparation of compounds of the formula I in which
$X^1$ denotes N,
$X^2$ denotes C,
$X^3$ denotes C,
$X^4$ denotes C,
$X^5$ denotes C,
$R^4$ denotes $NH(CH_2)_nHet^1$ or $NH(CH_2)_nAr^1$,
and pharmaceutically usable salts, tautomers and stereoisomers thereof, characterised in that
a compound of the formula II

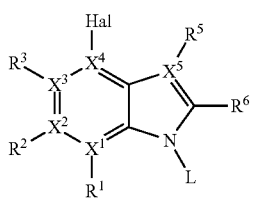

in which
$X^1$ denotes N,
$X^2$, $X^3$, $X^4$, $X^5$ denote C,
Hal denotes Cl, Br or I,
L denotes a silyl protecting group,
and
$R^1$, $R^2$, $R^3$, $R^5$ have the meanings indicated in Claim 1,
is reacted with a compound of the formula IIIa or IIIb

   IIIa

   IIIb, in which $Het^1$, $Ar^1$ and n have the meanings indicated in Claim 1,
and/or
a base or acid of the formula I is converted into one of its salts.

Compounds of the formula I are also taken to mean the hydrates and solvates of these compounds.

The invention also relates to the optically active forms (stereoisomers), the enantiomers, the racemates, the diastereomers and the hydrates and solvates of these compounds. Solvates of the compounds are taken to mean adductions of inert solvent molecules onto the compounds which form owing to their mutual attractive force. Solvates are, for example, monohydrates or dihydrates or alcoholates.

Pharmaceutically usable derivatives are taken to mean, for example, the salts of the compounds according to the invention and also so-called pro-drug compounds.

Prodrug derivatives are taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The invention naturally also relates to the solvates of the salts of the compounds of the formula I.

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

The expression "effective amount" denotes the amount of a medicament or of a pharmaceutical active compound which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence: improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

For all radicals which occur more than once, such as, for example, A, their meanings are independent of one another.
SEM-Cl=2-(trimethylsilyl)ethoxymethyl chloride
S-Phos=2-dicyclohexylphosphino-2',6'-dimethoxybiphenyl
Xanthphos=4,5-bis(diphenylphosphino)-9,9-dimethylxanthene
DABCO=1,4-diazabicyclo[2.2.2]octane
TFA=trifluoroacetic acid A denotes alkyl, is unbranched (linear) or branched and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

One or two non-adjacent CH and/or $CH_2$ groups in the alkyl groups may also be replaced by O, NH and/or NA'.

Alkyl may also denote $CH_2O$—$CH_2$—$CH_2$—OH or $CH_2$—$CH_2N(CH_3)_2$.

A' preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl or benzyl.

Cyclic alkyl preferably denotes cyclopropyl, cyclobutyl, cyclopentyl or cyclohexyl.

A denotes alkoxy and is preferably, for example, methoxy, ethoxy, propoxy, isopropoxy, butoxy, trifluoromethoxy or cyclopentoxy.

—COA (acyl) preferably denotes acetyl, propionyl, furthermore also butyryl, pentanoyl, hexanoyl or, for example, benzoyl.

Hal preferably denotes F, Cl or Br, but also I.
$X^1$ preferably denotes N.
$X^2$ preferably denotes C.
$X^3$ preferably denotes C.
$X^4$ preferably denotes C.
$X^5$ preferably denotes C.
$R^7$ preferably denotes H or methyl.

Ar denotes, for example, unsubstituted phenyl, furthermore preferably, for example, phenyl which is mono-, di- or trisubstituted by A, fluorine, chlorine, bromine, iodine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl, aminocarbonyl, Het³ and/or NHCOHet³.

Ar particularly preferably denotes phenyl which is mono- or disubstituted by $(CH_2)_nOA$ and/or Het³.

Ar¹ denotes, for example, unsubstituted phenyl, furthermore phenyl which is preferably mono-, di- or trisubstituted, for example by A, fluorine, chlorine, bromine, iodine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl, aminocarbonyl, Het³ and/or NHCOHet³.

Ar¹ particularly preferably denotes phenyl which is mono- or disubstituted by Hal, $(CH_2)_nCN$, $NH_2$, NHA, $NA_2$, $(CH_2)_nCONR^7$ and/or $NR^7SO_2A$.

Ar² denotes, for example, unsubstituted phenyl, furthermore preferably phenyl which is mono-, di- or trisubstituted by, for example, A, fluorine, chlorine, bromine, iodine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, benzyloxy, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl, aminocarbonyl Het³ and/or NHCOHet³.

Ar² particularly preferably denotes phenyl which is mono-, di-, tri-tetra- or pentasubstituted by Hal, A, $(CH_2)_nOH$, $(CH_2)_nOA$, COOA, $NH_2$, NHA, $NA_2$, $(CH_2)_nCONH_2$, $(CH_2)_nCONHA$, $(CH_2)_nCONA_2$, CONHHet³, COHet³, Het³ and/or NHCOHet³.

Het preferably denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, quinolinyl, quinoxalinyl, quinazolinyl, pyrrolopyridinyl, purinyl, indolyl, dihydroindolyl, indazolyl, tetrahydroquinolyl, dihydrobenzoxazolyl, dihydropyridyl, dihydropyridazinyl, dihydrobenzimidazolyl, dihydrobenzothiazolyl, piperidinyl, pyrrolidinyl, morpholinyl, piperazinyl, imidazolidinyl, oxazolidinyl or tetrahydropyranyl, each of which is unsubstituted or mono-, di- or trisubstituted by A and/or =O.

Het particularly preferably denotes pyrazolyl or dihydroindolyl, each of which is monosubstituted by A or =O.

Het¹ preferably denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, quinolinyl, quinoxalinyl, quinazolinyl, pyrrolopyridinyl, purinyl, indolyl, dihydroindolyl, indazolyl, tetrahydroquinolyl, dihydrobenzoxazolyl, dihydropyridyl, dihydropyridazinyl, dihydrobenzimidazolyl, dihydrobenzothiazolyl, piperidinyl, pyrrolidinyl, morpholinyl, piperazinyl, imidazolidinyl, oxazolidinyl or tetrahydropyranyl, each of which is unsubstituted or mono-, di- or trisubstituted by A, $NR^7SO_2A$ and/or =O.

Het¹ particularly preferably denotes pyridyl, pyrazolyl or dihydroindolyl, each of which is mono-, di- or trisubstituted by A, OH, $NR^7SO_2A$ and/or =O.

Het² preferably denotes furyl, thienyl, pyrrolyl, imidazolyl, pyrazolyl, oxazolyl, isoxazolyl, thiazolyl, isothiazolyl, pyridyl, pyrimidinyl, triazolyl, tetrazolyl, oxadiazolyl, thiadiazolyl, pyridazinyl, pyrazinyl, benzimidazolyl, benzotriazolyl, quinolinyl, quinoxalinyl, quinazolinyl, pyrrolopyridinyl, purinyl, indolyl, dihydroindolyl, indazolyl, tetrahydroquinolyl, dihydrobenzoxazolyl, dihydropyridyl, dihydropyridazinyl, dihydrobenzimidazolyl, dihydrobenzothiazolyl, piperidinyl, pyrrolidinyl, morpholinyl, piperazinyl, imidazolidinyl, 6,7-dihydro-5H-cyclopenta[b]pyridinyl, oxazolidinyl or tetrahydropyranyl, each of which is unsubstituted or mono-, di- or trisubstituted by A, $NR^7SO_2A$, Het³ and/or =O.

Het² particularly preferably denotes pyridyl, oxadiazolyl, dihydropyridyl, pyridazinyl, pyrimidinyl, oxazolyl, isoxazolyl, 6,7-dihydro-5H-cyclopenta[b]pyridinyl, indolinyl or pyrazolyl, each of which is mono- or disubstituted by A, $NR^7SO_2A$, Het³ and/or =O.

Het³ preferably denotes piperidinyl, pyrrolidinyl, morpholinyl, piperazinyl, imidazolidinyl, oxazolidinyl, tetrahydropyranyl, indanyl, dihydropyridazinyl, pyridazinyl, pyridyl, pyrimidinyl, triazolyl, tetrazolyl, 6,7-dihydro-5H-cyclopenta[b]pyridinyl, dihydroindoyl, dihydropyridyl, indolyl, indazolyl, oxazolyl, isoxazolyl, furyl, thienyl, pyrrolyl, imidazolyl, pyrazolyl, quinolyl, quinoxalinyl, quinazolinyl or tetrahydroquinolyl, each of which is unsubstituted or mono- or disubstituted by A, $(CH_2)_nN(R^7)_2$ and/or =O.

Het³ particularly preferably denotes piperidinyl, pyrrolidinyl, morpholinyl or piperazinyl, each of which is unsubstituted or mono- or disubstituted by A, $(CH_2)_nN(R^7)_2$ and/or =O.

Accordingly, the invention relates, in particular, to the compounds of the formula I in which at least one of the radicals mentioned has one of the preferred meanings indicated above. Some preferred groups of compounds can be expressed by the following sub-formulae Ia to Ig, which correspond to the formula I and in which the radicals not designated in greater detail have the meaning indicated in the case of the formula I, but in which in Ia Ar denotes phenyl which is mono- or disubstituted by $(CH_2)_nOA$ and/or Het³;

in Ib Het denotes pyrazolyl or dihydroindolyl, each of which is monosubstituted by A or =O;

in Ic Het¹ denotes pyridyl, pyrazolyl or dihydroindolyl, each of which is mono-, di- or trisubstituted by A, OH, $NR^7SO_2A$ and/or =O;

in Id Ar¹ denotes phenyl which is mono- or disubstituted by Hal, $(CH_2)_nCN$, $NH_2$, NHA, $NA_2$, $(CH_2)_nCONR^7$ and/or $NR^7SO_2A$;

in Ie Het² denotes pyridyl, oxadiazolyl, dihydropyridyl, pyridazinyl, pyrimidinyl, oxazolyl, isoxazolyl, 6,7-dihydro-5H-cyclopenta[b]pyridinyl, indolinyl or pyrazolyl, each of which is mono- or disubstituted by A, $NR^7SO_2A$, Het³ and/or =O;

in If Ar² denotes phenyl which is mono-, di-, tri-, tetra or pentasubstituted by Hal, A, $(CH_2)_nOH$, $(CH_2)_nOA$, COOA, $NH_2$, NHA, $NA_2$, $(CH_2)_nCONH_2$, $(CH_2)_nCONHA$, $(CH_2)_nCONA_2$, CONHHet³, COHet³, Het³ and/or NHCOHet³, or indanyl, which may be substituted by =O;

in Ig Het³ denotes piperidinyl, pyrrolidinyl, morpholinyl or piperazinyl, each of which is unsubstituted or mono- or disubstituted by A, $(CH_2)_nN(R^7)_2$ and/or =O, in Ih $X^1$ denotes C or N, $X^2$ denotes C or N, $X^3$ denotes C or N, $X^4$ denotes C or N, $X^5$ denotes C or N, $R^1$ is absent if $X^1$=N or
denotes NH(CH$_2$)$_n$Het or NH(CH$_2$)$_n$Ar,
R$^2$ is absent if X$^2$=N
or
denotes H or Het$^1$,
R$^3$ is absent if X$^3$=N,
or
denotes H, CN, A, Hal, Cyc, OH or OA,
R$^4$ is absent if X$^4$=N
or
denotes H, NH(CH$_2$)$_n$Het$^1$, O(CH$_2$)$_n$Het$^1$, NH(CH$_2$)$_n$Ar$^1$, ═Ar$^1$, (CH$_2$)$_n$Ar$^1$ or NH-Cyc,
R$^5$ is absent if X$^5$=N
or
denotes H or Hal,
R$^6$ denotes H, Ar$^2$, A, Het$^2$, COHet$^3$, CONH$_2$, CONHA, CONA$_2$ or Cyc,
R$^7$ denotes H or alkyl having 1, 2, 3 or 4 C atoms,
Het denotes pyrazolyl or dihydroindolyl, each of which is monosubstituted by A or ═O,
Ar denotes phenyl which is mono- or disubstituted by (CH$_2$)$_n$OA and/or Het$^3$,
Het$^1$ denotes pyridyl, pyrazolyl or dihydroindolyl, each of which is mono-, di- or trisubstituted by A, OH, NR$^7$SO$_2$A and/or ═O,
Ar$^1$ denotes phenyl which is mono- or disubstituted by Hal, (CH$_2$)$_n$CN, NH$_2$, NHA, NA$_2$, (CH$_2$)$_n$CONR$^7$ and/or NR$^7$SO$_2$A,
Het$^2$ denotes pyridyl, oxadiazolyl, dihydropyridyl, pyridazinyl, pyrimidinyl, oxazolyl, isoxazolyl, 6,7-dihydro-5H-cyclopenta[b]pyridinyl, indolinyl or pyrazolyl, each of which is mono- or disubstituted by A, NR$^7$SO$_2$A, Het$^3$ and/or ═O,
Ar$^2$ denotes phenyl which is mono-, di-, tri-, tetra or pentasubstituted by Hal, A, (CH$_2$)$_n$OH, (CH$_2$)$_n$OA, COOA, NH$_2$, NHA, NA$_2$, (CH$_2$)$_n$CONH$_2$, (CH$_2$)$_n$CONHA, (CH$_2$)$_n$CONA$_2$, CONHHet$^3$, COHet$^3$, Het$^3$ and/or NHCOHet$^3$,
or indanyl, which may be substituted by ═O,
Het$^3$ denotes piperidinyl, pyrrolidinyl, morpholinyl or piperazinyl, each of which is unsubstituted or mono- or disubstituted by A, (CH$_2$)$_n$N(R$^7$)$_2$ and/or ═O,
A denotes unbranched or branched alkyl having 1-10 C atoms, in which 1-7 H atoms may be replaced by F and/or in which one or two non-adjacent CH and/or CH$_2$ groups may be replaced by O, NH and/or NA',
A' denotes unbranched or branched alkyl having 1-6 C atoms,
Cyc denotes cyclic alkyl having 3, 4, 5, 6 or 7 C atoms which is unsubstituted or monosubstituted by CON(R$^7$)$_2$ or NR$^7$SO$_2$A,
Hal denotes F, Cl, Br or I,
n denotes 0, 1 or 2,
with the proviso that
a) at least one of X$^1$, X$^2$, X$^3$ and X$^4$ denotes N and a maximum of two simultaneously denote N,
b) if X$^1$=N, then X$^4$≠N and R$^4$≠H,
c) if X$^4$=N, then X$^1$≠N;
in Ii X$^1$ denotes N,
X$^2$ denotes C,
X$^3$ denotes C,
X$^4$ denotes C,
X$^5$ denotes C,
R$^1$ is absent
R$^2$ denotes H or Het$^1$,
R$^3$ denotes H, CN, A, Hal, Cyc, OH or OA,
R$^4$ denotes H, NH(CH$_2$)$_n$Het$^1$, O(CH$_2$)$_n$Het$^1$, NH(CH$_2$)$_n$Ar$^1$, ═Ar$^1$, (CH$_2$)$_n$Ar$^1$ or NH-Cyc,
R$^5$ denotes H or Hal,
R$^6$ denotes H, Ar$^2$, A, Het$^2$, COHet$^3$, CONH$_2$, CONHA, CONA$_2$ or Cyc,
R$^7$ denotes H or alkyl having 1, 2, 3 or 4 C atoms,
Het denotes pyrazolyl or dihydroindolyl, each of which is monosubstituted by A or ═O,
Ar denotes phenyl which is mono- or disubstituted by (CH$_2$)$_n$OA and/or Het$^3$,
Het$^1$ denotes pyridyl, pyrazolyl or dihydroindolyl, each of which is mono-, di- or trisubstituted by A, OH, NR$^7$SO$_2$A and/or ═O,
Ar$^1$ denotes phenyl which is mono- or disubstituted by Hal, (CH$_2$)$_n$CN, NH$_2$, NHA, NA$_2$, (CH$_2$)$_n$CONR$^7$ and/or NR$^7$SO$_2$A,
Het$^2$ denotes pyridyl, oxadiazolyl, dihydropyridyl, pyridazinyl, pyrimidinyl, oxazolyl, isoxazolyl, 6,7-dihydro-5H-cyclopenta[b]pyridinyl, indolinyl or pyrazolyl, each of which is mono- or disubstituted by A, NR$^7$SO$_2$A, Het$^3$ and/or ═O,
Ar$^2$ denotes phenyl which is mono-, di-, tri-, tetra or pentasubstituted by Hal, A, (CH$_2$)$_n$OH, (CH$_2$)$_n$OA, COOA, NH$_2$, NHA, NA$_2$, (CH$_2$)$_n$CONH$_2$, (CH$_2$)$_n$CONHA, (CH$_2$)$_n$CONA$_2$, CONHHet$^3$, COHet$^3$, Het$^3$ and/or NHCOHet$^3$,
or indanyl, which may be substituted by ═O,
Het$^3$ denotes piperidinyl, pyrrolidinyl, morpholinyl or piperazinyl, each of which is unsubstituted or mono- or disubstituted by A, (CH$_2$)$_n$N(R$^7$)$_2$ and/or ═O,
A denotes unbranched or branched alkyl having 1-10 C atoms, in which 1-7 H atoms may be replaced by F and/or in which one or two non-adjacent CH and/or CH$_2$ groups may be replaced by O, NH and/or NA',
A' denotes unbranched or branched alkyl having 1-6 C atoms,
Cyc denotes cyclic alkyl having 3, 4, 5, 6 or 7 C atoms which is unsubstituted or monosubstituted by CON(R$^7$)$_2$ or NR$^7$SO$_2$A,
Hal denotes F, Cl, Br or I,
n denotes 0, 1 or 2;
and pharmaceutically usable salts, tautomers and stereoisomers thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use may also be made here of variants known per se which are not mentioned here in greater detail.

If desired, the starting materials can also be formed in situ by not isolating them from the reaction mixture, but instead immediately converting them further into the compounds of the formula I.

The starting compounds of the formulae II and III are generally known. If they are novel, however, they can be prepared by methods known per se.

Compounds of the formula I can preferably be obtained by reacting compounds of the formula II with compounds of the formula III.

The reaction is carried out by methods which are known to the person skilled in the art.

The reaction is carried out in an inert solvent.

Suitable inert solvents are, for example, hydrocarbons, such as hexane, petroleum ether, benzene, toluene or xylene;

chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate or mixtures of the said solvents.

Particular preference is given dioxane.

Depending on the conditions used, the reaction time is between a few minutes and 14 days, the reaction temperature is between about −30° and 140°, normally between 20° and 150°, in particular between about 40° and about 140°.

The reaction is preferably carried out under Buchwald conditions, which are known to the person skilled in the art.

Compounds of the formula I can furthermore preferably be obtained by reacting compounds of the formula IV with compounds of the formula V.

The reaction is carried out in an inert solvent.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given n-butanol.

Depending on the conditions used, the reaction time is between a few minutes and 14 days, the reaction temperature is between about −30° and 140°, normally between −10° and 90°, in particular between about 0° and about 70°.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. If the compound according to the invention contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline-earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline-earth metal salts calcium and magnesium. Salts of the compounds according to the invention which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di$(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds according to the invention are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds according to the invention are formed with metals or amines, such as alkali metals and alkaline-earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active compound which comprises a compound according to the invention in the form of one of its salts, in particular if this salt form imparts improved pharmacokinetic properties on the active compound compared with the free form of the active compound or any other salt form of the active compound used earlier. The pharmaceutically acceptable salt form of the active compound can also provide this active compound for the first time with a desired pharmacokinetic property which it did not have earlier and can even have a positive influence on the pharmacodynamics of this active compound with respect to its therapeutic efficacy in the body.

Compounds according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

Isotopes

It is furthermore intended that a compound of the formula I includes isotope-labelled forms thereof. An isotope-labelled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug thereof or a pharmaceutically acceptable salt of either which contains one or more of the above-mentioned isotopes and/or other isotopes of other atoms is intended to be part of the present invention. An isotope-labelled compound of the formula I can be used in a number of beneficial ways. For example, an isotope-labelled compound of the formula I into which, for example, a radioisotope, such as $^3H$ or $^{14}C$, has been incorporated is suitable for medicament and/or substrate tissue distribution assays. These radioisotopes, i.e. tritium ($^3H$) and carbon-14 ($^{14}C$), are particularly preferred owing to their simple preparation and excellent detectability. Incorporation of heavier isotopes, for example deuterium ($^2H$), into a compound of the formula I has therapeutic advantages owing to the higher metabolic stability of this isotope-labelled compound. Higher metabolic stability translates directly into an increased in-vivo half-life or lower dosages, which under most circumstances would represent a preferred embodiment of the present invention. An isotope-labelled compound of the formula I can usually be prepared by carrying out the procedures disclosed in the synthesis schemes and the related description, in the example part and in the preparation part in the present text, replacing a non-isotope-labelled reactant with a readily available isotope-labelled reactant.

In order to manipulate the oxidative metabolism of the compound by way of the primary kinetic isotope effect, deuterium ($^2H$) can also be incorporated into a compound of the formula I. The primary kinetic isotope effect is a change in the rate of a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom in a non-exchangeable position, rate differences of $k_M/k_D$=2-7 are typical. If this rate difference is successfully applied to a compound of the formula I that is susceptible to oxidation, the profile of this compound in vivo can thereby be drastically modified and result in improved pharmacokinetic properties.

When discovering and developing therapeutic agents, the person skilled in the art attempts to optimise pharmacokinetic parameters while retaining desirable in-vitro properties. It is reasonable to assume that many compounds with poor pharmacokinetic profiles are susceptible to oxidative metabolism. In-vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of the compounds of the formula I are thereby obtained and can be expressed quantitatively in terms of increases in the in-vivo half-life (T/2), concentration at maximum therapeutic effect ($C_{max}$), area under the dose response curve (AUC), and F; and in terms of reduced clearance, dose and costs of materials.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the undesired metabolite, even if the particular oxidation is not a rate-determining step. Further information on the state of the art with respect to deuterium-hydrogen exchange is given, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al., Biochemistry 33(10), 2927-2937, 1994, and Jarman et al., Carcinogenesis 16(4), 683-688, 1993.

The invention furthermore relates to the use of the compounds and/or physiologically acceptable salts thereof for the preparation of a medicament (pharmaceutical composition), in particular by non-chemical methods. They can be converted into a suitable dosage form here together with at least one solid, liquid and/or semi-liquid excipient or adjuvant and, if desired, in combination with one or more further active compounds.

The invention furthermore relates to medicaments comprising at least one compound according to the invention and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active compound per dosage unit. Such a unit can comprise, for example, 0.1 mg to 3 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active compound per dosage unit. Preferred dosage unit formulations are those which comprise a daily dose or part-dose, as indicated above, or a corresponding fraction thereof of an active compound. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active compound with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention and the salts thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active compound can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active compound can be employed either with a paraffinic or a water-miscible cream base. Alternatively, the active compound can be formulated to give a cream with an oil-in-water cream base or a water-in-oil base.

Pharmaceutical formulations adapted for topical application to the eye include eye drops, in which the active compound is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the present invention depends on a number of factors, including, for example, the age and weight of the human or animal, the precise condition requiring treatment, and its severity, the nature of the formulation and the method of administration, and is ultimately determined by the treating doctor or vet.

However, an effective amount of a compound according to the invention for the treatment is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate thereof can be determined as the fraction of the effective amount of the compound according to the invention per se. It can be assumed that similar doses are suitable for the treatment of other conditions mentioned above.

The invention furthermore relates to medicaments comprising at least one compound according to the invention and/or pharmaceutically usable salts, tautomers and stereoisomers thereof, including mixtures thereof in all ratios, and at least one further medicament active compound.

Further medicament active compounds are preferably chemotherapeutic agents, in particular those which inhibit angiogenesis and thus inhibit the growth and spread of tumour cells; preference is given here to VEGF receptor inhibitors, including robozymes and antisense which are directed to VEGF receptors, and angiostatin and endostatin.

Examples of antineoplastic agents which can be used in combination with the compounds according to the invention generally include alkylating agents, antimetabolites; epidophyllotoxin; an antineoplastic enzyme; a topoisomerase inhibitor; procarbazin; mitoxantron or platinum coordination complexes.

Antineoplastic agents are preferably selected from the following classes: anthracyclins, vinca medicaments, mitomycins, bleomycins, cytotoxic nucleosides, epothilones, discodermolides, pteridines, diynenes and podophyllotoxins.

Particular preference is given in the said classes to, for example, carminomycin, daunorubicin, aminopterin, methotrexate, methopterin, dichloromethotrexate, mitomycin C, porfiromycin, 5-fluorouracil, 6-mercaptopurine, gemcitabine, cytosinarabinoside, podophyllotoxin or podophyllotoxin derivatives, such as, for example, etoposide, etoposide phosphate or teniposide, melphalan, vinblastine, vincristine, leurosidine, vindesine, leurosine and paclitaxel. Other preferred antineoplastic agents are selected from the group estramustine, carboplatin, cyclophosphamide, bleomycin, gemcitabine, ifosamide, melphalan, hexamethylmelamine, thiotepa, cytarabin, idatrexate, trimetrexate, dacarbazine, L-asparaginase, camptothecin, CPT-11, topotecan, arabinosylcytosine, bicalutamide, flutamide, leuprolide, pyridobenzoindole derivatives, interferons and interleukins.

The invention also relates to a set (kit) consisting of separate packs of
(a) an effective amount of a compound according to the invention and/or pharmaceutically usable salts, tautomers and stereoisomers thereof, including mixtures thereof in all ratios,
and
(b) an effective amount of a further medicament active compound.

The set comprises suitable containers, such as boxes, individual bottles, bags or ampoules. The set may, for example, comprise separate ampoules, each containing an effective amount of a compound according to the invention and/or pharmaceutically usable salts, tautomers and stereoisomers thereof, including mixtures thereof in all ratios, and an effective amount of a further medicament active compound in dissolved or lyophilised form.

Use

The present compounds are suitable as pharmaceutical active compounds for mammals, especially for humans, in the treatment of tyrosine kinase-induced diseases. These diseases include the proliferation of tumour cells, pathological neovascularisation (or angiogenesis) which promotes the growth of solid tumours, ocular neovascularisation (diabetic retinopathy, age-induced macular degeneration and the like) and inflammation (psoriasis, rheumatoid arthritis and the like).

The present invention encompasses the use of the compounds of the formula I and/or physiologically acceptable salts, tautomers and stereoisomers thereof for the preparation of a medicament for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma. A further group of preferred forms of cancer are monocytic leukaemia, lung adenocarcinoma, small-cell lung carcinomas, pancreatic cancer, glioblastomas and breast carcinoma.

Also encompassed is the use of the compounds according to Claim 1 according to the invention and/or physiologically acceptable salts, tautomers and stereoisomers thereof for the preparation of a medicament for the treatment or prevention of a disease in which angiogenesis is implicated. Such a disease in which angiogenesis is implicated is an ocular disease, such as retinal vascularisation, diabetic retinopathy, age-induced macular degeneration and the like.

The use of compounds of the formula I and/or physiologically acceptable salts, tautomers and stereoisomers thereof for the preparation of a medicament for the treatment or prevention of inflammatory diseases also falls within the scope of the present invention. Examples of such inflammatory diseases include rheumatoid arthritis, psoriasis, contact dermatitis, delayed hypersensitivity reaction and the like.

Also encompassed is the use of the compounds of the formula I and/or physiologically acceptable salts, tautomers and stereoisomers thereof for the preparation of a medicament for the treatment or prevention of a tyrosine kinase-induced disease or a tyrosine kinase-induced condition in a mammal, in which to this method a therapeutically effective amount of a compound according to the invention is administered to a sick mammal in need of such treatment. The therapeutic amount varies according to the specific disease and can be determined by the person skilled in the art without undue effort.

The present invention also encompasses the use compounds of the formula I and/or physiologically acceptable salts and solvates thereof for the preparation of a medicament for the treatment or prevention of retinal vascularisation.

Methods for the treatment or prevention of ocular diseases, such as diabetic retinopathy and age-induced macular degeneration, are likewise part of the invention. The use for the treatment or prevention of inflammatory diseases, such as rheumatoid arthritis, psoriasis, contact dermatitis and delayed hypersensitivity reaction, as well as the treatment or prevention of bone pathologies from the group osteosarcoma, osteoarthritis and rickets, likewise falls within the scope of the present invention.

The expression "tyrosine kinase-induced diseases or conditions" refers to pathological conditions that depend on the activity of one or more tyrosine kinases. Tyrosine kinases either directly or indirectly participate in the signal transduction pathways of a variety of cellular activities, including proliferation, adhesion and migration and differentiation. Diseases associated with tyrosine kinase activity include proliferation of tumour cells, pathological neovascularisation that promotes the growth of solid tumours, ocular neovascularisation (diabetic retinopathy, age-induced macular degeneration and the like) and inflammation (psoriasis, rheumatoid arthritis and the like).

The compounds of the formula I can be administered to patients for the treatment of cancer, in particular fast-growing tumours.

The invention thus relates to the use of compounds of the formula I, and pharmaceutically usable salts, tautomers and stereoisomers thereof, including mixtures thereof in all ratios, for the preparation of a medicament for the treatment of diseases in which the inhibition, regulation and/or modulation of kinase signal transduction plays a role.

Preference is given to the use of compounds of the formula I, and pharmaceutically usable salts, tautomers and stereoisomers thereof, including mixtures thereof in all ratios, for the preparation of a medicament for the treatment of diseases which are influenced by inhibition of tyrosine kinases by the compounds according to Claim 1.

Particular preference is given to the use for the treatment of a disease where the disease is a solid tumour.

The solid tumour is preferably selected from the group of tumours of the lung, squamous epithelium, the bladder, the stomach, the kidneys, of head and neck, the oesophagus, the cervix, the thyroid, the intestine, the liver, the brain, the prostate, the urogenital tract, the lymphatic system, the stomach and/or the larynx.

The solid tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myeloid leukaemia, chronic myeloid leukaemia, acute lymphatic leukaemia and/or chronic lymphatic leukaemia.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic/DNA-damaging agents and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines, like adriamycin, bleomycin, doxorubicin, daunomycin, epirubicin, idarubicin, mitomycin-C, dactinomycin and mithramycin); antimitotic agents (for example vinca alkaloids, like vincristine, vinblastine, vindesine and vinorelbine, and taxoids, like taxol and taxotere); topoisomerase inhibitors (for example epipodophyllotoxins, like etoposide and teniposide, amsacrine, topotecan, irinotecan and camptothecin) and cell-differentiating agents (for example all-trans-retinoic acid, 13-cis-retinoic acid and fenretinide);

(ii) cytostatic agents, such as antioestrogens (for example tamoxifen, toremifene, raloxifene, droloxifene and iodoxyfene), oestrogen receptor downregulators (for example fulvestrant), antiandrogens (for example bicalutamide, flutamide, nilutamide and cyproterone acetate), LHRH antagonists or LHRH agonists (for example goserelin, leuprorelin and buserelin), progesterones (for example megestrol acetate), aromatase inhibitors (for example as anastrozole, letrozole, vorazole and exemestane) and inhibitors of 5α-reductase, such as finasteride;

(iii) agents which inhibit cancer cell invasion (for example metalloproteinase inhibitors, like marimastat, and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the antier-bb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy)quinazolin-4-amine (gefitinib, AZD-1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy) quinazolin-4-amine (CI 1033)), for example inhibitors of the platelet-derived growth factor family and for example inhibitors of the hepatocyte growth factor family;

(v) antiangiogenic agents, such as those which inhibit the effects of vascular endothelial growth factor, (for example the anti-vascular endothelial cell growth factor antibody bevacizumab [Avastin™], compounds such as those disclosed in published international patent applications WO 97/22596, WO 97/30035, WO 97/32856 and WO 98/13354) and compounds that work by other mechanisms (for example linomide, inhibitors of integrin αvβ3 function and angiostatin);

(vi) vessel-damaging agents, such as combretastatin A4 and compounds disclosed in international patent applications WO 99/02166, WO 00/40529, WO 00/41669, WO 01/92224, WO 02/04434 and WO 02/08213;

(vii) antisense therapies, for example those which are directed to the targets listed above, such as ISIS-2503, an anti-Ras antisense;

(viii) gene therapy approaches, including, for example, approaches for replacement of aberrant genes, such as aberrant p53 or aberrant BRCA1 or BRCA2, GDEPT (gene-directed enzyme pro-drug therapy) approaches, such as those using cytosine deaminase, thymidine kinase or a bacterial nitroreductase enzyme, and approaches for increasing patient tolerance to chemotherapy or radiotherapy, such as multi-drug resistance gene therapy; and (ix) immunotherapy approaches, including, for example, ex-vivo and in-vivo approaches for increasing the immunogenicity of patient tumour cells, such as transfection with cytokines, such as interleukin 2, interleukin 4 or granulocyte-macrophage colony stimulating factor, approaches for decreasing T-cell anergy, approaches using transfected immune cells, such as cytokine-transfected dendritic cells, approaches using cytokine-transfected tumour cell lines, and approaches using anti-idiotypic antibodies.

The medicaments from Table 1 below are preferably, but not exclusively, combined with the compounds of the formula I.

TABLE 1

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | Chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aeterna) |
| | Carboxyphthalatoplatinum | Satraplatin (Johnson Matthey) |
| | Tetraplatin | BBR-3464 (Hoffmann-La Roche) |
| | Ormiplatin | SM-11355 (Sumitomo) |
| | Iproplatin | AP-5280 (Access) |
| Antimetabolites | Azacytidine | Tomudex |
| | Gemcitabine | Trimetrexate |
| | Capecitabine | Deoxycoformycin |
| | 5-Fluorouracil | Fludarabine |
| | Floxuridine | Pentostatin |
| | 2-Chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-Fluorodesoxycytidine | Irofulven (MGI Pharrna) |
| | Methotrexate | DMDC (Hoffmann-La Roche) |
| | Idatrexate | Ethynylcytidine (Taiho) |
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-Ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | Pixantrone (Novuspharma) | BNP-1350 (BioNumerik) |
| | Rebeccamycin analogue (Exelixis) | CKD-602 (Chong Kun Dang) |
| | BBR-3576 (Novuspharma) | KW-2170 (Kyowa Hakko) |
| Antitumour antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | Epirubicin | Bleomycin sulfate (Blenoxan) |
| | Therarubicin | Bleomycinic acid |
| | Idarubicin | Bleomycin A |
| | Rubidazon | Bleomycin B |
| | Plicamycinp | Mitomycin C |
| | Porfiromycin | MEN-10755 (Menarini) |
| | Cyanomorpholinodoxorubicin | GPX-100 (Gem Pharmaceuticals) |
| | Mitoxantron (Novantron) | |
| Antimitotic agents | Paclitaxel | SB 408075 (GlaxoSmithKline) |
| | Docetaxel | E7010 (Abbott) |
| | Colchicine | PG-TXL (Cell Therapeutics) |
| | Vinblastine | IDN 5109 (Bayer) |
| | Vincristine | A 105972 (Abbott) |
| | Vinorelbine | A 204197 (Abbott) |
| | Vindesine | LU 223651 (BASF) |
| | Dolastatin 10 (NCl) | D 24851 (ASTA Medica) |
| | Rhizoxin (Fujisawa) | ER-86526 (Eisai) |
| | Mivobulin (Warner-Lambert) | Combretastatin A4 (BMS) |
| | Cemadotin (BASF) | Isohomohalichondrin-B (PharmaMar) |
| | RPR 109881A (Aventis) | ZD 6126 (AstraZeneca) |
| | TXD 258 (Aventis) | PEG-Paclitaxel (Enzon) |
| | Epothilone B (Novartis) | AZ10992 (Asahi) |
| | T 900607 (Tularik) | !DN-5109 (Indena) |
| | T 138067 (Tularik) | AVLB (Prescient NeuroPharma) |
| | Cryptophycin 52 (Eli Lilly) | Azaepothilon B (BMS) |
| | Vinflunine (Fabre) | BNP-7787 (BioNumerik) |
| | Auristatin PE (Teikoku Hormone) | CA-4-prodrug (OXiGENE) |
| | BMS 247550 (BMS) | Dolastatin-10 (NrH) |
| | BMS 184476 (BMS) | CA-4 (OXiGENE) |
| | BMS 188797 (BMS) | |
| | Taxoprexin (Protarga) | |

TABLE 1-continued

| | | |
|---|---|---|
| Aromatase inhibitors | Aminoglutethimide<br>Letrozole<br>Anastrazole<br>Formestan | Exemestan<br>Atamestan (BioMedicines)<br>YM-511 (Yamanouchi) |
| Thymidylate Synthase inhibitors | Pemetrexed (Eli Lilly)<br>ZD-9331 (BTG) | Nolatrexed (Eximias)<br>CoFactor ™ (BioKeys) |
| DNA antagonists | Trabectedin (PharmaMar)<br>Glufosfamide (Baxter International)<br>Albumin + 32P<br>(Isotope Solutions)<br>Thymectacin (NewBiotics)<br>Edotreotid (Novartis) | Mafosfamide (Baxter International)<br>Apaziquone (Spectrum<br>Pharmaceuticals)<br>O6-benzylguanine (Paligent) |
| Farnesyl transferase inhibitors | Arglabin (NuOncology Labs)<br>Ionafarnib (Schering-Plough)<br>BAY-43-9006 (Bayer) | Tipifarnib (Johnson & Johnson)<br>Perillyl alcohol (DOR BioPharma) |
| Pump inhibitors | CBT-1 (CBA Pharma)<br><br>Tariquidar (Xenova)<br>MS-209 (Schering AG) | Zosuquidar trihydrochloride<br>(Eli Lilly)<br>Biricodar dicitrate (Vertex) |
| Histone acetyl transferase inhibitors | Tacedinaline (Pfizer)<br>SAHA (Aton Pharma)<br>MS-275 (Schering AG) | Pivaloyloxymethyl butyrate (Titan<br>Depsipeptide (Fujisawa) |
| Metalloproteinase inhibitors | Neovastat (Aeterna Laboratories)<br>Marimastat (British Biotech) | CMT-3 (CollaGenex)<br>BMS-275291 (Celltech) |
| Ribonucleoside reductase inhibitors | Gallium maltolate (Titan)<br>Triapin (Vion) | Tezacitabine (Aventis)<br>Didox (Molecules for Health) |
| TNF-alpha agonists/antagonists | Virulizin (Lorus Therapeutics)<br>CDC-394 (Celgene) | Revimid (Celgene) |
| Endothelin-A receptor antagonists | Atrasentan (Abbot)<br>ZD-4054 (AstraZeneca) | YM-598 (Yamanouchi) |
| Retinoic acid receptor agonists | Fenretinide (Johnson & Johnson)<br>LGD-1550 (ligand) | Alitretinoin (Ligand) |
| Immunomodulators | Interferon<br>Oncophage (Antigenics)<br>GMK (Progenics)<br>Adenocarcinoma vaccine<br>(Biomira)<br>CTP-37 (AVI BioPharma)<br>JRX-2 (Immuno-Rx)<br>PEP-005 (Peplin Biotech)<br>Synchrovax vaccines (CTL Immuno)<br>Melanoma vaccine<br>(CTL Immuno)<br>p21-RAS vaccine (GemVax) | Dexosome therapy (Anosys)<br>Pentrix (Australian Cancer<br>Technology)<br>JSF-154 (Tragen)<br>Cancer vaccine (Intercell)<br>Norelin (Biostar)<br>BLP-25 (Biomira)<br>MGV (Progenics)<br>!3-Alethin (Dovetail)<br>CLL-Thera (Vasogen) |
| Hormonal and antihormonal agents | Oestrogens<br>Conjugated oestrogens<br>Ethynyloestradiol<br>Chlorotrianisene<br>Idenestrol<br>Hydroxyprogesterone caproate<br>Medroxyprogesterone<br>Testosterone<br>Testosterone propionate<br>Fluoxymesterone<br>Methyltestosterone<br>Diethylstilbestrol<br>Megestrol<br>Tamoxifen<br>Toremofin<br>Dexamethasone | Prednisone<br>Methylprednisolone<br>Prednisolone<br>Aminoglutethimide<br>Leuprolide<br>Goserelin<br>Leuporelin<br>Bicalutamide<br>Flutamide<br>Octreotide<br>Nilutamide<br>Mitotan<br>P-04 (Novogen)<br>2-Methoxyoestradiol (EntreMed)<br>Arzoxifen (Eli Lilly) |
| Photodynamic agents | Talaporfin (Light Sciences)<br>Theralux (Theratechnologies)<br>Motexafin-Gadolinium (Pharmacyclics | Pd-Bacteriopheophorbid (Yeda)<br>Lutetium-Texaphyrin<br>(Pharmacyclics)<br>Hypericin |
| Tyrosine kinase inhibitors | Imatinib (Novartis)<br>Leflunomide(Sugen/Pharmacia)<br>ZD1839 (AstraZeneca)<br>Erlotinib (Oncogene Science)<br>Canertjnib (Pfizer)<br>Squalamine (Genaera)<br>SU5416 (Pharmacia)<br>SU6668 (Pharmacia)<br>ZD4190 (AstraZeneca)<br>ZD6474 (AstraZeneca) | Kahalide F (PharmaMar)<br>CEP-701 (Cephalon)<br>CEP-751 (Cephalon)<br>MLN518 (Millenium)<br>PKC412 (Novartis)<br>Phenoxodiol O<br>Trastuzumab (Genentech)<br>C225 (ImClone)<br>rhu-Mab (Genentech)<br>MDX-H210 (Medarex) |

TABLE 1-continued

| | | |
|---|---|---|
| | Vatalanib (Novartis) | 2C4 (Genentech) |
| | PKI166 (Novartis) | MDX-447 (Medarex) |
| | GW2016 (GlaxoSmithKline) | ABX-EGF (Abgenix) |
| | EKB-509 (Wyeth) | IMC-1C11 (ImClone) |
| | EKB-569 (Wyeth) | |
| Various agents | SR-27897 (CCK-A inhibitor, Sanofi-Synthelabo) | BCX-1777 (PNP inhibitor, BioCryst) |
| | Tocladesine (cyclic AMP agonist, Ribapharm) | Ranpirnase (ribonuclease stimulant, Alfacell) |
| | Alvocidib (CDK inhibitor, Aventis) | Galarubicin (RNA synthesis inhibitor, Dong-A) |
| | CV-247 (COX-2 inhibitor, Ivy Medical) | Tirapazamine (reducing agent, SRI International) |
| | P54 (COX-2 inhibitor, Phytopharm) | N-Acetylcysteine (reducing agent, Zambon) |
| | CapCell ™ (CYP450 stimulant, Bavarian Nordic) | R-Flurbiprofen (NF-kappaB inhibitor, Encore) |
| | GCS-IOO (gal3 antagonist, GlycoGenesys) | 3CPA (NF-kappaB inhibitor, Active Biotech) |
| | G17DT immunogen (gastrin inhibitor, Aphton) | Seocalcitol (vitamin D receptor agonist, Leo) |
| | Efaproxiral (oxygenator, Allos Therapeutics) | 131-I-TM-601 (DNA antagonist, TransMolecular) |
| | PI-88 (heparanase inhibitor, Progen) | Eflornithin (ODC inhibitor, ILEX Oncology) |
| | Tesmilifen (histamine antagonist, YM BioSciences) | Minodronic acid (osteoclast inhibitor, Yamanouchi) |
| | Histamine (histamine H2 receptor agonist, Maxim) | Indisulam (p53 stimulant, Eisai) |
| | Tiazofurin (IMPDH inhibitor, Ribapharm) | Aplidin (PPT inhibitor, PharmaMar) |
| | Cilengitide (integrin antagonist, Merck KGaA) | Rituximab (CD20 antibody, Genentech) |
| | SR-31747 (IL-1 antagonist, Sanofi-Synthelabo) | Gemtuzumab (CD33 antibody, Wyeth Ayerst) |
| | CCI-779 (mTOR kinase inhibitor, Wyeth) | PG2 (haematopoiesis promoter, Pharmagenesis) |
| | Exisulind (PDE-V inhibitor, Cell Pathways) | Immunol ™ (triclosan mouthwash, Endo) |
| | CP-461 (PDE-V inhibitor, Cell Pathways) | Triacetyluridine (uridine prodrug, Wellstat) |
| | AG-2037 (GART inhibitor, Pfizer) | SN-4071 (sarcoma agent, Signature BioScience) |
| | WX-UK1 (plasminogen activator inhibitor, Wilex) | TransMID-107 ™ (immunotoxin, KS Biomedix) |
| | PBI-1402 (PMN stimulant, ProMetic LifeSciences) | PCK-3145 (apoptosis promoter, Procyon) |
| | Bortezomib (proteasome inhibitor, Millennium) | Doranidazole (apoptosis promote Pola) |
| | SRL-172 (T-cell stimulant, SR Pharma) | CHS-828 (cytotoxic agent, Leo) |
| | TLK-286 (glutathione-S transferase inhibitor, Telik) | trans-Retinoic acid (differentiator NIH) |
| | PT-100 (growth factor agonist, Point Therapeutics) | MX6 (apoptosis promoter, MAXIA) |
| | Midostaurin (PKC inhibitor, Novartis) | Apomine (apoptosis promoter, ILEX Oncology) |
| | Bryostatin-1 (PKC stimulant, GPC Biotech) | Urocidin (apoptosis promoter, Bioniche) |
| | CDA-II (apoptosis promoter, Everlife) | Ro-31-7453 (apoptosis promoter La Roche) |
| | SDX-101 (apoptosis promoter, Salmedix) | Brostallicin (apoptosis promoter, Pharmacia) |
| | Ceflatonin (apoptosis promoter, ChemGenex) | |

A combined treatment of this type can be achieved with the aid of simultaneous, consecutive or separate dispensing of the individual components of the treatment. Combination products of this type employ the compounds according to the invention.

The invention relates to compounds of the formula I and pharmaceutically usable salts, tautomers and stereoisomers thereof, including mixtures thereof in all ratios, for use for the treatment of tumours, cancer, tumour formation, growth and spread, arteriosclerosis, eye diseases, such as age-induced macular degeneration, choroidal neovascularisation and diabetic retinopathy, inflammatory diseases, arthritis, thrombosis, fibrosis, glomerulonephritis, neurodegeneration, psoriasis, restenosis, wound healing, transplant rejection, metabolic and diseases of the immune system, autoimmune diseases, cirrhosis, diabetes and diseases of the blood vessels.

Assays

The compounds according to the invention described in the examples were tested by the assays described below and were found to have kinase inhibitory activity. Other assays are known from the literature and could readily be performed by the person skilled in the art (see, for example, Dhanabal et al., *Cancer Res.* 59:189-197; Xin et al., *J. Biol. Chem.* 274:9116-9121; Sheu et al., *Anticancer Res.* 18:4435-4441; Ausprunk et al., *Dev. Biol.* 38:237-248; Gimbrone et al., *J. Natl. Cancer Inst.* 52:413-427; Nicosia et al., In *Vitro* 18:538-549).

FAK Kinase Assay (Autophosphorylation)

The focal adhesion kinase (FAK) assay is carried out either as a 384-well flashplate assay (for example for Topcount measurements) or as a 384-well image flashplate assay (for LEADseeker measurements). 2 nM FAK, 400 nM biotinylated substrate (His-TEV-hsFAK (31 686)(K454R)×biotin) and 1 µM ATP (to which 0.25 Ci of 33P-ATP/well has been added) are incubated at 30° C. for 2 hours with or without test compound in a total volume of 50 µl (60 mM Hepes, 10 mM MgCl$_2$, 1.2 mM dithiothreitol, 0.02% of Brij35, 0.1% of BSA, pH 7.5). The reaction is stopped using 25 µl of 200 mM EDTA. After 30 min at 30° C., the liquid is removed, and each well is washed three times with 100 µl of 0.9% sodium chloride solution. Non-specific reaction is determined in the presence of 1 µM EMD 1076893/0(PF-562271). The radioactivity is measured using Topcount (in the case of the use of flashplates) or using LEADseeker (in the case of the use of image flashplates). Results (for example IC50 values) are calculated using, for example, a Symyx Assay Explorer.

Method for the Cellular Testing of FAK Kinase Inhibitors

For analysis of the cellular activity of FAK, the extent of autophosphorylation of FAK at tyrosine 397 is determined with the aid of a Luminex-based assay in the 96-well format. HT29 cells are sown out with 30,000 cells per well in 100 µl of medium (90% of DMEM/10% of FCS) and incubated on the following day for 30 min with a serial dilution of the test substance (7 concentrations) under serum-free conditions. The cells are subsequently lysed using 90 µl of lysis buffer (20 mM tris/HCl pH 8.0, 150 mM NaCl, 1% of NP40, 10% of glycerol, 1% of phosphatase inhibitor II, 20 mM β-glycerol phosphate, 0.1% of protease inhibitor cocktail III, 0.01% of benzonase) per well, and the lysates are separated off from insoluble cell constituents by means of centrifugation through a 96-well filter plate (0.65 µm). The lysates are incubated at 4° C. overnight with shaking with Luminex beads to which an anti-total FAK antibody is coupled. The detection is carried out on the following day by addition of a P-Y397-FAK antibody and a species-specific PE-labelled secondary antibody. P-Y397-FAK is detected by measurement in the Luminex100 instrument by determination of 100 events per cavity in a measurement time of 60 sec. As pharmacological blank, the signals obtained from cells treated with 30 µM of an FAK reference inhibitor are subtracted from all other batches. The control value used for maximum phosphorylation of FAK at Y397 are the signals from cells treated only with the solvent (0.3% of DMSO). The values of the batches treated with test substance are calculated therefrom as percent of control, and IC50 values are determined by means of Assay Explorer.

Test for the Inhibition of PDK1

The experimental batches are carried out in a flashplate system with 384 wells/microtitration plate.

In each case, the PDK1 sample His6-PDK1(Δ1-50)(3.4 nM) ("His$_6$" disclosed as SEQ ID NO: 4), the PDK1 substrate biotin-bA-bA-KTFCGTPEYLAPEVRREPRILSEEEQEM-FRDFDYIADWC (SEQ ID NO: 1) (400 nM), 4 µM ATP (with 0.2 µCi of 33P-ATP/well) and the test substance in 50 µl of conventional experimental solution per well are incubated at 30° C. for 60 min. The test substances are employed in corresponding concentrations (if desired in a dilution series). The control is carried out without test substance. The reaction is stopped using standard methods and washed. The activity of the kinase is measured via the incorporated radioactivity in top count. In order to determine the non-specific kinase reaction (blank value), the experimental batches are carried out in the presence of 100 nM staurosporine.

Evaluation

The radioactivity (decompositions per minute) of the blank value (no use of test substance in the presence of staurosporine) is subtracted from all other radioactivity values. The controls (kinase activity without test substance) are set equal to 100 percent and all other radioactivity values (after subtracting the blank value) are expressed set in relation thereto (for example in % of the control).

Calculation:

$$\frac{100 * \left( \text{value of the kinase activity with test substance} - \text{blank value} \right)}{(\text{value of the control} - \text{blank value})} = \% \text{ of the control}$$

IC$_{50}$ values (50% inhibition) are determined with the aid of statistics programmes, such as, for example, RS1. IC$_{50}$ data of compounds according to the invention are indicated in Table 2.

| Material | Order No. | Manufacturer |
| --- | --- | --- |
| Microtitre plates for cell culture (Nunclon Surface 96-well plate) | 167008 | Nunc |
| DMEM | P04-03550 | Pan Biotech |
| PBS (10x) Dulbecco | 14200-067 | Gibco |
| 96-well plates (polypropylene) | 267334 | Nunc |
| AlamarBlue ™ | BUF012B | Serotec |
| FCS | 1302 | Pan Biotech GmbH |
| Trypsin/EDTA solution 10x | L 2153 | Biochrom AG |
| 75 cm$^2$ culture bottles | 353136 | BD Falcon |
| A2780 | 93112519 | ECACC |
| Colo205 | CCL222 | ATCC |
| MCF7 | HTB22 | ATCC |
| PC3 | CRL-1435 | ATCC |
| 384-well flash plates | SMP410A001PK | Perkin Elmer |

APCI-MS (atmospheric pressure chemical ionisation - mass spectrometry) (M + H)$^+$.

IC$_{50}$ data of compounds according to the invention are indicated in Table 1.

IKKε—Kinase Test (IKKepsilon)

The kinase assay is performed as 384-well flashplate assay. 1 nM IKKε, 800 nM biotinylated IκBα(19-42) peptide (biotin-C6-C6-GLKKERLLDDRHDSGLDSMKDEE (SEQ ID NO: 2)) and 10 µM ATP (with 0.3 µCi of 33P-ATP/well) are incubated in a total volume of 50 µl (10 mM MOPS, 10 mM magnesium acetate, 0.1 mM EGTA, 1 mM dithiothreitol, 0.02% of Brij, 0.1% of BSA, 0.1% of BioStab, pH 7.5) with or without test substance at 30° C. for 120 min. The reaction is stopped using 25 µl of 200 mM EDTA solution, filtered off with suction after 30 min at room temperature, and the wells are 25 washed 3 times with 100 µl of 0.9% NaCl solution. The non-specific proportion of the kinase reaction (blank) is determined using 3 µM EMD 1126352 (BX-795). Radioactivity is measured in the Topcount. IC50 values are calculated using RS1.

TBK1—Kinase Test

The kinase assay is performed as 384-well flashplate assay. 0.6 nM TANK binding kinase (TBK1), 800 nM biotinylated MELK-derived peptide (biotin-Ah-Ah-AKP-KGNKDYHLQTCCGSLAYRRR (SEQ ID NO: 3)) and 10 µM ATP (with 0.25 µCi of 33P-ATP/well) are incubated in a total volume of 50 µl (10 mM MOPS, 10 mM magnesium acetate, 0.1 mM EGTA, 1 mM DTT, 0.02% of Brij35, 0.1% of BSA, pH 7.5) with or without test substance at 30° C. for 120 min. The reaction is stopped using 25 µl of 200 mM EDTA solution, filtered off with suction after 30 min at room temperature, and the wells are washed 3 times with 100 µl of 0.9% NaCl solution. The non-specific proportion of the kinase reaction (blank) is determined using 100 nM staurosporine. Radioactivity is measured in the Topcount. IC50 values are calculated using RS1.

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate, evaporated and purified by chromatography on silica gel and/or by crystallisation. Rf values on silica gel; eluent: ethyl acetate/methanol 9:1.

Mass spectrometry (MS): EI (electron impact ionisation) M+

FAB (fast atom bombardment) (M+H)+

ESI (electrospray ionisation) (M+H)+ (unless indicated otherwise)

EXAMPLE 1

Scheme 1 shows an overview of how the 7-azaindoles according to the invention can be prepared, but pyrrolopyrimidines such as "A14" are also accessible via this route.

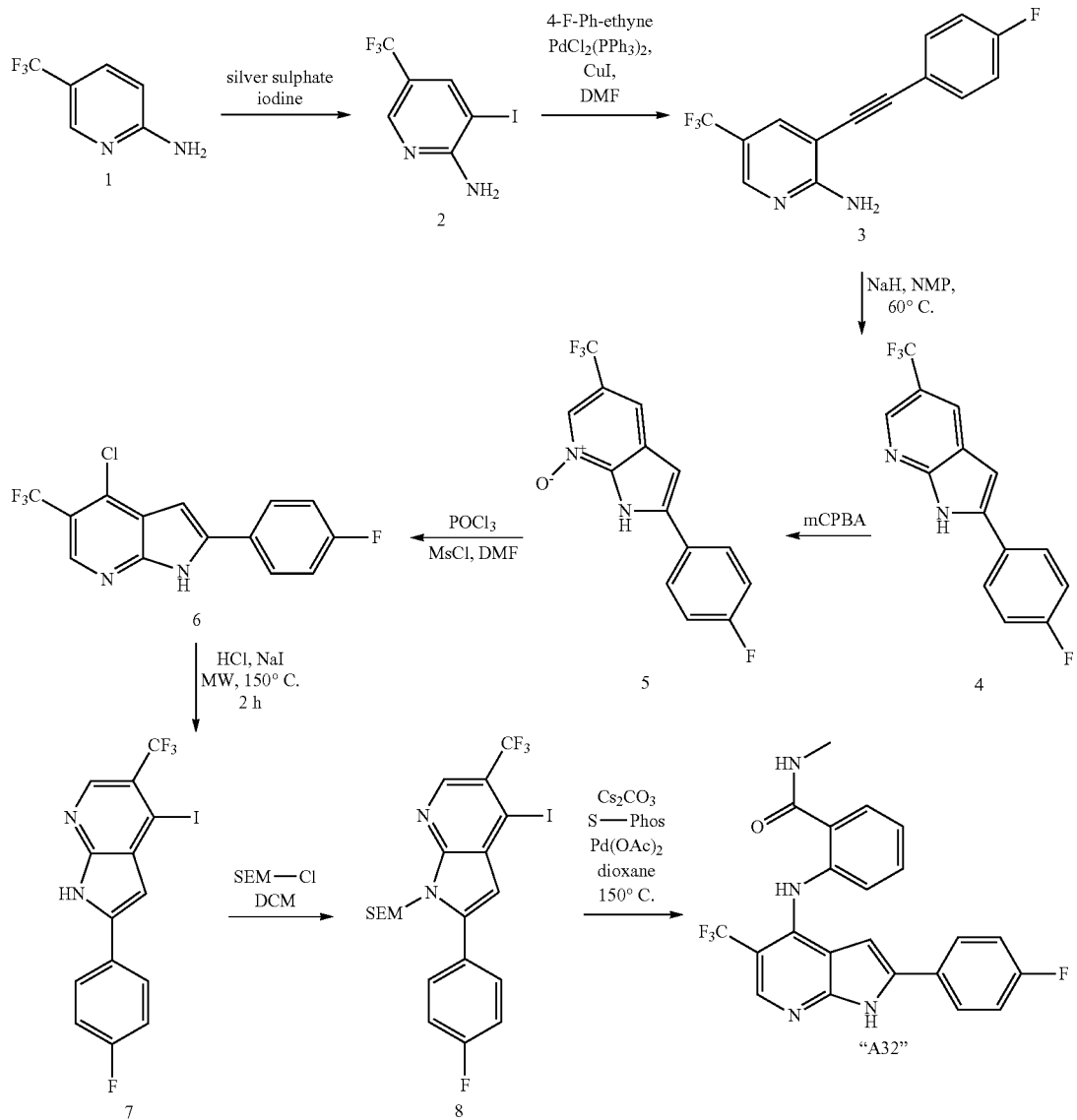

Commercially available 5-trifluoromethyl-2-aminopyridine 1 is iodinated under standard conditions to give 2. This is reacted with 1-ethyne-4-fluorobenzene in a Sonogashira reaction to give 3. The pyrrolopyridine 4 is built up under basic conditions and is oxidised by means of a peracid to give 5. 6 is produced under reductive chlorinating conditions by means of phosphorus oxychloride. After transhalogenation to give 7, the NH function is protected to give 8. Finally, "A32" is obtained under Buchwald conditions.

The sequence can also be carried out with bypassing of intermediate 8, but the yield is then worse.

EXAMPLE 2

The following example describes the sequence with CN instead of $CF_3$ and leaves out intermediates 7 and 8, since direct Buchwald coupling of 6 to give the end product is also possible.

HPLC method: 1__100__2 (instrument: LaChrom)
Column: Chromolith Performance RP18e 100-3 mm
Flow rate: 2 ml/min (pump: L-7100)
Solvent A: water+0.05% of HCOOH
Solvent B: acetonitrile+0.04% of HCOOH
Wavelength: 220 nm (detector: L-7455)
Gradient: 0-0.2 min: 99% of A, 0.2-3.8 min: 99% of A→100% of B, 3.8-4.4 min: 100% of B, 4.4-4.5 min: 100% of B→99% of A, 4.5-5.1 min: 99% of A
LC-MS method: polar.M (instrument: Agilent 1100/1200 series)
Column: Chromolith Speed Rod RP18e-50-4.6
Flow rate: 2.4 ml/min
Solvent A: water+0.05% of HCOOH
Solvent B: acetonitrile+0.04% of HCOOH
WL: 220 nm
Gradient: 0-2.8 min: 4% of B to 100% of B, 2.8-3.3 min: 100% of B Preparation of N-(3-{[5-cyano-2-(4-fluorophenyl)-1H-pyrrolo[2,3-b]pyridin-4-ylamino]methyl}pyridin-2-yl)-N-methylmethanesulfonamide ("A9")

a) Synthesis of 6-amino-5-iodonicotinonitrile

6-Amino-3-pyridinecarbonitrile (10.0 g, 0.081 mol), silver trifluoroacetate (25.5 g, 0.115 mol) and 160 ml of 1,2-dichloroethane are combined in a flask and heated under reflux for 5 h. Iodine (29.5 g, 0.116 mol) is added, and the mixture is heated for a further 18 h. After cooling, the mixture is filtered and partitioned between water and dichloroethane. Organic and aqueous phase are filtered through Celite. The aqueous phase is extracted to exhaustion, and the combined organic phases are combined, dried and evaporated. The residue is dissolved in ethyl acetate and washed with sodium thiosulfate solution. Removal of the solvent gives 6.6 g of yellowish crystals product. These are reacted further without further purification; HPLC: 2.57 min; LCMS: 246 [M+H]$^+$.

b) Synthesis of 6-amino-5-(4-fluorophenylethynyl)nicotinonitrile

The iodine compound prepared above (300 mg), copper(I) iodide (20 mg) and caesium carbonate (1.7 g) are combined in a three-necked flask and dried at 100° C. in vacuo for 1 h. THF (50 ml), 1-ethyne-4-fluorobenzene (250 mg) and Pd(dppf)$_2$Cl$_2$×CH$_2$Cl$_2$ (78 mg) are subsequently added under nitrogen. The batch is stirred at 100° C., during which a black suspension forms. For work-up, the cooled reaction mixture is added to water and subsequently extracted with ethyl acetate. The organic phase is dried and evaporated. The residue is purified by chromatography, giving 220 mg of the title compound. HPLC [Rt] 3.31 min; [M+H]$^+$238.

c) Synthesis of 2-(4-fluorophenyl)-1H-pyrrolo[2,3-b]pyridine-5-carbonitrile

NaH (150 mg) is initially introduced in 5 ml of NMP under nitrogen. The alkyne prepared above (220 mg; dissolved in 5 ml of NMP) is added with stirring and stirred at 60° C. for 12 h. A dark-brown solution forms. The batch is added to water with stirring. A very fine, crystalline precipitate forms, which is dissolved by addition of ethyl acetate. After phase separation, the organic phase is washed with saturated NaCl solution, dried over Na$_2$SO$_4$, filtered off with suction and evaporated to dryness in vacuo. The title compound obtained in this way is reacted further without further purification;

LC-MS: 238 [M+H]$^+$; HPLC: 3.26 (Rt/min).

d) Synthesis of 2-(4-fluorophenyl)-7-oxy-1H-pyrrolo[2,3-b]pyridine-5-carbonitrile The bicyclic compound prepared above (260 mg) is dissolved in 20 ml of ethylene glycol dimethyl ether in an ultrasound bath. 270 mg of m-chloroperbenzoic acid are added, and the mixture is stirred at RT for 4 h. In order to complete the reaction, a further 135 mg of acid are added, and the mixture is stirred at RT for a further 12 h. The reaction mixture is evaporated to dryness in vacuo, water is added (slight cloudiness), and the mixture is then adjusted to pH12 using saturated K$_2$CO$_3$ solution (visible precipitate). The batch is stirred at RT for a further 2 h and then filtered off with suction. The precipitate is dried in vacuo;

yield: 250 mg; LC-MS: 254 [M+H]$^+$; HPLC: 2.77 (Rt/min).

e) Synthesis of 4-chloro-2-(4-fluorophenyl)-1H-pyrrolo[2,3-b]pyridine-5-carbonitrile 250 mg of the N-oxide prepared above are added to 5 ml of phosphoryl chloride and stirred at 80° C. for 2 h. The cooled batch is carefully added to water and, when the POCl$_3$ has reacted, adjusted to pH 13 using NaOH. This phase is then extracted with ethyl acetate. The organic phase is dried over Na$_2$SO$_4$, filtered off with suction and evaporated to dryness in vacuo, giving 210 mg of crude product, which is purified by chromatography, giving 39 mg; HPLC: 3.57 (Rt/min); LC-MS: 272 [M+H]$^+$.

f) Synthesis of "A9"

4-Chloro-2-(4-fluorophenyl)-1H-pyrrolo[2,3-b]pyridine-5-carbonitrile (30 mg, 0.11 mmol), N-(3-aminomethylpyridin-2-yl)-N-methylmethanesulfonamide (159 mg, 0.552 mmol) and N-ethyldiisopropylamine (0.282 ml, 1.656 mmol) are suspended in 0.4 ml of 1-methyl-2-pyrrolidone and heated in a microwave at 170° C. for 40 min. The reaction is still not complete even after a further 40 min, so that a further equivalent of N-(3-aminomethylpyridin-2-yl)-N-methylmethanesulfonamide (31.8 mg, 0.110 mmol) is added, and the batch is heated at 170° C. for a further 60 min. For work-up, the batch is partitioned between water and ethyl acetate, the organic phase is dried (Na$_2$SO$_4$) and evaporated, giving a brown oil, which is purified by chromatography; yield: 17 mg (34%); LC-MS: 451 [M+H]$^+$; HPLC: 3.07 (RT/min).

EXAMPLE 3

Alternative syntheses are shown below:

Scheme 2

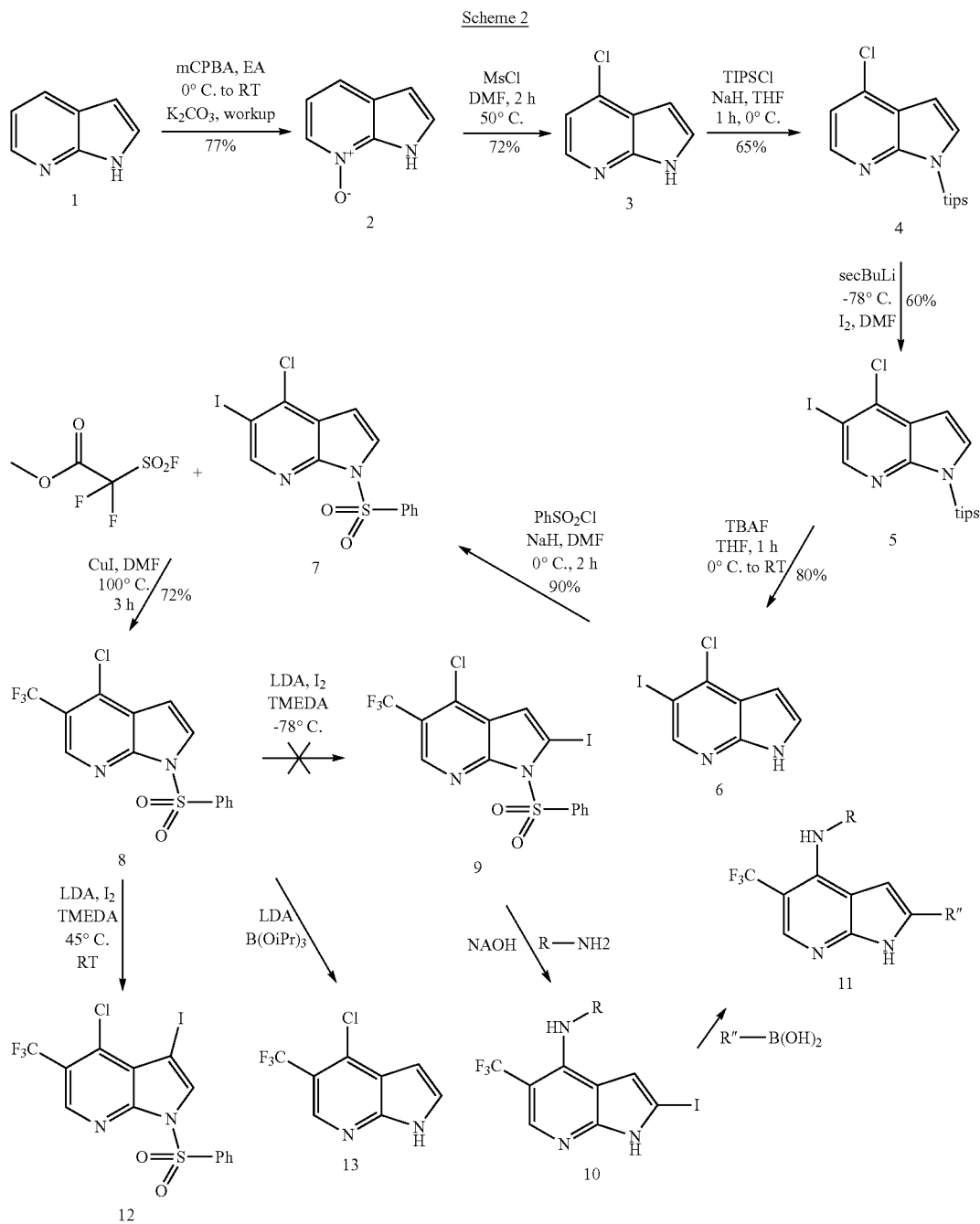

Synthesis of 2 from Scheme 2

144 g of m-CPBA (meta-chloroperbenzoic acid) are added in portions over the course of 10 minutes to a solution of 50 g of 7-azaindole in 1.5 l of ethyl acetate with stirring at 0° C. When the addition is complete, the mixture is stirred at RT for a further 1 h. When the reaction is complete, the solid is filtered off and dissolved in chloroform/methanol=9:1 and neutralised using saturated sodium carbonate solution. After phase separation, the organic phase is dried over sodium sulfate and evaporated, giving the N-oxide with 60% yield (34 g) as colourless solid;

$^1$H NMR 400 MHz, DMSO-$d_6$: δ [ppm] 12.47 (s, 1H), 8.10 (d, J=6.12 Hz, 1H), 7.62 (dd, J=0.80, –7.94 Hz, 1H), 7.44 (d, J=3.28 Hz, 1H), 6.56 (d, J=3.28 Hz, 1H).

Synthesis of 3

32 ml of methanesulfonyl chloride are added dropwise to a solution of 18.5 g of intermediate 2 in 1 l of DMF at 52° C. When the addition is complete, the batch is stirred at 72° C. for a further 2 h. For work-up, the batch is poured onto crushed ice and neutralised using 5N NaOH. The precipitate is filtered off and dried, giving 4-Cl-7-azaindole in 75% yield (16 g) as colourless solid;

LCMS: (method A) 153.0 (M+H), RT. 2.10 min, 93.4% (max), 93.6% (254 nm).

(Method A—0.1% of TFA in $H_2O$, B—0.1% of TFA in ACN: flow—2.0 ml/min.

Column: X Bridge C8 (50×4.6 mm, 3.5 µm)+ve mode);

$^1$H NMR 400 MHz, DMSO-$d_6$: δ [ppm] 12.03 (s, H), 8.16 (d, J=5.12 Hz, H), 7.58 (t, J=3.00 Hz, H), 7.18 (d, J=5.16 Hz, H), 6.49 (dd, J=1.96, 3.44 Hz, H).

Synthesis of 4

5 g of NaH (60% on mineral oil) are added in portions to a solution of 16 g of intermediate 3 in 500 ml of THF at 0° C. When the addition is complete, the mixture is left to stir at the temperature indicated for a further 20 min, and 22.3 g of triisopropylsilyl chloride are added dropwise at this temperature. When the reaction is complete, the mixture is worked up using saturated ammonium chloride solution, diluted with water and extracted with petroleum ether. The crude product obtained is chromatographed on silica gel with petroleum ether, giving product 4 in 92% (30 g) yield as colourless liquid;

LCMS: (method A) 309.2 (M+H), RT. 7.56 min, 93.4% (max);

$^1$H NMR 400 MHz, DMSO-$d_6$: δ [ppm] 8.18 (d, J=5.16 Hz, 1H), 7.59 (d, J=3.80 Hz, 1H), 7.23 (d, J=5.16 Hz, 1H), 6.67 (d, J=3.52 Hz, 1H), 1.82-1.90 (m, 3H), 1.05 (d, J=7.52 Hz, 18H).

Synthesis of 5

53 ml of sec-BuLi are added dropwise over the course of 30 min to a solution of 11 g of intermediate 4 in 250 ml of THF at −78° C. After 1 h, 18 g of iodine are added dropwise over the course of 30 min. While the batch warms to 0° C., a suspension forms. The mixture is worked up using saturated ammonium chloride solution and extracted with ethyl acetate. The combined organic phases are washed with water and saturated NaCL solution and dried over sodium sulfate, giving 5.25 g (53%) of the product 4-chloro-5-iodo-1-triisopropylsilanyl-1 H-pyrrolo[2,3-b]pyridine as colourless solid;

LCMS: (method A) 435.0 (M+H), RT. 7.98 min, 96.9% (max).

$^1$H NMR 400 MHz, DMSO-$d_6$: δ [ppm] 8.52 (s, 1H), 7.57 (d, J=3.52 Hz, 1H), 6.67 (d, J=3.48 Hz, 1H), 1.80-1.88 (m, 3H), 1.04 (d, J=7.52 Hz, 18H).

Synthesis of 6

27 ml of TBAF (tetra-n-butylammonium fluoride; 1M in THF) are added to a solution of 11 g of intermediate 5 in 250 ml of THF at 0° C., and the mixture is stirred for a further 30 min. The solvent is subsequently removed in vacuo, the residue is taken up in ethyl acetate, washed with water and saturated NaCl solution, and the organic phase is dried over sodium sulfate. Evaporation gives product 6 in 99% yield (7 g) as pale-yellow solid;

$^1$H NMR 400 MHz, DMSO-$d_6$: δ [ppm] 12.15 (s, 1H), 8.50 (s, 1H), 7.58 (d, J=3.40 Hz, 1H), 6.49 (d, J=3.44 Hz, 1H), 5.09 (s, 1H);

LCMS: (method A) 279.0 (M+H), RT. 3.97 min, 63.5% (max).

EXAMPLE 4

As can be seen from Scheme 2, the functionalisation of 8 to 9 does not succeed. It is therefore described below how end products are obtained using an alternative protecting-group strategy.

Scheme 3 summarises how end molecules are achieved.

The substituent in position 5 is introduced during the reaction of intermediate 2, shown explicitly here for $CF_3$.

The substituent R in position 2 is introduced during the reaction of intermediate 4 and R' in position 4 is introduced during the reaction of intermediate 6.

Scheme 3

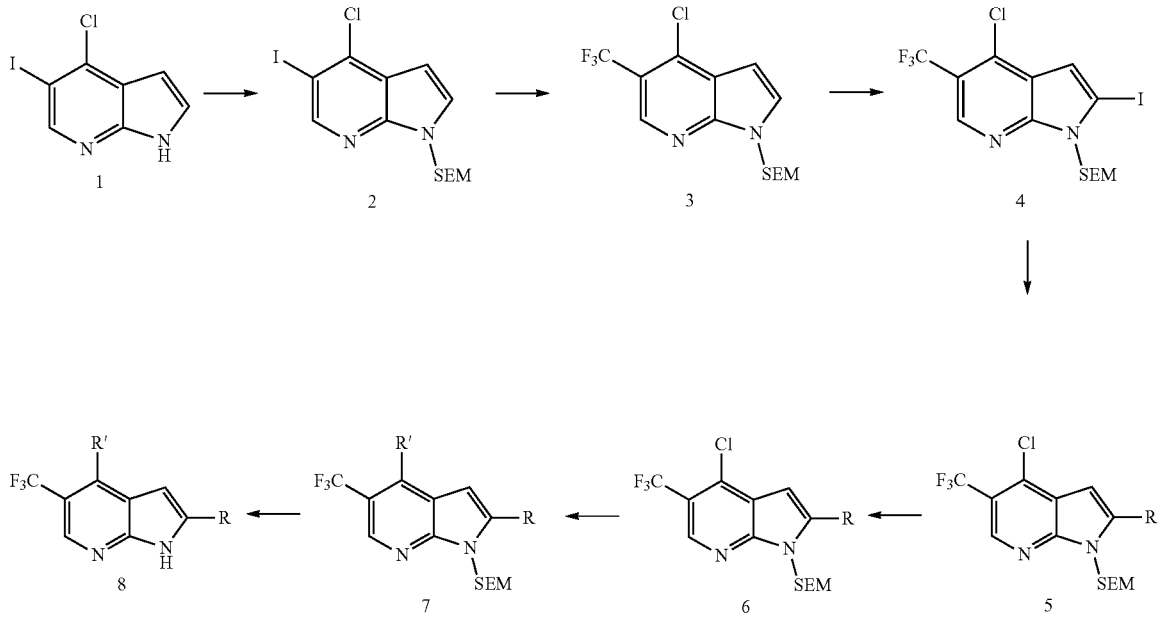

EXAMPLE 5

Preparation of N-methyl-2-[2-(6-morpholin-4-ylpyridin-3-yl)-5-trifluoromethyl-1H-pyrrolo[2,3-b]pyridin-4-ylamino]benzamide ("A33")

LCMS method: A—0.1% of TFA in H₂O, B—0.1% of TFA in ACN: flow—2.0 ml/min.
Column: X Bridge C8 (50×4.6 mm, 3.5 μm)+ve mode.
HPLC method: A—0.1% f TFA in H2O, B—0.1% of TFA in ACN: flow—2.0 ml/min.
Column: XBridge C8 (50×4.6 mm, 3.5 μm).

a) Synthesis of 4-chloro-5-iodo-1-(2-trimethylsilanylethoxymethyl)-1H-pyrrolo[2,3-b]pyridine

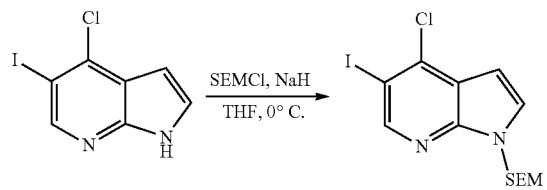 [SMILES: Clc1c(I)cnc2[nH]ccc12 ; C[Si](C)(C)CCOCn1ccc2c(Cl)c(I)cnc21]

7 g of the azaindole 6 from Scheme 2 prepared above are dissolved in 75 ml of THF and cooled to 0° C. 1.2 g of NaH (60% on mineral oil) are added in portions at this temperature, and, after 30 min, stoichiometric amounts of SEMCl are added dropwise over the course of 15 min. When the reaction is complete, the mixture is worked up using aqueous ammonium chloride solution and extracted with ethyl acetate. Washing with water and saturated NaCl solution gives the product in 88% (9 g) yield as yellow oil;
LCMS: (method A) 409.0 (M+H), RT. 6.51 min, 57.4% (max).

b) Synthesis of 4-chloro-5-trifluoromethyl-1-(2-trimethylsilanylethoxymethyl)-1H-pyrrolo[2,3-b]pyridine

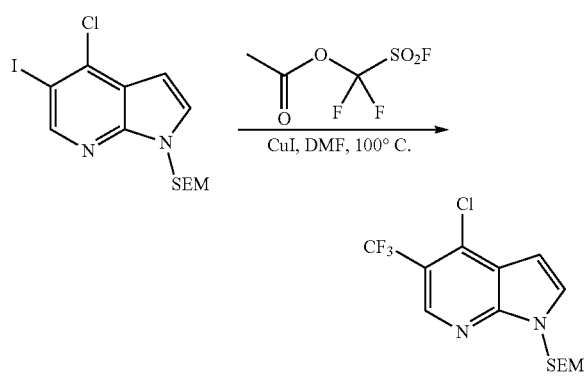

9 g of the starting material prepared above are suspended in 45 ml of DMF together with 4.2 g of copper iodide and 8.5 ml of methyl 2-fluorosulfonyl-difluoroacetate and warmed at 100° C. for 2 h. When the reaction is complete, the copper salt is filtered off, and the residue is extracted with ethyl acetate. The organic extracts are washed with water and saturated NaCl solution and dried over sodium sulfate. The residue obtained after evaporation is purified by chromatography over silica gel, giving 4.6 g (59%) of a colourless solid;
LCMS: (method A) 351.0 (M+H), RT. 6.75 min, 43.3% (max);
¹H NMR 400 MHz, DMSO-d₆: δ [ppm] 8.64 (s, 1H), 7.98 (d, J=3.6 Hz, 1H), 6.78 (d, J=3.64 Hz, 1H), 5.67 (s, 2H), 3.49-3.53 (m, 2H), 0.78-0.82 (m, 2H), −0.14-0.12 (m, 9H).

c) Synthesis of 4-chloro-2-iodo-5-trifluoromethyl-1-(2-trimethylsilanylethoxymethyl)-1 H-pyrrolo[2,3-b]pyridine

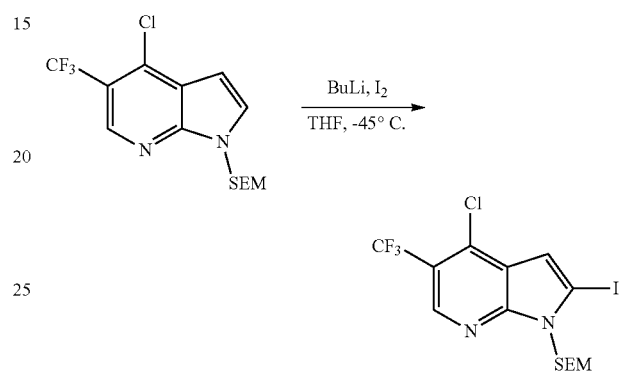

4.6 g of the building block prepared above are dissolved in 50 ml of THF, and stoichiometric amounts of nBuLi are added dropwise with −45° C. After 30 min, a solution of 8.32 g of iodine in 25 ml of THF is added dropwise at the temperature indicated. After slow warming to RT, the mixture is worked up using saturated ammonium chloride solution, and the product is isolated as described above, giving 4 g (64%) of a pale-brown solid; LCMS: (method A) 477.0 (M+H), RT. 7.1 min, 74.6% (max);
¹H NMR 400 MHz, DMSO-d₆: δ [ppm] 8.62 (s, 1H), 7.20 (s, 1H), 5.66 (s, 1H), 3.53 (t, J=7.84 Hz, 2H), 0.81 (t, J=7.9 Hz, 2H), —0.11 (s, 9H).

d) Synthesis of 4-chloro-2-(6-morpholin-4-ylpyridin-3-yl)-5-trifluoromethyl-1-(2-trimethylsilanylethoxymethyl)-1H-pyrrolo[2,3-b]pyridine

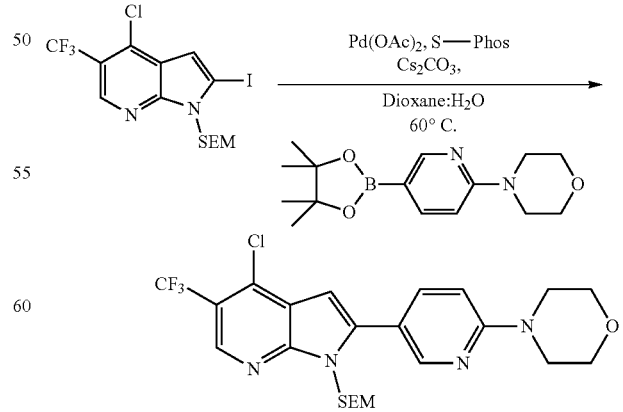

290 mg of pinacolyl 6-(morpholin-4-yl)pyridine-3-boronate, 19 mg of palladium acetate, 34 mg of S-Phos and 800 mg of caesium carbonate are added to 400 mg of the intermediate prepared above in 2.7 ml of dioxane and 0.3 ml of water. The mixture is warmed at 60° C. for 12 h and then worked up at RT using water and ethyl acetate, giving 250 mg (58%) of the title compound as pale-brown oil.

$^{1}$H NMR 400 MHz, DMSO-d$_{6}$: δ [ppm] 8.65 (s, 1H), 8.57 (d, J=2.3 Hz, 1H), 8.00-8.03 (m, 1H), 7.00 (d, J=7.8 Hz, 1H), 6.94 (s, 1H), 5.66 (s, 2H), 3.70-3.72 (m, 4H), 3.56-3.63 (m, 6H), 0.82-0.86 (m, 2H), —0.11 (s, 9H).

e) Synthesis of N-methyl-2-[2-(6-morpholin-4-ylpyridin-3-yl)-5-trifluoromethyl-1-(2-trimethylsilanylethoxymethyl)-1H-pyrrolo[2,3-b]pyridin-4-ylamino]-benzamide

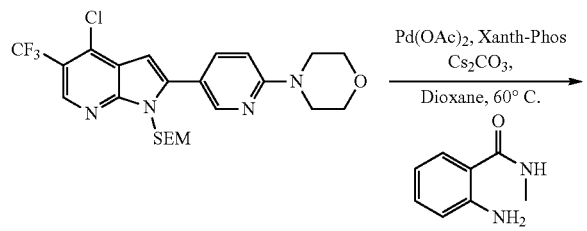

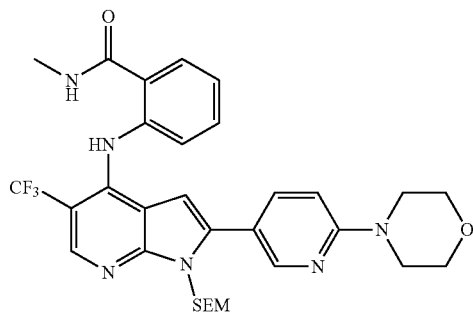

80 mg of the intermediate prepared above, 23 mg of N-methylanthranilamide, 148 mg of caesium carbonate and 18 mg of xanthphos are suspended in 2 ml of degassed dioxane, and 7 mg of palladium acetate are added. The mixture is warmed at 100° C. for 12 h and then subjected to conventional work-up and purification at RT, giving the title compound in 46% yield (45 mg) as yellow oil.

LCMS: (method A) 626.8 (M+H), RT. 5.24 min, 74.7%.

f) Synthesis of the Title Compound "A33"

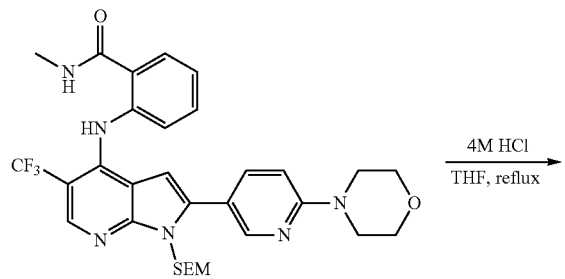

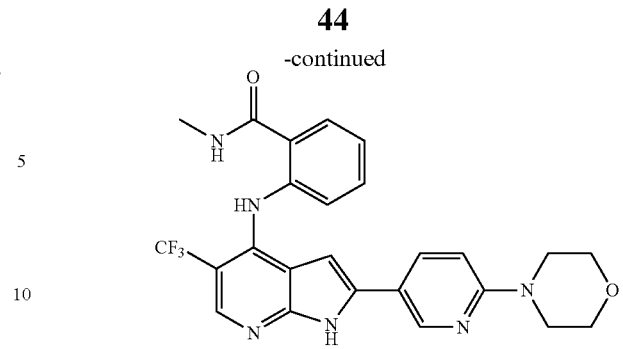

30 mg of the starting material are dissolved in 5 ml of THF, and 0.25 ml of 4N HCl solution is added. The mixture is boiled under reflux for 5 h and evaporated when the reaction is complete. The residue is taken up using ethyl acetate and neutralised sodium carbona solution. The conventional procedure gives 12 mg (65%) of a white solid.

(Analysis see example table)

EXAMPLE 6

5-Azaindoles, such as, for example, "A1"-"A3" from the example table, can be prepared in accordance with the following scheme:

Scheme 4

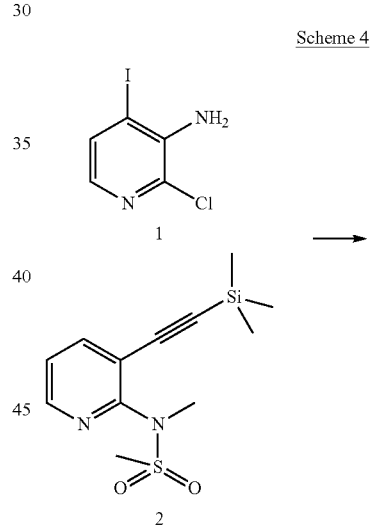

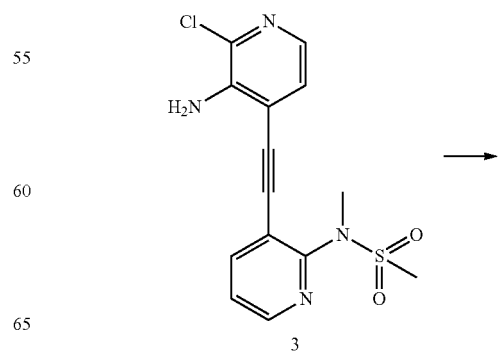

-continued

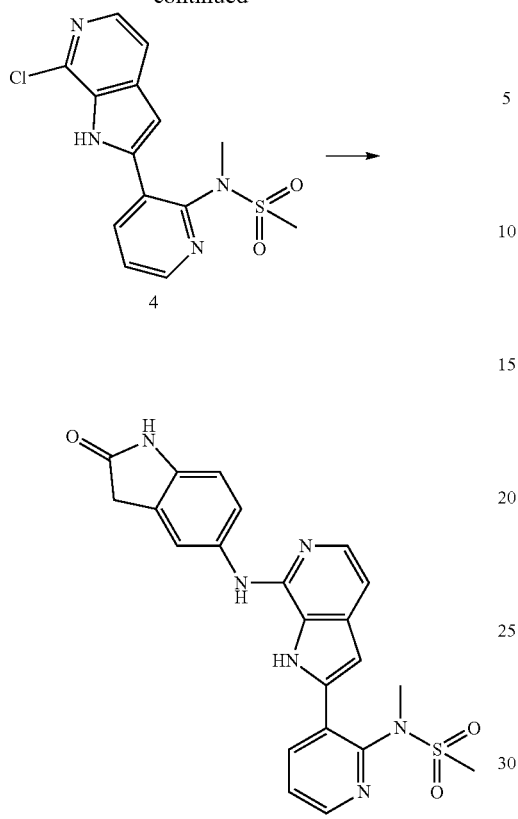

"A1"

a) Starting material 2 (1.8 g) is dissolved in 150 ml of degassed acetonitrile under argon, and 7.8 ml of TBAF (1M in THF) are added for 10 min. Starting material 1 (1.5 g), 1.2 ml of DABCO, 34 mg of copper(I) iodide and 340 mg of tetrakis (triphenylphosphine)palladium(0) are subsequently added. This mixture is stirred at 90° C. for 2 h. After cooling, the solvent is removed in vacuo, the residue is partitioned between ethyl acetate and water, and the organic crude-product fraction finally obtained is purified by chromatography on silica gel, giving 970 mg of a yellowish tacky solid 3; LCMS: 337.0 (M+H), RT. 1.797 min.

b) 920 mg of the solid 3 prepared above are dissolved in 20 ml of THF with sodium tetrachloroaureate dihydrate (54 mg) and stirred at 75° C. for 48 h. The reaction solution cooled to RT is evaporated in vacuo and chromatographed on silica gel with dichloromethane/methanol=95.5, giving 930 mg of a yellowish oil; LCMS: 337.0 (M+H), RT. 1.699 min.

c) Intermediate 4 (125 mg) and 4-aminooxindole (60 mg) are dissolved in 5 ml of ethanol and, after addition of a few drops of 4N HCl in dioxane, heated at 120° C. in a microwave for 1 h, giving, after filtration, 70 mg of the title compound "A1" (analysis in example table).

EXAMPLE 7

Purine derivatives (imidazopyrimidines), such as "A4"-"A6", but also imidazopyridine derivatives, such as "A17" from the example table, are accessible via the sequence shown in Scheme 5.

Scheme 5

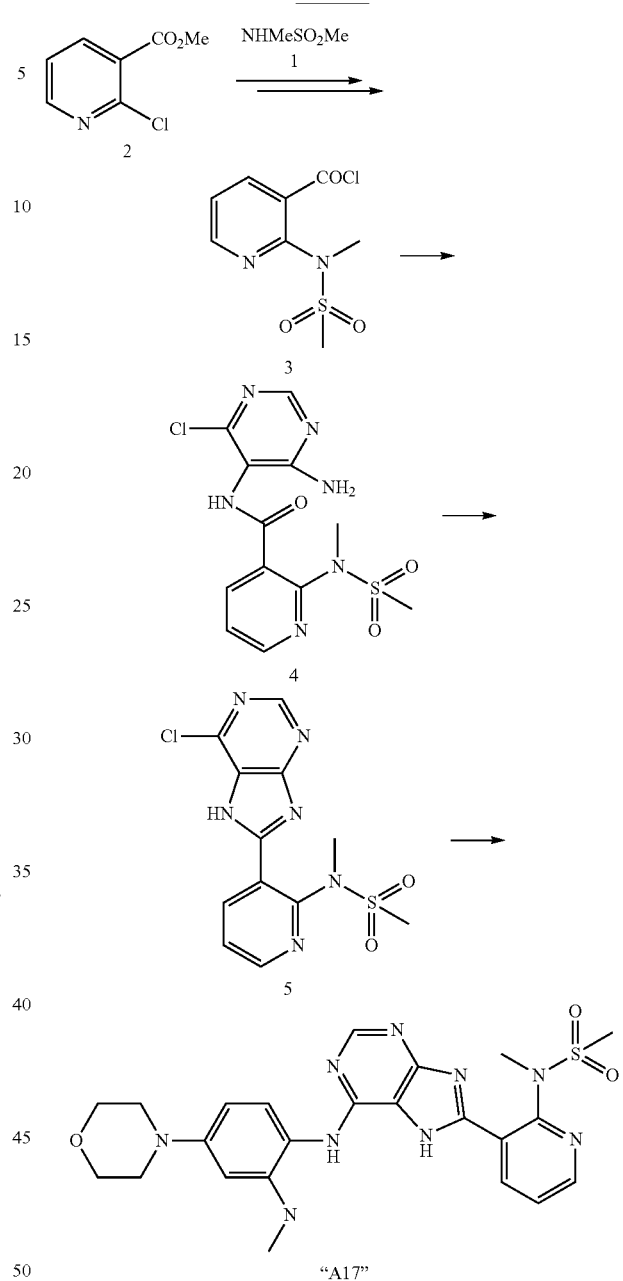

"A17"

a) Methyl 2-chloronicotinate 2 (8.8 g) and methylsulfonyl-methylamine 1 (6.3 g) are dissolved in 180 ml of dry dioxane and degassed using argon. 2.4 g of caesium carbonate, 1.1 g of palladium acetate and 4.3 g of 4,5-bisdiphenylphosphanyl-9,9-dimethyl-9H-xanthene are added to this solution. The reaction is complete after 2 h at 100° C. After conventional work-up, the mixture is chromatographed on silica gel with ethyl acetate/heptane=2:1, giving 9.7 g of a yellow oil that solidifies on storage; LCMS: 245.0 (M+H), RT. 1.315 min.

b) 7.9 g of this intermediate are dissolved in 70 ml of THF and 70 ml of water, and 2.7 g of lithium hydroxide are added. After stirring at RT for 2 h, the reaction is complete and is worked up using 2N HCl solution. The mixture is extracted with ethyl acetate, and drying over sodium sulfate gives a yellow solid, which is immediately reacted further; LCMS: 231.0 (M+H), RT. 1.027 min.

c) 1.6 g of the 2-(N-methylmethylsulfonamide)nicotinic acid obtained in this way are suspended in 10 ml of dichloromethane, and 0.6 ml of thionyl chloride is added dropwise. This suspension is stirred at 40° C. for 3 h, and, immediately after addition of a few drops of DMF, 3 is reacted further with 1 g of 6-chloropyrimidine-4,5-diamine at RT for 16 h. Removal of the solvent gives a 1:3 mixture of 2.3 g of the regioisomers 4, which are immediately reacted further in 30 ml of POCl3 at 50° C. in 48 h to give 5. Chromatography with dichloromethane/methanol=100:0→90:10 gives 810 mg of a colourless solid; LCMS: 339.0 (M+H), RT. 1.341 min.

d) 100 mg of intermediate 5 are dissolved in 5 ml of ethanol together with 70 mg of 2-methoxy-4-morpholin-4-ylphenylamine and, after addition of a few drops of 4N HCl, heated at 120° C. in a microwave for 2 h. The product "A17" is obtained in 32% yield (49 mg) after preparative HPLC purification (analysis see example table).

EXAMPLE 8

Synthesis of 4-(4-fluorophenyl)-2-(piperidin-4-yl)-5-(trifluoromethyl)-1H-pyrrolo[2,3-b]pyridine ("A91")

a) 4-Chloro-2-iodo-5-trifluoromethyl-1-(2-trimethylsilanylethoxymethyl)-1H-pyrrolo[2,3-b]pyridine (476 mg), tert-butyl 4-(4,4,5,5-tetramethyl-1,3-dioxaborolan-2-yl)-5,6-dihydropyridine-1(2H)-carboxylate (311 mg), bis(di-tert-butyl-(4-dimethylaminophenyl)phosphine)palladium (II) dichloride (14 mg) and caesium carbonate (954 mg) are combined in a flask and suspended in 4.5 ml of dioxane and 0.5 ml of water. This mixture is warmed at 60° C. for 12 h. After cooling to RT, the mixture is diluted with 10 ml of water and extracted to exhaustion with ethyl acetate. The mixture is subjected to conventional work-up, giving 325 mg (61%) of tert-butyl 4-(4-chloro-5-(trifluoromethyl)-1-((2-(trimethylsilyl)ethoxy)methyl)-1H-pyrrolo[2,3-b]pyridin-2-yl)-5,6-dihydropyridine-1(2H)-carboxylate as yellowish foam;

$^1$H NMR 400 MHz, DMSO-d$_6$: δ [ppm] 8.69 (s, 1H), 7.43-7.47 (m, 2H), 7.37 (t, J=8.88 Hz, 2H), 6.40 (s, 1H), 6.23 (s, 1H), 5.70 (s, 1H), 4.04 (s, 2H), 3.66 (t, J=8.08 Hz, 2H), 3.50 (m, 2H), 2.45 (m, 2H), 1.41 (s, 9H).

b) The intermediate prepared above (265 mg), (4-fluorophenyl)boronic acid (84 mg), bis(di-tert-butyl(4-dimethylaminophenyl)phosphine) palladium(II) dichloride (7 mg) and caesium carbonate (477 mg) are suspended in dioxane (2.7 ml)/water (0.3 ml) and stirred at 60° C. for 12 h. The mixture is subjected to conventional work-up, giving 165 mg (56%) of tert-butyl 4-(4-(4-fluorophenyl)-5-(trifluoromethyl)-1-((2-(trimethylsilyl)ethoxy)methyl)-1H-pyrrolo[2,3-b]pyridin-2-yl)-5,6-dihydropyridine-1(2H)-carboxylate as yellowish foam.

LCMS: (method A) 594.2 (M+H), RT. 7.722 min, 65.9% (max), 72.6% (254 nm).

c) The intermediate prepared above (160 mg) is dissolved in dry methanol (10 ml), and 10% palladium on active carbon (40 mg) are added. The flask is sealed with a hydrogen balloon and stirred for 1 h. Insoluble constituents are subsequently filtered off, and, after evaporation, crude tert-butyl 4-(4-(4-fluorophenyl)-5-(trifluoromethyl)-1-((2-(trimethylsilyl)ethoxy)methyl)-1H-pyrrolo[2,3-b]pyridin-2-yl)piperidine-1-carboxylate is immediately reacted further. To this end, 80 mg are taken up in 2 ml of 4N HCl solution in dioxane and warmed at 60° C. for 5 h. Conventional work-up and careful purification gives the title compound "A91" as colourless solid.

EXAMPLE 9

Synthesis of 2-(3-methoxyphenyl)-4-(1-methyl-1H-pyrazol-4-yl)-5-(trifluoromethyl)-1H-pyrrolo[2,3-b]pyridine ("A88")

a) As described under Example 8a), 4-chloro-2-iodo-5-trifluoromethyl-1-(2-trimethylsilanylethoxymethyl)-1H-pyrrolo[2,3-b]pyridine (476 mg), 3-methoxyphenylboronic acid (152 mg), bis(di-tert-butyl(4-dimethylaminophenyl)phosphine)palladium (II) dichloride (14 mg) and caesium carbonate (954 mg) are used, giving 275 mg (60%) of 4-chloro-2-(3-methoxyphenyl)-5-(trifluoromethyl)-1-((2-(trimethylsilyl)ethoxy)methyl)-1H-pyrrolo[2,3-b]pyridine as colourless solid;

LCMS: (method A) 457.0 (M+H), RT. 7.94 min, 94.8% (max), 96.2% (254 nm).

b) As described under Example 8b), 4-chloro-2-(3-methoxyphenyl)-5-(trifluoromethyl)-1-((2-(trimethylsilyl)ethoxy)methyl)-1H-pyrrolo[2,3-b]pyridine (228 mg), 1-methylpyrazole-4-boronic acid (75 mg), bis(di-tert-butyl-(4-dimethylaminophenyl)phosphine)palladium (II) dichloride (7 mg) and caesium carbonate (477 mg) are used, giving 2-(3-methoxyphenyl)-4-(1-methyl-1H-pyrazol-4-yl)-5-(trifluoromethyl)-1-((2-(trimethylsilyl)ethoxy)methyl)-1H-pyrrolo[2,3-b]pyridine as pale-yellow solid in 9% yield (48 mg);

LCMS: (method A) 503.0 (M+H), RT. 6.733 min, 86.5% (max), 90.4% (254 nm).

c) As described in the second part of Example 8c), 90 mg of the intermediate prepared under Example 9b) are used here, giving the title compound "A88" as colourless solid in 9.8% (6.4 mg) yield.

EXAMPLE 10

Synthesis of 2-((2-(4-fluorophenyl)-5-(trifluoromethyl)-1H-pyrrolo[2,3-b]pyridin-4-yl)oxy)benzonitrile ("A93")

a) A solution of 2-hydroxybenzonitirile (179 mg) and potassium carbonate (415 mg) in 5 ml of DMSO is warmed at 100° C. for 15 min., and 4-chloro-2-(4-fluorophenyl)-5-(trifluoromethyl)-1-((2-(trimethylsilyl)ethoxy)methyl)-1H-pyrrolo[2,3-b]pyridine (444 mg) is then added. The mixture is stirred at the temperature indicated for a further 12 h, and 20 ml of water are added for work-up. The mixture is extracted with ethyl acetate and dried using saturated NaCl solution and sodium sulfate. Chromatography on silica gel gives 57 mg (11%) of 2-((2-(4-fluorophenyl)-5-(trifluoromethyl)-1-((2-(trimethylsilyl)ethoxy)methyl)-1H-pyrrolo[2,3-b]pyridin-4-yl)oxy)benzonitrile as brownish solid;

LCMS: (method A) 528.3 (M+H), RT. 7.124 min, 93.2% (max), 76.6% (254 nm).

b) As described in the second part of Example 8c), 52 mg of the intermediate prepared under Example 10a) are used here, giving the title compound "A93" as colourless solid.

EXAMPLE 11

Synthesis of N-(2-((2-(4-fluorophenyl)-5-(trifluoromethyl)-1H-pyrrolo[2,3-b]-pyridin-4-yl)ethynyl)phenyl)-N-methylmethanesulfonamide ("A27")

CuI (19 mg), Pd(OAc)$_2$ (22 mg) and Cs$_2$CO$_3$ (1.27 g) are added to a degassed solution of 4-chloro-2-(4-fluorophenyl)-5-(trifluoromethyl)-1H-pyrrolo[2,3-b]-pyridine (628 mg), N-(2-ethynylphenyl)-N-methylmethanesulfonamide (450 mg) in 1,4-dioxane (10 ml), and the mixture is stirred at 100° C. for 5 h. Conventional work-up and purification gives the title compound in 70% yield (663 mg).

EXAMPLE 12

Synthesis of N-(2-(2-(2-(4-fluorophenyl)-5-(trifluoromethyl)-1H-pyrrolo[2,3-b]-pyridin-4-yl)ethyl)phenyl)-N-methylmethanesulfonamide ("A28")

The compound prepared in accordance with Example 11 (50 mg) is passed over a palladium cartridge in an H-Cube with 20 ml of dry methanol at a pressure of 40 kg and a flow rate of 20 ml/h. Purification gives the title compound in 65% yield (37 mg).

The following compounds are obtained analogously to the examples indicated

| No. | Structure/name | $^1$H NMR (400 MHz, DMSO-d$_6$) δ [ppm] J [Hz] | LC-MS; rt; [M + H]$^+$ |
|---|---|---|---|
| "A1" | N-Methyl-N-{3-[7-(2-oxo-2,3-dihydro-1H-indol-5-ylamino)-1H-pyrrolo-[2,3-c]pyridin-2-yl]-pyridin-2-yl}methanesulfonamide | 12.32 (br. s, 1H), 11.23 (br. s, 1H), 10.60 (s, 1H), 8.63-8.58 (m 2H), 7.71-7.68 (m, 1H), 7.41 (s, 1H), 7.36-7.33 (m, 2H), 7.28-7.24 (m, 2H), 6.97 (d, 1H), 3.58 (s, 2H), 3.24 (s, 3H), 3.21 (s, 3H). | 2.999 min [449.0] |
| "A2" | N-Methyl-N-{3-[7-(4-morpholin-4-ylphenylamino)-1H-pyrrolo[2,3-c]pyridin-2-yl]pyridin-2-yl}methanesulfonamide | 13.44 (br. s, 1H), 12.02 (br. s, 1H), 10.77 (br. s, 1H), 8.63-8.61 (m, 1H), 8.54 (d, 1H), 7.70-7.67 (m, 1H), 7.32-7.23 (m, 4H), 6.78 (d, 1H), 6.68-6.65 (m, 1H), 3.80 (s, 3H), 3.77 (s, 3H), 3.25-3.23 (m, 8H). | 3.306 min [509.2] |
| "A3" | N-Methyl-N-{3-[7-(2-oxo-1,2,3,4-tetrahydroquinolin-6-ylamino)-1H-pyrrolo[2,3-c]pyridin-2-yl]pyridin-2-yl}methanesulfonamide | 13.54 (br. s, 1H), 12.40 (br. s, 1H), 11.20 (br. s, 1H), 10.30 (s, 1H), 8.62 (dd, 1H), 8.57 (dd, 1H), 7.69 (dd, 1H), 7.37-7.24 (m, 5H), 7.01 (d, 1H), 3.24 (s, 3H), 3.22 (s, 3H), 2.97-2.93 (m, 2H). | 3.070 min [463.2] |
| "A4" | N-{3-[6-(2-Methoxy-4-morpholin-4-ylphenylamino)-7H-purin-8-yl]pyridin-2-yl}-N-methylmethanesulfonamide | 13.21 (br. s, 1H), 8.66 (dd, 1H), 8.41 (br. d, 2H), 8.32 (s, 1H), 8.01 (br. s, 1H), 7.63 (dd, 1H), 6.70 (d, 1H), 6.56 (dd, 1H), 3.86 (s, 3H), 3.76 (s, 3H), 3.17-3.12 (m, 8H), 3.03 (s, 3H). | 2.721 min [511.2] |

-continued

| No. | Structure/name | $^1$H NMR (400 MHz, DMSO-$d_6$) δ [ppm] J [Hz] | LC-MS; rt; [M + H]$^+$ |
|---|---|---|---|
| "A5" | 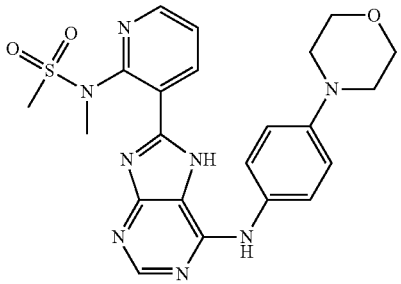 [SMILES: CN(c1ncccc1-c1nc2ncnc(Nc3ccc(N4CCOCC4)cc3)c2[nH]1)S(C)(=O)=O]<br>N-Methyl-N-{3-[6-(4-morpholin-4-ylphenyl-amino)-7H-purin-8-yl]pyridin-2-yl}methanesulfonamide | | 2.646 min [481.2] |
| "A6" | 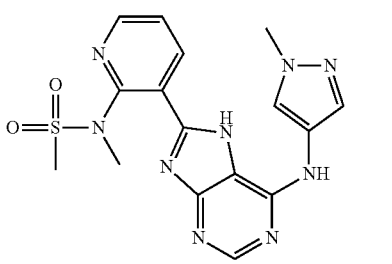 [SMILES: CN(c1ncccc1-c1nc2ncnc(Nc3cnn(C)c3)c2[nH]1)S(C)(=O)=O]<br>N-Methyl-N-{3-[6-(1-methyl-1H-pyrazol-4-yl-amino)-7H-purin-8-yl]pyridin-2-yl}methanesulfonamide | 13.20 (br. s, 1H), 8.73 (dd, 1H), 8.69 (br. s, 1H), 8.41 (dd, 1H), 8.18 (s, 1H), 7.76 (s, 1H), 7.68 (dd, 1H), 3.89 (s, 3H), 3.42 (s, 3H), 3.02 (s, 3H). | 2.258 min [400.2] |
| "A7" | 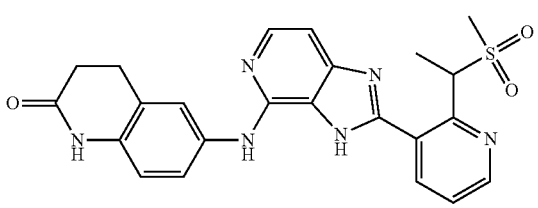 [SMILES: CC(c1ncccc1-c1nc2ccnc(Nc3ccc4c(c3)CCC(=O)N4)c2[nH]1)S(C)(=O)=O]<br>N-Methyl-N-{3-[4-(2-oxo-1,2,3,4-tetra-hydroquinolin-6-ylamino)-3H-imidazo[4,5-c]-pyridin-2-yl]pyridin-2-yl}methanesulfonamide | 13.41 (br. s, 1H), 12.59 (br. s, 1H), 10.27 (br. s, 1H), 8.72 (dd, 1H), 8.48 (dd, 1H), 7.69 (dd, 1H), 7.62 (d, 1H), 7.40 (s, 1H), 7.33 (d, 1H), 7.26 (d, 1H), 6.97 (d, 1H), 3.41 (s, 3H), 3.40-3.36 (m, 2H), 3.04 (s, 3H), 2.94-2.91 (m, 2H). | 2.685 min [464.2] |
| "A9" | 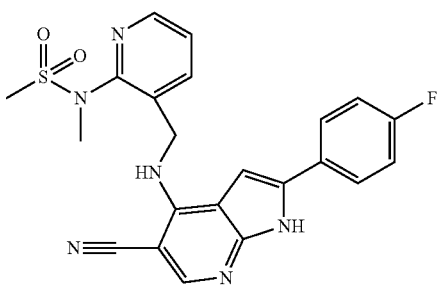 [SMILES: CN(c1ncccc1CNc1c(C#N)cnc2[nH]c(-c3ccc(F)cc3)cc12)S(C)(=O)=O]<br>N-(3-{[5-Cyano-2-(4-fluorophenyl)-1H-pyrrolo-[2,3-b]pyridin-4-ylamino]methyl}pyridin-2-yl)-N-methylmethanesulfonamide | 12.35 (s, 1H), 8.45 (dd, J = 4.7, 1.7, 1H), 8.12 (s, 1H), 7.80-7.68 (m, 4H), 7.40 (dd, J = 7.8, 4.7, 1H), 7.26 (t, J = 8.9, 2H), 6.90 (d, J = 2.1, 1H), 5.06 (d, J = 6.6, 2H), 3.24 (s, 3H), 3.19 (s, 3H). | 2.152 min [451.1] |

-continued

| No. | Structure/name | $^1$H NMR (400 MHz, DMSO-d$_6$) δ [ppm] J [Hz] | LC-MS; rt; [M + H]$^+$ |
|---|---|---|---|
| "A10" | N-{3-[(3-Chloro-5-cyano-1H-pyrrolo[2,3-b]-pyridin-4-ylamino)methyl]pyridin-2-yl}-N-methylmethanesulfonamide | 12.19 (s, 1H), 8.46 (dd, J = 4.7, 1.8, 1H), 8.05 (s, 1H), 7.77 (dd, J = 7.7, 1.8, 1H), 7.53-7.37 (m, 2H), 7.29 (t, J = 6.7, 1H), 5.14 (d, J = 6.7, 2H), 3.11 (s, 3H). | 1.785 min [391.2] |
| "A11" | N-{3-[(5-Cyano-2-phenyl-1H-pyrrolo[2,3-b]-pyridin-4-ylamino)methyl]pyridin-2-yl}-N-methylmethanesulfonamide | 300 MHz; 12.33 (br. S, 1H); 8.45 (dd, 1H); 8.11 (s, 1H); 7.71-7.78 (m, 3H); 7.70 (t, 1H); 7.42 (dd, 1H); 7.36-7.47 (m, 2H); 7.24-7.34 (m, 1H); 6.94 (s, 1H); 5.07 (d, 2H); 3.25 (s, 3H), 3.19 (s, 3H). | 6.88 min$^\$$ [433.09] |
| "A12" | N-{3-[(5-Cyano-1H-pyrrolo[2,3-b]pyridin-4-ylamino)methyl]pyridin-2-yl}-N-methylmethanesulfonamide | 400 MHz; 11.84 (s, 1H), 8.45 (dd, J = 4.7, 1.8, 1H), 8.08 (s, 1H), 7.77-7.67 (m, 2H), 7.40 (dd, J = 7.7, 4.7, 1H), 7.23-7.15 (m, 1H), 6.56-6.47 (m, 1H), 5.01 (d, J = 6.6, 2H), 3.25 (s, 3H), 3.16 (s, 3H). | 1.617 min [357.1] |
| "A13" | N-Methyl-N-{3-[(5-methyl-1H-pyrrolo[2,3-b]-pyridin-4-ylamino)methyl]pyridin-2-yl}-methanesulfonamide | 300 MHz; 13.56 (br. S, 1H); 12.05 (br. S, 1H); 8.48 (dd, 1H); 7.90 (s, 1H); 7.78-7.89 (m, 1H); 7.71 (dd, 1H); 7.39 (dd, 1H); 7.18 (d, 1H); 6.37 (d, 1H); 4.97-5.11 (m, 2H); 3.27 (s, 3H); 3.19 (s, 3H); 2.27 (s, 3H). | 6.52 min$^\$$ [346.08] |

-continued

| No. | Structure/name | $^1$H NMR (400 MHz, DMSO-d$_6$) δ [ppm] J [Hz] | LC-MS; rt; [M + H]$^+$ |
|---|---|---|---|
| "A14" | 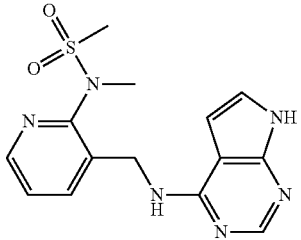 [SMILES: CN(c1ncccc1CNc1ncnc2[nH]ccc12)S(C)(=O)=O]<br>N-Methyl-N-{3-[(7H-pyrrolo[2,3-d]pyrimidin-4-ylamino)methyl]pyridin-2-yl}methanesulfonamide | 300 MHz; 11.52 (br. S, 1H); 8.41 (dd, 1H); 8.07 (s, 1H); 7.91 (t, 1H); 7.80 (dd, 1H); 7.38 (dd, 1H); 7.10 (dd, 1H); 6.57 (d, 1H); 4.82 (d, 2H); 3.25 (s, 3H); 3.15 (s, 3H). | 4.71 min$^\$$ [333.1] |
| "A15" | 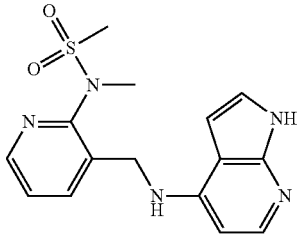 [SMILES: CN(c1ncccc1CNc1ccnc2[nH]ccc12)S(C)(=O)=O]<br>N-Methyl-N-{3-[(1H-pyrrolo[2,3-b]pyridin-4-yl-amino)methyl]pyridin-2-yl}methanesulfonamide | 300 MHz; 11.15 (br. S, 1H); 8.42 (dd, 1H); 7.73-7.80 (m, 1H); 7.73 (d, 1H); 7.38 (dd, 1H); 7.19 (t, 1H); 7.10 (d, 1H); 6.58 (d, 1H); 5.93 (d, 1H); 4.61 (d, 2H); 3.25 (s, 3H); 3.17 (s, 3H). | 6.03 min$^\$$ [332.12] |
| "A16" | 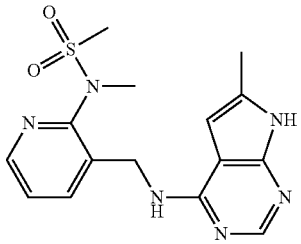 [SMILES: Cc1cc2c(NCc3cccnc3N(C)S(C)(=O)=O)ncnc2[nH]1]<br>N-Methyl-N-{3-[(6-methyl-7H-pyrrolo[2,3-d]-pyrimidin-4-ylamino)methyl]pyridin-2-yl}-methanesulfonamide x TFA | 300 MHz; 12.24 (br. s, 1H); 8.92 (br. s, 1H); 8.49 (dd, 1H); 8.25 (s, 1H); 7.85 (dd, 1H); 7.45 (dd, 1H); 6.45 (br. s, 1H); 4.88 (d, 2H); 3.22 (s, 3H); 3.15 (s, 3H); 2.36 (s. 3H). | 6.48 min$^\$$ [347.12] |
| "A17" | 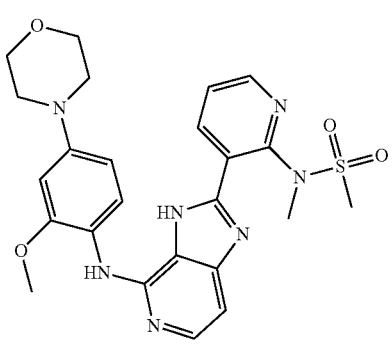 [SMILES: COc1cc(N2CCOCC2)ccc1Nc1nccc2nc(-c3cccnc3N(C)S(C)(=O)=O)[nH]c12]<br>N-{3-[4-(2-Methoxy-4-morpholin-4-ylphenyl-amino)-3H-imidazo[4,5-c]pyridin-2-yl]pyridin-2-yl}-N-methylmethanesulfonamide | 12.65 (br. s, 1H), 8.66 (m, 1H), 8.65 (m, 1H), 8.60 (m, 1H), 7.94 (s, 1H), 7.89 (m, 1H), 7.64 (m, 1H), 7.03 (d, 1H), 6.71 (d, 1H), 6.54 (m, 1H), 3.93 (s, 3H), 3.76 (m, 4H), 3.36 (m, 7H); 3.08 (m, 3H). | 3.057 min [510.2]$^\&$ |
| "A18" | 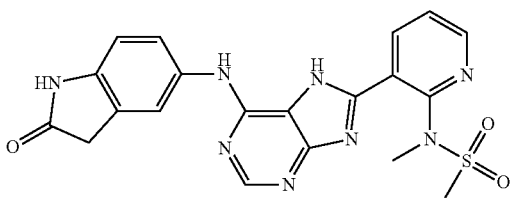 [SMILES: CN(c1ncccc1-c1nc2ncnc(Nc3ccc4c(c3)CC(=O)N4)c2[nH]1)S(C)(=O)=O]<br>N-Methyl-N-{3-[6-(2-oxo-2,3-dihydro-1H-indol-5-ylamino)-7H-purin-8-yl]pyridin-2-yl}-methanesulfonamide | 11.40 (br. s, 1H); 10.48 (s, 1H); 8.73 (m, 1H); 8.61 (br. s, 1H); 8.42 (m, 1H); 7.78 (s, 1H); 7.69 (m, 1H); 7.62 (d, 1H); 6.88 (d, 1H); 3.41 (s, 3H); 3.03 (s, 3H). | 2.366 min [451.2] |

-continued

| No. | Structure/name | ¹H NMR (400 MHz, DMSO-d$_6$) δ [ppm] J [Hz] | LC-MS; rt; [M + H]⁺ |
|---|---|---|---|
| "A19" | 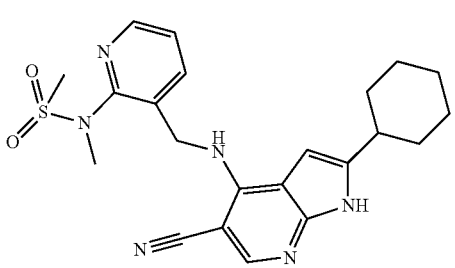 [SMILES: CN(c1ncccc1CNc1c(C#N)cnc2[nH]c(C3CCCCC3)cc12)S(C)(=O)=O]<br>N-{3-[(5-Cyano-2-cyclohexyl-1H-pyrrolo[2,3-b]-pyridin-4-ylamino)methyl]pyridin-2-yl}-N-methylmethanesulfonamide | 11.68 (s, 1H), 8.44 (m, 1H), 7.98 (s, 1H), 7.67 (m, 1H), 7.52 (m, 1H), 7.38 (m, 1H), 6.19 (s, 1H), 4.96 (m, 2H), 3.23 (s, 3H), 3.14 (s, 3H), 2.56 (m, 1H), 1.98 (m, 2H), 1.64 (m, 3H), 1.16 (m, 5H). | 1.03 min [439.23]%6 |
| "A20" | 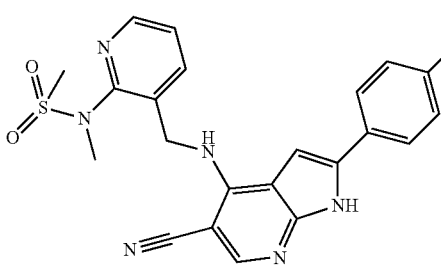<br>N-(3-{[2-(4-Butylphenyl)-5-cyano-1H-pyrrolo-[2,3-b]pyridin-4-ylamino]methyl}pyridin-2-yl)-N-methylmethanesulfonamide | 12.28 (s, 1H), 8.44 (m, 1H), 8.09 (s, 1H), 7.69 (m, 2H), 7.63 (m 2H), 7.3 (m, 1H), 7.21 (m, 2H), 6.87 (s, 1H), 5.04 (m, 2H), 3.23 (s, 3H), 3.19 (s, 3H), 2.55 (m, 2H), 1.51 (m, 2H), 1.29 (m, 2H), 0.84 (t, 3H). | 4.11 min [489.23]%6 |
| "A21" | 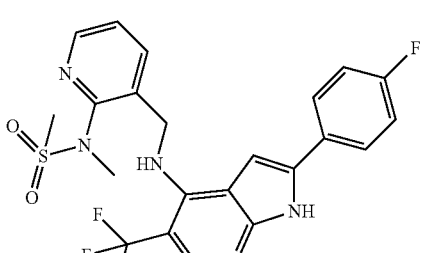<br>N-(3-{[2-(4-Fluorophenyl)-5-trifluoromethyl-1H-pyrrolo[2,3-b]pyridin-4-ylamino]methyl}pyridin-2-yl)-N-methylmethanesulfonamide | 12.19 (s, 1H), 8.42 (dd, J = 4.7, 1.8, 1H), 8.13 (s, 1H), 7.75-7.66 (m, 3H), 7.39 (dd, J = 7.8, 4.7, 1H), 7.21 (t, J = 8.9, 2H), 6.88 (t, J = 6.6, 1H), 6.72 (d, J = 2.2, 1H), 5.08 (d, J = 6.3, 2H), 3.23 (s, 3H), 3.22 (s, 3H). | 3.894 min [494.0] |
| "A22" | 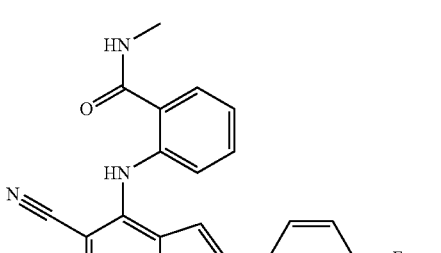<br>2-[[5-Cyano-2-(4-fluorophenyl)-1H-pyrrolo-[2,3-b]pyridin-4-yl]amino]-N-methylbenzamide | 12.61 (s, 1H), 10.47 (s, 1H), 8.70 (d, J = 4.7, 1H), 8.39 (s, 1H), 7.81-7.75 (m, 2H), 7.73 (dd, J = 7.9, 1.4, 1H), 7.50-7.44 (m, 1H), 7.27 (dd, J = 16.1, 8.0, 3H), 7.18 (t, J = 7.6, 1H), 6.27 (d, J = 2.2, 1H), 2.79 (d, J = 4.6, 3H). | 3.736 min [386.3] |

-continued

| No. | Structure/name | $^1$H NMR (400 MHz, DMSO-d$_6$) δ [ppm] J [Hz] | LC-MS; rt; [M + H]$^+$ |
|---|---|---|---|
| "A23" | N-(3-{[5-Cyano-2-(2-methylpyridin-4-yl)-1H-pyrrolo[2,3-b]pyridin-4-ylamino]methyl}pyridin-2-yl)-N-methylmethanesulfonamide | 12.55 (s, 1H), 8.45 (dd, J = 4.7, 1.8, 1H), 8.42 (d, J = 5.2, 1H), 8.16 (s, 1H), 7.86 (s, 1H), 7.71 (d, J = 7.8, 1H), 7.58 (s, 1H), 7.49 (d, J = 5.2, 1H), 7.40 (dd, J = 7.8, 4.7, 1H), 7.16 (s, 1H), 5.06 (d, J = 6.5, 2H), 3.23 (s, 3H), 3.21 (s, 3H), 2.45 (s, 3H). | 2.419 min [448.0] |
| "A24" | N-(3-{[2-(4-Fluorophenyl)-5-methyl-1H-pyrrolo-[2,3-b]pyridin-4-ylamino]methyl}pyridin-2-yl)-N-methylmethanesulfonamide | 11.56 (s, 1H), 8.40 (d, J = 2.9, 1H), 7.73 (d, J = 6.2, 1H), 7.69 (dd, J = 9.0, 5.6, 3H), 7.36 (dd, J = 7.7, 4.7, 1H), 7.18 (t, J = 8.9, 2H), 6.57 (s, 1H), 6.28 (s, 1H), 4.99 (d, J = 6.5, 2H), 3.22 (s, 3H), 3.22 (s, 3H), 2.17 (s, 3H). | 3.597 min [440.0] |
| "A25" | N-(3-{[2-(4-Fluorophenyl)-1H-pyrrolo[2,3-b]-pyridin-4-ylamino]methyl}pyridin-2-yl)-N-methylmethanesulfonamide | 11.75 (s, 1H), 8.42 (d, J = 4.7, 1H), 7.82 (dd, J = 9.0, 5.4, 1H), 7.74 (t, J = 7.0, 1H), 7.38 (dd, J = 7.7, 4.7, 1H), 7.28 (t, J = 8.8, 2H), 6.97 (s, 1H), 5.93 (d, J = 5.5, 1H), 4.63 (d, J = 6.1, 2H), 3.25 (s, 3H), 3.17 (s, 3H). | 3.461 min [426.2] |
| "A26" | (2,5-Difluorobenzyl)-[2-(4-fluorophenyl)-5-trifluoromethyl-1H-pyrrolo[2,3-b]pyridin-4-yl]-amine | 12.23 (s, 1H), 8.13 (s, 1H), 7.76 (dd, J = 8.9, 5.4, 1H), 7.35-7.25 (m, 2H), 7.16-7.08 (m, 1H), 7.06-7.00 (m, 1H), 6.89 (s, 1H), 6.83 (d, J = 2.2, 1H), 4.98 (d, J = 6.5, 2H). | 4.520 min [422.0] |

| No. | Structure/name | ¹H NMR (400 MHz, DMSO-d₆) δ [ppm] J [Hz] | LC-MS; rt; [M + H]⁺ |
|---|---|---|---|
| "A27" | 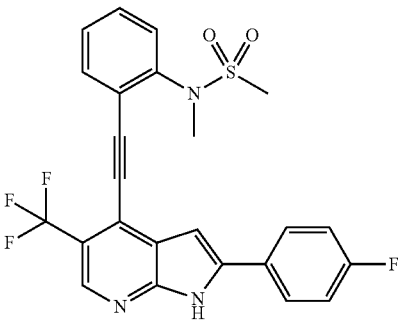 [SMILES: CN(c1ccccc1C#Cc1c(C(F)(F)F)cnc2[nH]c(-c3ccc(F)cc3)cc12)S(C)(=O)=O]<br>N-{2-[2-(4-Fluorophenyl)-5-trifluoromethyl-1H-pyrrolo[2,3-b]pyridin-4-ylethynyl]phenyl}-N-methylmethanesulfonamide | 12.87 (s, 1H), 8.59 (s, 1H), 8.10 (dd, J = 8.9, 5.3, 2H), 7.75 (dd, J = 7.6, 1.5, 1H), 7.72-7.66 (m, 1H), 7.61 (td, J = 7.7, 1.6, 1H), 7.52 (td, J = 7.5, 1.2, 1H), 7.39 (m, 3H), 3.34 (s, 3H), 3.18 (s, 3H). | 5.395 min [488.0] |
| "A28" | 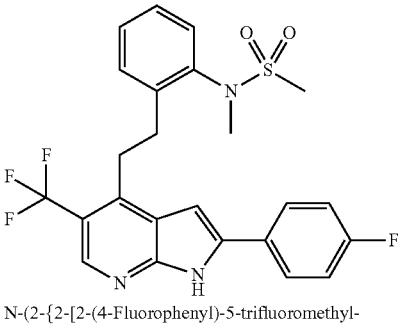<br>N-(2-{2-[2-(4-Fluorophenyl)-5-trifluoromethyl-1H-pyrrolo[2,3-b]pyridin-4-yl]ethyl}phenyl)-N-methylmethanesulfonamide | 12.62 (s, 1H), 8.50 (s, 1H), 8.10-8.03 (m, 2H), 7.57 (dd, J = 7.6, 1.5, 1H), 7.47 (dd, J = 7.4, 1.8, 1H), 7.44-7.32 (m, 4H), 7.29 (d, J = 1.9, 1H), 3.25-3.18 (m, 3H), 3.22 (s, 3H), 3.14 (s, 3H), 2.95 (m, 1H). | 5.361 min [492.0] |
| "A29" | 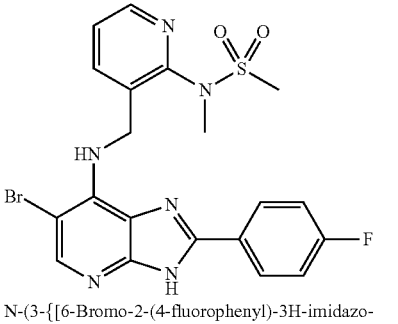<br>N-(3-{[6-Bromo-2-(4-fluorophenyl)-3H-imidazo-[4,5-b]pyridin-7-ylamino]methyl}pyridin-2-yl)-N-methylmethanesulfonamide | 13.34 (s, 1H), 8.37 (dd, J = 4.7, 1.8, 1H), 8.17-7.88 (m, 3H), 7.74 (dd, J = 7.8, 1.8, 1H), 7.45-7.16 (m, 1H), 6.78 (t, J = 6.8, 1H), 5.56 (d, J = 5.6, 2H), 3.22 (s, 3H), 3.16 (s, 3H). | 5.708 min [503.0 + 505.0] |
| "A30" | 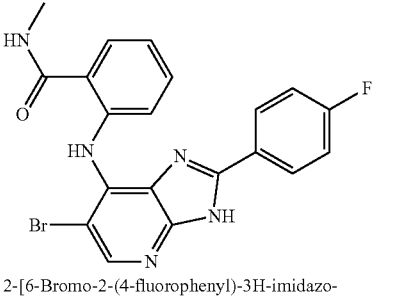<br>2-[6-Bromo-2-(4-fluorophenyl)-3H-imidazo-[4,5-b]pyridin-7-ylamino]-N-methylbenzamide | 13.58 (s, 1H), 10.42 (s, 1H), 8.69 (d, J = 4.4, 1H), 8.34 (s, 1H), 7.63 (d, J = 7.8, 1H), 7.40-7.31 (m, 4H), 7.25 (d, J = 7.8, 1H), 7.03 (t, J = 7.6, 1H), 2.81 (d, J = 4.5, 3H). | 3.282 min [438 + 440.0] |

-continued

| No. | Structure/name | ¹H NMR (400 MHz, DMSO-d₆) δ [ppm] J [Hz] | LC-MS; rt; [M + H]⁺ |
|---|---|---|---|
| "A31" | 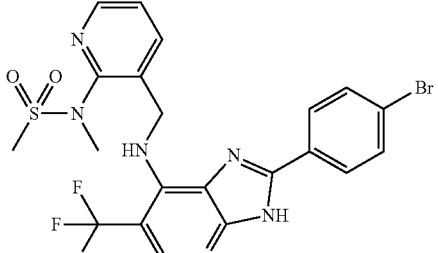<br>N-(3-{[2-(4-Bromophenyl)-6-trifluoromethyl-3H-imidazo[4,5-b]pyridin-7-ylamino]methyl}pyridin-2-yl)-N-methylmethanesulfonamide | 13.58 (s, 1H), 8.37 (dd, J = 4.7, 1.8, 1H), 8.22 (s, 1H), 7.98-7.93 (m, 2H), 7.73 (dd, J = 7.7, 1.7, 1H), 7.69 (d, J = 8.6, 3H), 7.36 (dd, J = 7.8, 4.7, 1H), 7.12 (t, J = 6.4, 1H), 5.63 (d, J = 5.9, 2H), 3.21 (s, 3H), 3.17 (s, 3H). | 4.221 min [553.0 + 555.0] |
| "A32" | 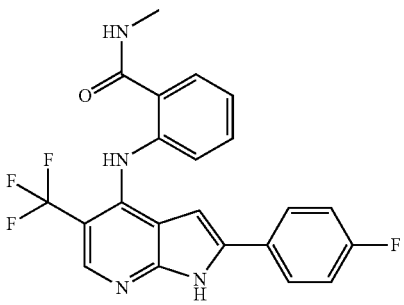 [SMILES: CNC(=O)c1ccccc1Nc1c(C(F)(F)F)cnc2[nH]c(-c3ccc(F)cc3)cc12]<br>2-[2-(4-Fluorophenyl)-5-trifluoromethyl-1H-pyrrolo[2,3-b]pyridin-4-ylamino]-N-methyl-benzamide | 12.51 (s, 1H), 10.58 (s, 1H), 8.69 (d, J = 4.6, 1H), 8.42 (s, 1H), 7.75 (m, 3H), 7.40-7.33 (m, 1H), 7.30-7.23 (m, 2H), 7.08-7.03 (m, 1H), 7.01 (d, J = 8.3, 1H), 6.10 (d, J = 2.2, 1H), 2.80 (d, J = 4.6, 3H). | 3.906 min [429.0] |
| "A33" | 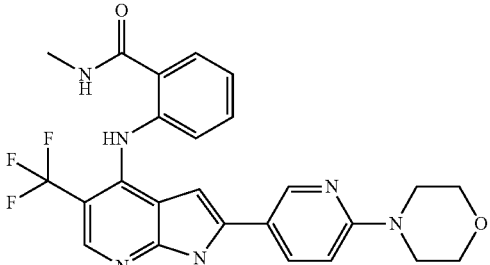<br>N-Methyl-2-[2-(6-morpholin-4-ylpyridin-3-yl)-5-trifluoromethyl-1H-pyrrolo[2,3-b]pyridin-4-yl-amino]benzamide | 12.40 (s, 1H), 10.57 (s, 1H), 8.69 (d, J = 4.7, 1H), 8.51 (d, J = 2.4, 1H), 8.38 (s, 1H), 7.84 (dd, J = 8.9, 2.5, 1H), 7.73 (d, J = 6.5, 1H), 7.35 (t, J = 7.1, 1H), 7.03 (t, J = 7.1, 1H), 6.97 (d, J = 8.3, 1H), 6.88 (d, J = 8.9, 1H), 5.99 (d, J = 2.2, 2H), 3.73-3.63 (m, 4H), 3.52-3.45 (m, 4H), 2.79 (d, J = 4.5, 3H). | 2.874 min [497.2] |
| "A34" | 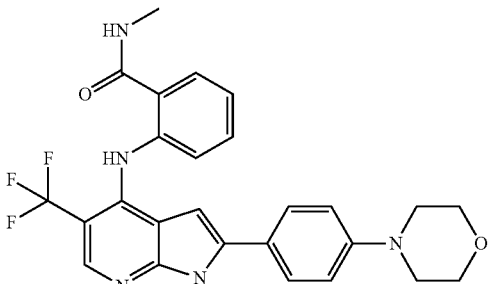<br>N-Methyl-2-[2-(4-morpholin-4-ylphenyl)-5-trifluoromethyl-1H-pyrrolo[2,3-b]pyridin-4-ylamino]benzamide | 12.32 (s, 1H), 10.53 (s, 1H), 8.69 (d, J = 4.7, 1H), 8.33 (d, J = 26.1, 1H), 7.73 (d, J = 6.9, 1H), 7.58 (d, J = 8.8, 2H), 7.35 (t, J = 7.4, 1H), 7.03 (t, J = 7.6, 1H), 6.97 (d, J = 8.7, 3H), 5.94 (d, J = 1.7, 1H), 3.79-3.67 (m, 4H), 3.21-3.07 (m, 4H), 2.80 (d, J = 4.4, 3H). | 3.614 min [496.3] |

-continued

| No. | Structure/name | $^1$H NMR (400 MHz, DMSO-d$_6$) δ [ppm] J [Hz] | LC-MS; rt; [M + H]$^+$ |
|---|---|---|---|
| "A35" | N-(3-{[2-(4-Fluorophenyl)-6-trifluoromethyl-3H-imidazo[4,5-b]pyridin-7-ylamino]methyl}pyridin-2-yl)-N-methylmethanesulfonamide | 13.51 (s, 1H), 8.37 (dd, J = 4.7, 1.8, 1H), 8.21 (s, 1H), 8.06 (dd, J = 8.9, 5.5, 2H), 7.74 (d, J = 7.8, 1H), 7.38-7.29 (m, 3H), 7.09 (s, 1H), 5.63 (d, J = 6.2, 2H), 3.21 (s, 3H), 3.16 (s, 3H). | 3.871 min [495.0] |
| "A36" | N-Methyl-2-[2-(6-oxo-1,6-dihydropyridin-3-yl)-5-trifluoromethyl-1H-pyrrolo[2,3-b]pyridin-4-yl-amino]benzamide | 12.46-12.09 (m, 2H), 12.05-11.74 (m, 1H), 10.60 (s, 1H), 8.68 (s, 2H), 8.36 (s, 1H), 7.92 (s, 1H), 7.73 (d, J = 7.7, 1H), 7.65 (d, J = 9.6, 1H), 7.34 (s, 1H), 7.01 (s, 1H), 6.93 (d, J = 8.3, 1H), 6.38 (d, J = 9.7, 1H), 5.93 (s, 1H), 2.79 (d, J = 4.3, 3H). | 2.730 min [428.0] |
| "A37" | 2-[[5-(1,1-Difluoroethyl)-2-(2-methoxy-4-morpholinophenyl)-1H-pyrrolo[2,3-b]pyridin-4-yl]amino]-N-methylbenzamide | | |
| "A38" | 2-[2-[[5-Cyclopropyl-2-(2-methoxy-4-morpholinophenyl)-1H-pyrrolo[2,3-b]pyridin-4-yl]amino]phenyl]acetonitrile | | |

| No. | Structure/name | ¹H NMR (400 MHz, DMSO-d₆) δ [ppm] J [Hz] | LC-MS; rt; [M + H]⁺ |
|---|---|---|---|
| "A39" | 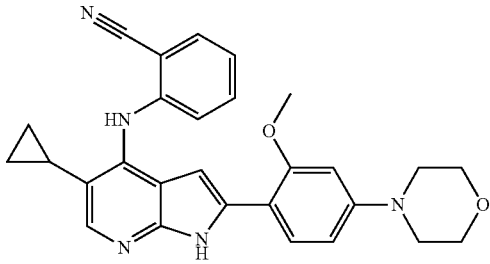 [SMILES: COc1cc(N2CCOCC2)ccc1-c1cc2c(Nc3ccccc3C#N)c(C3CC3)cnc2[nH]1]<br>2-[[5-Cyclopropyl-2-(2-methoxy-4-morpholino-phenyl)-1H-pyrrolo[2,3-b]pyridin-4-yl]amino]-benzonitrile | | |
| "A40" | 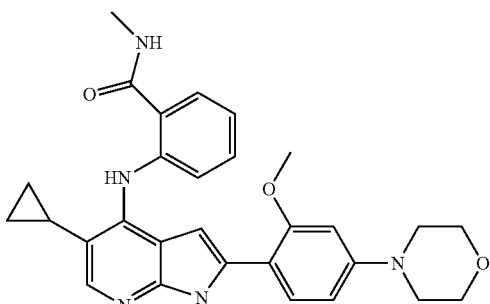<br>2-[[5-Cyclopropyl-2-(2-methoxy-4-morpholino-phenyl)-1H-pyrrolo[2,3-b]pyridin-4-yl]amino]-N-methylbenzamide | | |
| "A41" | 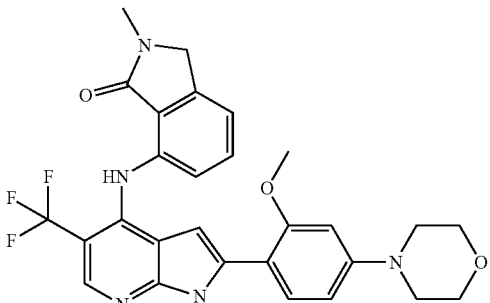<br>7-[[2-(2-Methoxy-4-morpholinophenyl)-5-(tri-fluoromethyl)-1H-pyrrolo[2,3-b]pyridin-4-yl]-amino]-2-methylisoindolin-1-one | | |
| "A42" | 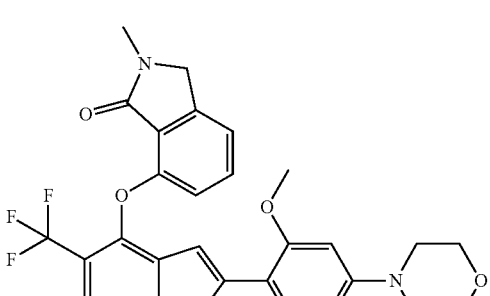<br>7-[[2-(2-Methoxy-4-morpholinophenyl)-5-(tri-fluoromethyl)-1H-pyrrolo[2,3-b]pyridin-4-yl]oxy]-2-methylisoindolin-1-one | | |

| No. | Structure/name | ¹H NMR (400 MHz, DMSO-d₆) δ [ppm] J [Hz] | LC-MS; rt; [M + H]⁺ |
|---|---|---|---|
| "A43" | 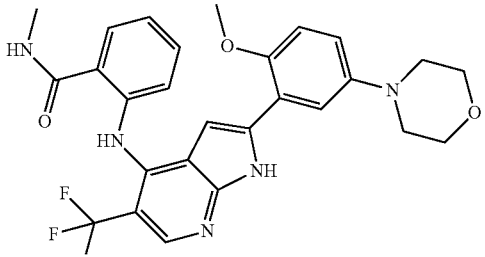 2-[[2-(2-Methoxy-5-morpholinophenyl)-5-(trifluoromethyl)-1H-pyrrolo[2,3-b]pyridin-4-yl]-amino]-N-methylbenzamide | | |
| "A44" | 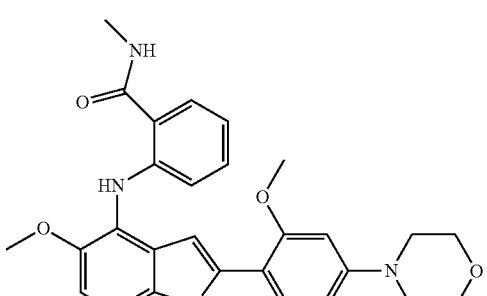 2-[[5-Methoxy-2-(2-methoxy-4-morpholinophenyl)-1H-pyrrolo[2,3-b]pyridin-4-yl]amino]-N-methylbenzamide | | |
| "A45" | 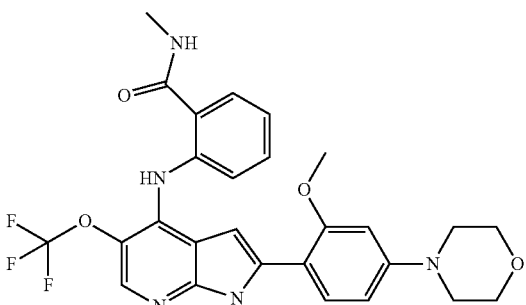 2-[[2-(2-Methoxy-4-morpholinophenyl)-5-(trifluoromethoxy)-1H-pyrrolo[2,3-b]pyridin-4-yl]-amino]-N-methylbenzamide | | |
| "A46" | 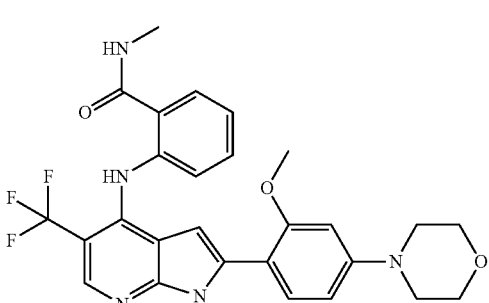 2-[[2-(2-Methoxy-4-morpholinophenyl)-5-(trifluoromethyl)-1H-pyrrolo[2,3-b]pyridin-4-yl]-amino]-N-methylbenzamide | | |

| No. | Structure/name | ¹H NMR (400 MHz, DMSO-d₆) δ [ppm] J [Hz] | LC-MS; rt; [M + H]⁺ |
|---|---|---|---|

"A47"

N-Methyl-N-[3-[[[2-(6-oxo-1H-pyridin-3-yl)-5-(trifluoromethyl)-1H-pyrrolo[2,3-b]pyridin-4-yl]-amino]methyl]-2-pyridyl]methanesulfonamide

"A48"

N-[3-[[[2-(2-Methoxyphenyl)-5-(trifluoromethyl)-1H-pyrrolo[2,3-b]pyridin-4-yl]amino]methyl]-2-pyridyl]-N-methylmethanesulfonamide

"A49"

N-[3-[[[2-(2-Methoxyphenyl)-5-(trifluoromethyl)-1H-pyrrolo[2,3-b]pyridin-4-yl]amino]methyl]-2-pyridyl]-N-methylmethanesulfonamide

"A50"

N-Methyl-N-[3-[[[2-(6-morpholino-3-pyridyl)-5-(trifluoromethyl)-1H-pyrrolo[2,3-b]pyridin-4-yl]-amino]methyl]-2-pyridyl]methanesulfonamide -continued

| No. | Structure/name | $^1$H NMR (400 MHz, DMSO-$d_6$) δ [ppm] J [Hz] | LC-MS; rt; [M + H]$^+$ |
|---|---|---|---|
| "A51" | 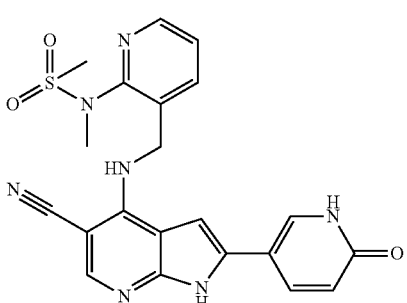 N-[3-[[[5-Cyano-2-(6-oxo-1H-pyridin-3-yl)-1H-pyrrolo[2,3-b]pyridin-4-yl]amino]methyl]-2-pyridyl]-N-methylmethanesulfonamide | | |
| "A52" | 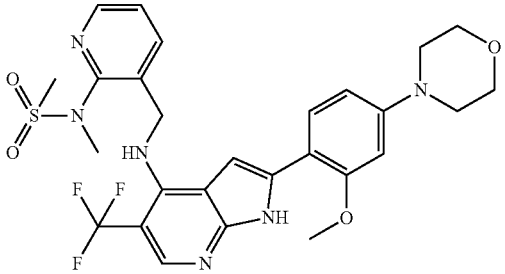 [SMILES: COc1cc(N2CCOCC2)ccc1-c1cc2c(NCc3cccnc3N(C)S(C)(=O)=O)c(C(F)(F)F)cnc2[nH]1] N-[3-[[[2-(2-Methoxy-4-morpholinophenyl)-5-(trifluoromethyl)-1H-pyrrolo[2,3-b]pyridin-4-yl]-amino]methyl]-2-pyridyl]-N-methylmethanesulfonamide | | |
| "A53" | 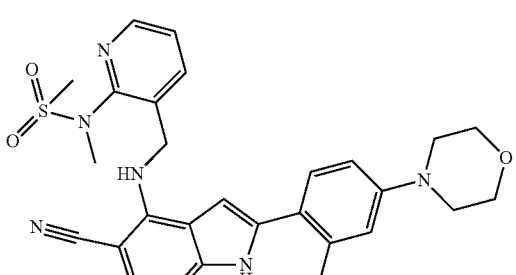 N-[3-[[[5-Cyano-2-(2-methoxy-4-morpholino-phenyl)-1H-pyrrolo[2,3-b]pyridin-4-yl]amino]-methyl]-2-pyridyl]-N-methylmethanesulfonamide | | |
| "A54" | 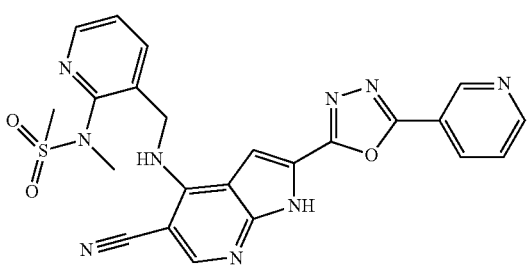 [SMILES: CN(c1ncccc1CNc1c(C#N)cnc2[nH]c(-c3nnc(-c4cccnc4)o3)cc12)S(C)(=O)=O] N-[3-[[[5-Cyano-2-[5-(3-pyridyl)-1,3,4-oxa-diazol-2-yl]-1H-pyrrolo[2,3-b]pyridin-4-yl]-amino]methyl]-2-pyridyl]-N-methylmethanesulfonamide | | |

| No. | Structure/name | ¹H NMR (400 MHz, DMSO-d₆) δ [ppm] J [Hz] | LC-MS; rt; [M + H]⁺ |
|---|---|---|---|
| "A55" | N-[3-[[[5-Cyano-2-(5-methyl-1,3,4-oxadiazol-2-yl)-1H-pyrrolo[2,3-b]pyridin-4-yl]amino]methyl]-2-pyridyl]-N-methylmethanesulfonamide | | |
| "A56" | N-[3-[[[2-(4-Fluorophenyl)-5-(trifluoromethyl)-1H-pyrrolo[2,3-b]pyridin-4-yl]amino]methyl]-4-methyl-2-pyridyl]-N-methylmethanesulfonamide | | |
| "A57" | N-[3-[[[5-Cyano-2-(4-fluorophenyl)-1H-pyrrolo-[2,3-b]pyridin-4-yl]amino]methyl]-4-methyl-2-pyridyl]-N-methylmethanesulfonamide | | |
| "A58" | 2-[[5-Cyano-2-(4-fluorophenyl)-1H-pyrrolo-[2,3-b]pyridin-4-yl]amino]-N,3-dimethylbenzamide | | |

| No. | Structure/name | ¹H NMR (400 MHz, DMSO-d₆) δ [ppm] J [Hz] | LC-MS; rt; [M + H]⁺ |
|---|---|---|---|
| "A59" | 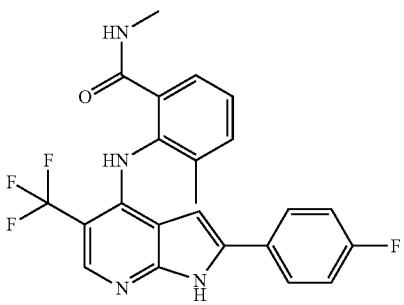 [SMILES: CNC(=O)c1cccc(C)c1Nc1c(C(F)(F)F)cnc2[nH]c(-c3ccc(F)cc3)cc12]<br>2-[[2-(4-Fluorophenyl)-5-(trifluoromethyl)-1H-pyrrolo[2,3-b]pyridin-4-yl]amino]-N,3-dimethyl-benzamide | | |
| "A60" | 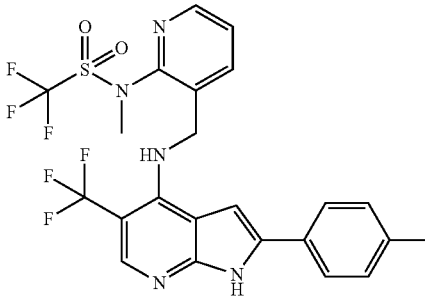<br>1,1,1-Trifluoro-N-[3-[[[2-(4-fluorophenyl)-5-(trifluoromethyl)-1H-pyrrolo[2,3-b]pyridin-4-yl]-amino]methyl]-2-pyridyl]-N-methylmethane-sulfonamide | | |
| "A61" | 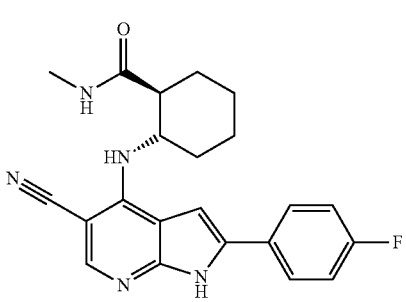<br>(1S)-2-[[5-Cyano-2-(4-fluorophenyl)-1H-pyrrolo[2,3-b]pyridin-4-yl]amino]-N-methyl-cyclohexanecarboxamide | | |
| "A62" | 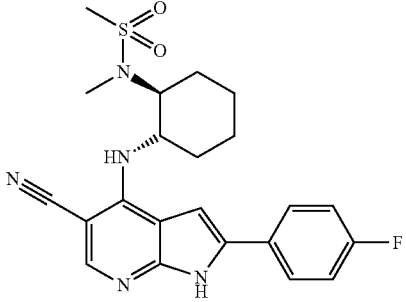<br>N-[(1S)-2-[[5-Cyano-2-(4-fluorophenyl)-1H-pyrrolo[2,3-b]pyridin-4-yl]amino]cyclohexyl]-N-methylmethanesulfonamide | | |

| No. | Structure/name | ¹H NMR (400 MHz, DMSO-d₆) δ [ppm] J [Hz] | LC-MS; rt; [M + H]⁺ |
|---|---|---|---|
| "A63" | 1-[[5-Cyano-2-(4-fluorophenyl)-1H-pyrrolo-[2,3-b]pyridin-4-yl]amino]-N-methylcyclo-propanecarboxamide | | |
| "A64" | 1-[[2-(4-Fluorophenyl)-5-(trifluoromethyl)-1H-pyrrolo[2,3-b]pyridin-4-yl]amino]-N-methyl-cyclopropanecarboxamide | | |
| "A65" | N-[3-[[[5-(1,1-Difluoroethyl)-2-(4-fluorophenyl)-1H-pyrrolo[2,3-b]pyridin-4-yl]amino]methyl]-2-pyridyl]-N-methylmethanesulfonamide | | |
| "A66" | N-[3-[[[5-(1,1-Difluoroethyl)-2-(4-fluorophenyl)-1H-pyrrolo[2,3-b]pyridin-4-yl]amino]methyl]-2-pyridyl]-1,1,1-trifluoro-N-methylmethane-sulfonamide | | |

| No. | Structure/name | ¹H NMR (400 MHz, DMSO-d₆) δ [ppm] J [Hz] | LC-MS; rt; [M + H]⁺ |
|---|---|---|---|
| "A67" | N-(2-Aminoethyl)-3-[5-cyano-4-[[2-[methyl-(methylsulfonyl)amino]-3-pyridyl]methylamino]-1H-pyrrolo[2,3-b]pyridin-2-yl]benzamide | | |
| "A68" | 3-[5-Cyano-4-[[2-[methyl(methylsulfonyl)-amino]-3-pyridyl]methylamino]-1H-pyrrolo-[2,3-b]pyridin-2-yl]-N-methylbenzamide | | |
| "A69" | 3-[5-Cyano-4-[[2-[methyl(methylsulfonyl)-amino]-3-pyridyl]methylamino]-1H-pyrrolo-[2,3-b]pyridin-2-yl]-N-(1-methyl-4-piperidyl)benzamide | | |
| "A70" | 4-[5-Cyano-4-[[2-[methyl(methylsulfonyl)-amino]-3-pyridyl]methylamino]-1H-pyrrolo-[2,3-b]pyridin-2-yl]-N-(1-methyl-4-piperidyl)-benzamide | | |

| No. | Structure/name | ¹H NMR (400 MHz, DMSO-d₆) δ [ppm] J [Hz] | LC-MS; rt; [M + H]⁺ |
|---|---|---|---|
| "A71" | N-[3-[[[2-[(2S)-4-(2-Aminoethyl)-2-methyl-piperidine-1-carbonyl]-5-cyano-1H-pyrrolo-[2,3-b]pyridin-4-yl]amino]methyl]-2-pyridyl]-N-methylmethanesulfonamide | | |
| "A72" | N-[3-[[[2-(4-Aminopiperidine-1-carbonyl)-5-cyano-1H-pyrrolo[2,3-b]pyridin-4-yl]amino]-methyl]-2-pyridyl]-N-methylmethanesulfonamide | | |
| "A73" | N-[3-[[[5-Cyano-2-[3-(dimethylamino)-pyrrolidine-1-carbonyl]-1H-pyrrolo[2,3-b]-pyridin-4-yl]amino]methyl]-2-pyridyl]-N-methylmethanesulfonamide | | |
| "A74" | 5-Cyano-N-(2-dimethylaminoethyl)-4-[[2-[methyl(methylsulfonyl)amino]-3-pyridyl]methyl-amino]-1H-pyrrolo[2,3-b]pyridine-2-carboxamide | | |

-continued

| No. | Structure/name | $^1$H NMR (400 MHz, DMSO-$d_6$) δ [ppm] J [Hz] | LC-MS; rt; [M + H]$^+$ |
|---|---|---|---|
| "A75" | 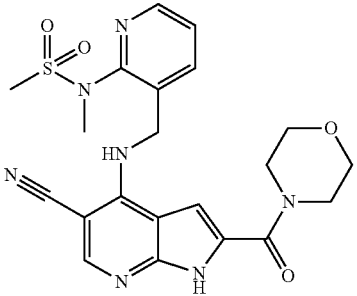 [SMILES: CN(c1ncccc1CNc1c(C#N)cnc2[nH]c(C(=O)N3CCOCC3)cc12)S(C)(=O)=O]<br>N-[3-[[[5-Cyano-2-(morpholine-4-carbonyl)-1H-pyrrolo[2,3-b]pyridin-4-yl]amino]methyl]-2-pyridyl]-N-methylmethanesulfonamide | | |
| "A76" | 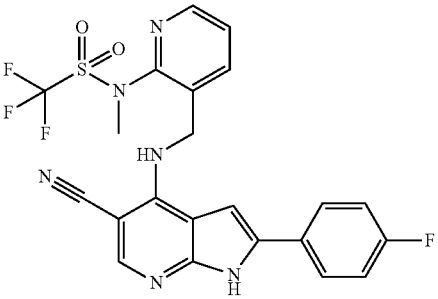 [SMILES: CN(c1ncccc1CNc1c(C#N)cnc2[nH]c(-c3ccc(F)cc3)cc12)S(=O)(=O)C(F)(F)F]<br>N-[3-[[[5-Cyano-2-(4-fluorophenyl)-1H-pyrrolo-[2,3-b]pyridin-4-yl]amino]methyl]-2-pyridyl]-1,1,1-trifluoro-N-methylmethanesulfonamide | | |
| "A77" | 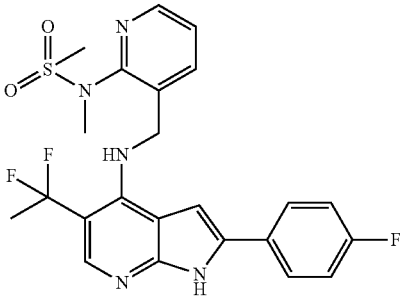 [SMILES: CN(c1ncccc1CNc1c(C(C)(F)F)cnc2[nH]c(-c3ccc(F)cc3)cc12)S(C)(=O)=O]<br>N-[3-[[[5-(1,1-Difluoroethyl)-2-(4-fluorophenyl)-1H-pyrrolo[2,3-b]pyridin-4-yl]amino]methyl]-2-pyridyl]-N-methylmethanesulfonamide | | |
| "A78" | 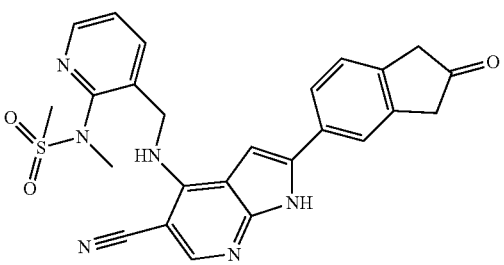 [SMILES: CN(c1ncccc1CNc1c(C#N)cnc2[nH]c(-c3ccc4c(c3)CC(=O)C4)cc12)S(C)(=O)=O]<br>N-[3-[[[5-Cyano-2-(2-oxoindan-5-yl)-1H-pyrrolo-[2,3-b]pyridin-4-yl]amino]methyl]-2-pyridyl]-N-methylmethanesulfonamide | | |

-continued

| No. | Structure/name | ¹H NMR (400 MHz, DMSO-d₆) δ [ppm] J [Hz] | LC-MS; rt; [M + H]⁺ |
|---|---|---|---|
| "A79" | 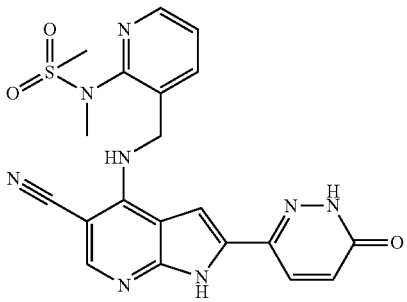 [SMILES: CN(c1ncccc1CNc1c(C#N)cnc2[nH]c(-c3ccc(=O)[nH]n3)cc12)S(C)(=O)=O]<br>N-[3-[[[5-Cyano-2-(6-oxo-1H-pyridazin-3-yl)-1H-pyrrolo[2,3-b]pyridin-4-yl]amino]methyl]-2-pyridyl]-N-methylmethanesulfonamide | | |
| "A80" | 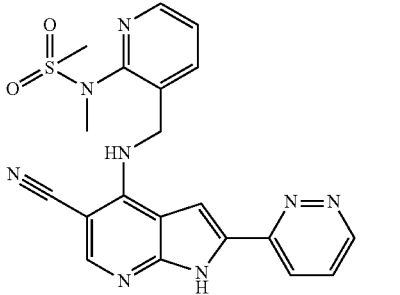 [SMILES: CN(c1ncccc1CNc1c(C#N)cnc2[nH]c(-c3cccnn3)cc12)S(C)(=O)=O]<br>N-[3-[[(5-Cyano-2-pyridazin-3-yl-1H-pyrrolo-[2,3-b]pyridin-4-yl)amino]methyl]-2-pyridyl]-N-methylmethanesulfonamide | | |
| "A81" | 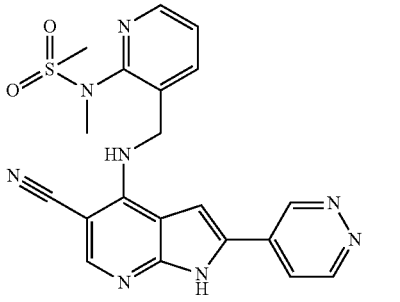 [SMILES: CN(c1ncccc1CNc1c(C#N)cnc2[nH]c(-c3ccnnc3)cc12)S(C)(=O)=O]<br>N-[3-[[(5-Cyano-2-pyridazin-4-yl-1H-pyrrolo-[2,3-b]pyridin-4-yl)amino]methyl]-2-pyridyl]-N-methylmethanesulfonamide | | |
| "A82" | 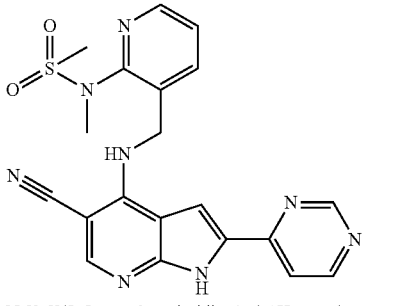<br>N-[3-[[(5-Cyano-2-pyrimidin-4-yl-1H-pyrrolo-[2,3-b]pyridin-4-yl)amino]methyl]-2-pyridyl]-N-methylmethanesulfonamide | | |

| No. | Structure/name | ¹H NMR (400 MHz, DMSO-d₆) δ [ppm] J [Hz] | LC-MS; rt; [M + H]⁺ |
|---|---|---|---|
| "A83" | N-[3-[[[5-Cyano-2-(6-oxo-5,7-dihydrocyclopenta[b]pyridin-3-yl)-1H-pyrrolo[2,3-b]pyridin-4-yl]amino]methyl]-2-pyridyl]-N-methylmethanesulfonamide | | |
| "A84" | N-[3-[[[5-Cyano-2-(2-oxoindolin-6-yl)-1H-pyrrolo[2,3-b]pyridin-4-yl]amino]methyl]-2-pyridyl]-N-methylmethanesulfonamide | | |
| "A85" | N-[3-[[[5-Cyano-2-(2-oxoindolin-5-yl)-1H-pyrrolo[2,3-b]pyridin-4-yl]amino]methyl]-2-pyridyl]-N-methylmethanesulfonamide | | |
| "A86" | N-[3-[[(5-Cyano-2-isoxazol-4-yl-1H-pyrrolo-[2,3-b]pyridin-4-yl)amino]methyl]-2-pyridyl]-N-methylmethanesulfonamide | | |

| No. | Structure/name | ¹H NMR (400 MHz, DMSO-d₆) δ [ppm] J [Hz] | LC-MS; rt; [M + H]⁺ |
|---|---|---|---|
| "A87" | N-[3-[[[5-Cyano-2-(1-methylpyrazol-4-yl)-1H-pyrrolo[2,3-b]pyridin-4-yl]amino]methyl]-2-pyridyl]-N-methylmethanesulfonamide | | |
| "A88" | 2-(3-Methoxyphenyl)-4-(1-methyl-1H-pyrazol-4-yl)-5-trifluoromethyl-1H-pyrrolo[2,3-b]pyridine | 12.66 (s, 1H), 8.57 (s, 1H), 8.14 (s, 1H), 7.75 (s, 1H), 7.56 (s, 2H), 7.38 (t, J = 8.3, 1H), 7.04 (s, 1H), 6.95 (d, J = 7.4, 1H), 3.98 (s, 3H), 3.84 (s, 3H). | 4.396 min [373.0] |
| "A89" | 2-[2-(2-Methoxy-4-morpholin-4-ylphenyl)-5-trifluoromethyl-1H-pyrrolo[2,3-b]pyridin-4-yl-amino]benzonitrile | 11.89 (s, 1H), 8.59 (s, 1H), 8.28 (s, 1H), 7.87-7.74 (m, 1H), 7.72 (t, J = 7.1, 1H), 7.59 (d, J = 8.6, 1H), 7.46-7.29 (m, 2H), 6.61-6.44 (m, 2H), 5.59 (d, J = 2.1, 1H), 3.77-3.67 (m, 4H), 3.65 (s, 3H), 3.22-3.13 (m, 4H). | 3.851 min [494.2] |
| "A90" | 4-[4-(3-Morpholin-4-ylphenyl)-5-trifluoromethyl-1H-pyrrolo[2,3-b]pyridin-2-yl]benzamide | 12.80 (s, 1H), 8.63 (s, 1H), 8.02 (d, J = 8.6, 2H), 7.93 (d, J = 8.6, 2H), 7.42-7.36 (m, 2H), 7.09 (ddd, J = 8.5, 2.6, 0.8, 1H), 6.97 (m, 1H), 6.87 (d, J = 8.0, 1H), 6.73 (d, J = 2.1, 1H), 3.73 (m, 4H), 3.15 (m, 4H). | |

-continued

| No. | Structure/name | $^1$H NMR (400 MHz, DMSO-d$_6$) δ [ppm] J [Hz] | LC-MS; rt; [M + H]$^+$ |
|---|---|---|---|
| "A91" | 4-(4-Fluorophenyl)-2-piperidin-4-yl-5-trifluoromethyl-1H-pyrrolo[2,3-b]pyridine | 12.15 (s, 1H), 8.53 (s, 1H), 7.46-7.39 (m, 2H), 7.34 (m, 2H), 5.84 (s, 1H), 3.02 (m, 2H), 2.89 (s, 1H), 2.70 (s, 1H), 2.04-1.87 (m, 4H), 1.62 (m, 2H). | |
| "A92" | (3,5-Difluorobenzyl)-[2-(4-morpholin-4-yl-phenyl)-5-trifluoromethyl-1H-pyrrolo[2,3-b]-pyridin-4-yl]amine | 11.99 (s, 1H), 8.07 (s, 1H), 7.64 (d, J = 8.9, 2H), 7.10 (d, J = 6.6, 2H), 7.07-7.01 (m, 1H), 6.95 (m, 3H), 6.75 (s, 1H), 4.96 (d, J = 6.6, 2H), 3.79-3.67 (m, 5H), 3.18-3.10 (m, 4H). | HPLC: 4.157 min [93.60% purity) |
| "A93" | 2-[2-(4-Fluorophenyl)-5-trifluoromethyl-1H-pyrrolo[2,3-b]pyridin-4-yloxy]benzonitrile | 12.93 (s, 1H), 8.61 (s, 1H), 8.00 (dd, J = 7.7, 1.5, 1H), 7.88 (dd, J = 8.8, 5.3, 2H), 7.69-7.62 (m, 1H), 7.40 (t, J = 7.4, 1H), 7.29 (t, J = 8.9, 2H), 7.05 (d, J = 8.5, 1H), 6.22 (s, 1H). | 5.334 min [398.3] |
| "A94" | 7-[2-(4-Fluorophenyl)-5-trifluoromethyl-1H-pyrrolo[2,3-b]pyridin-4-ylamino]-2-methyl-2,3-dihydroisoindol-1-one | 12.64 (s, 1H), 9.35 (s, 1H), 8.48 (s, 1H), 7.87 (dd, J = 8.9, 5.4, 2H), 7.40 (t, J = 7.8, 1H), 7.29 (t, J = 8.9, 2H), 7.07 (d, J = 7.4, 1H), 6.84 (d, J = 8.1, 1H), 6.45 (s, 1H), 4.50 (s, 2H), 3.08 (s, 3H). | 4.294 min [441.0] |

-continued

| No. | Structure/name | ¹H NMR (400 MHz, DMSO-d₆) δ [ppm] J [Hz] | LC-MS; rt; [M + H]⁺ |
|---|---|---|---|
| "A95" | {3-[4-(1-Methyl-1H-pyrazol-4-yl)-5-trifluoromethyl-1H-pyrrolo[2,3-b]pyridin-2-yl]phenyl}-morpholin-4-ylmethanone | 12.72 (s, 1H), 8.58 (s, 1H), 8.15 (s, 1H), 8.09-8.06 (m, 1H), 8.03 (d, J = 1.4 Hz, 1H), 7.76 (s, 1H), 7.55 (t, J = 7.7 Hz, 1H), 7.40-7.32 (m, 1H), 7.11 (d, J = 2.2 Hz, 1H), 3.98 (s, 3H), 3.65 (s, 4H), 3.40 (s, 2H), 3.31 (s, 2H). | 3.68 min [456.2] |
| "A96" | {4-[4-(1-Methyl-1H-pyrazol-4-yl)-5-trifluoromethyl-1H-pyrrolo[2,3-b]pyridin-2-yl]phenyl}-morpholin-4-ylmethanone | 12.75 (s, 1H), 8.59 (s, 1H), 8.15 (s, 1H), 8.06 (d, J = 8.3 Hz, 2H), 7.76 (s, 1H), 7.51 (d, J = 8.3 Hz, 2H), 7.11 (d, J = 1.6 Hz, 1H), 3.98 (s, 3H), 3.61 (s, 6H). | 3.62 min [456.2] |
| "A97" | 5-[2-(4-Morpholin-4-ylphenyl)-5-trifluoromethyl-1H-pyrrolo[2,3-b]pyridin-4-yl]-1H-pyridin-2-one | 12.55 (s, 1H), 11.91 (s, 1H), 8.51 (s, 1H), 7.84 (d, J = 8.8 Hz, 2H), 7.53-7.49 (m, 2H), 7.00 (d, J = 8.9 Hz, 2H), 6.67 (d, J = 1.9 Hz, 1H), 6.48 (d, J = 9.4 Hz, 1H), 3.73 (t, J = 5.0 Hz, 4H), 3.19 (t, J = 4.7 Hz, 4H). | 3.27 min [441.2] |
| "A98" | 5-[2-(3-Morpholin-4-ylphenyl)-5-trifluoromethyl-1H-pyrrolo[2,3-b]pyridin-4-yl]-1H-pyridin-2-one | 12.69 (s, 1H), 11.93 (s, 1H), 8.58 (s, 1H), 7.52 (d, J = 8.8 Hz, 3H), 7.42 (d, J = 7.8 Hz, 1H), 7.29 (t, J = 7.8 Hz, 1H), 6.96-6.93 (m, 1H), 6.88 (d, J = 2.0 Hz, 1H), 6.48 (d, J = 8.0 Hz, 1H), 3.76 (t, J = 5.0 Hz, 4H), 3.20 (t, J = 4.7 Hz, 4H). | 3.24 min [441.2] |

| No. | Structure/name | ¹H NMR (400 MHz, DMSO-d₆) δ [ppm] J [Hz] | LC-MS; rt; [M + H]⁺ |
|---|---|---|---|
| "A99" | 2-(4-Fluorophenyl)-5-trifluoromethyl-6-(1,3,5-trimethyl-1H-pyrazol-4-yl)-1H-pyrrolo[2,3-b]-pyridine | 12.57 (s, 1H), 8.39 (s, 1H), 8.02-7.99 (m, 2H), 7.38-7.33 (m, 2H), 7.08 (d, J = 2.0 Hz, 1H), 3.70 (s, 3H), 1.98 (s, 3H), 1.88 (s, 3H). | 4.78 min [389.2] |
| "A100" | 4-[2-(4-Morpholin-4-ylphenyl)-5-trifluoromethyl-1H-pyrrolo[2,3-b]pyridin-4-yl]phenylamine | 12.42 (s, 1H), 8.46 (s, 1H), 7.75 (d, J = 8.8 Hz, 2H), 7.10 (d, J = 8.9 Hz, 2H), 6.98 (d, J = 8.9 Hz, 2H), 6.7 (d, J = 8.4 Hz, 2H), 6.5 (d, J = 2.1 Hz, 1H), 5.4 (s, 2H), 3.7 (t, J = 4.6 Hz, 4H), 3.2 (t, J = 4.0 Hz, 4H). | 3.25 min [439] |
| "A101" | Methyl 3-[4-(1-methyl-1H-pyrazol-4-yl)-5-trifluoromethyl-1H-pyrrolo[2,3-b]pyridin-2-yl]-benzoate | 12.8 (s, 1H), 8.59-8.55 (m, 2H), 8.27-8.25 (m, 1H), 8.2 (s, 1H), 7.96-7.93 (m, 1H), 7.8 (s, 1H), 7.65-7.61 (m, 1H), 7.1 (s, 1H), 4.0 (s, 3H), 3.9 (s, 3H). | 4.38 min [401.2] |
| "A102" | 2-(4-Morpholin-4-ylphenyl)-4-(1H-pyrazol-4-yl)-5-trifluoromethyl-1H-pyrrolo[2,3-b]pyridine | 12.48 (d, J = 1.6 Hz, 1H), 8.50 (s, 1H), 7.96 (s, 2H), 7.86 (d, J = 8.9 Hz, 2H), 7.06 (d, J = 8.9 Hz, 2H), 6.79 (d, J = 2.1 Hz, 1H), 3.76 (t, J = 4.8 Hz, 4H), 3.21 (t, J = 4.8 Hz, 4H). | 3.49 min [414.2] |
| "A103" | 4-(1-Methyl-1H-pyrazol-4-yl)-2-(4-morpholin-4-ylphenyl)-5-trifluoromethyl-1H-pyrrolo[2,3-b]-pyridine | 12.46 (d, J = 1.4 Hz, 1H), 8.49 (s, 1H), 8.12 (s, 1H), 7.85 (d, J = 8.8 Hz, 2H), 7.72 (s, 1H), 7.02 (d, J = 8.9 Hz, 2H), 6.82 (d, J = 2.1 Hz, 1H), 3.97 (s, 3H), 3.74 (t, J = 5.0 Hz, 4H), 3.19 (t, J = 4.8 Hz, 4H). | 4.18 min [428.2] |

-continued

| No. | Structure/name | ¹H NMR (400 MHz, DMSO-d₆) δ [ppm] J [Hz] | LC-MS; rt; [M + H]⁺ |
|---|---|---|---|
| "A104" | 4-(1-Methyl-1H-pyrazol-4-yl)-2-(3-morpholin-4-ylphenyl)-5-trifluoromethyl-1H-pyrrolo[2,3-b]-pyridine | 12.61 (s, 1H), 8.55 (s, 1H), 8.13 (s, 1H), 7.74 (s, 1H), 7.53 (s, 1H), 7.42 (d, J = 7.8 Hz, 1H), 7.31 (t, J = 7.8 Hz, 1H), 7.00 (d, J = 2.1 Hz, 1H), 6.96-6.93 (m, 1H), 3.97 (s, 3H), 3.77 (t, J = 4.8 Hz, 4H), 3.21 (t, J = 4.7 Hz, 4H). | 4.07 min [428.2] |
| "A105" | 2-(4-Fluorophenyl)-4-(1-methyl-1H-pyrazol-4-yl)-5-trifluoromethyl-1H-pyrrolo[2,3-b]pyridine | 12.66 (s, 1H), 8.56 (s, 1H), 8.14 (s, 1H), 8.06-8.02 (m, 2H), 7.75 (s, 1H), 7.35-7.30 (m, 2H), 7.00 (d, J = 2.1 Hz, 1H), 3.97 (s, 3H). | 4.55 min [361.2] |
| "A106" | 2-(4-Fluorophenyl)-4-(1H-pyrazol-4-yl)-5-trifluoromethyl-1H-pyrrolo[2,3-b]pyridine | 13.33 (s, 1H), 12.65 (s, 1H), 8.56 (s, 1H), 8.13 (s, 1H), 8.06-8.02 (m, 2H), 7.82 (s, 1H), 7.31 (t, J = 8.8 Hz, 2H), 6.96 (s, 1H). | 4 min [347] |
| "A107" | 2-(3-Morpholin-4-ylphenyl)-4-(1H-pyrazol-4-yl)-5-trifluoromethyl-1H-pyrrolo[2,3-b]pyridine | 13.31 (s, 1H), 12.59 (s, 1H), 8.56 (s, 1H), 7.53 (s, 2H), 7.42 (d, J = 7.6 Hz, 2H), 7.30 (t, J = 7.7 Hz, 1H), 6.94 (d, J = 7.5 Hz, 2H), 3.76 (d, J = 4.2 Hz, 4H), 3.21 (d, J = 4.2 Hz, 4H). | 3.5 min [414] |
| "A108" | 2-(4-Fluorophenyl)-6-(1-methyl-1H-pyrazol-4-yl)-5-trifluoromethyl-1H-pyrrolo[2,3-b]pyridine | 12.60 (s, 1H), 8.37 (s, 1H), 8.03-8.00 (m, 3H), 7.80 (s, 1H), 7.34 (t, J = 8.9 Hz, 2H), 7.05 (d, J = 2.0 Hz, 1H), 3.92 (s, 3H). | 4.92 min [361] |

-continued

| No. | Structure/name | $^1$H NMR (400 MHz, DMSO-$d_6$) δ [ppm] J [Hz] | LC-MS; rt; [M + H]$^+$ |
|---|---|---|---|
| "A109" | 2-(4-Fluorophenyl)-6-(1H-pyrazol-4-yl)-5-tri-fluoromethyl-1H-pyrrolo[2,3-b]pyridine | 13.09 (s, 1H), 12.61 (s, 1H), 8.37 (s, 1H), 8.04-8.00 (m, 2H), 7.86 (s, 1H), 7.34 (t, J = 8.0 Hz, 2H), 7.05 (d, J = 1.4 Hz, 1H). | 4.77 min [347] |
| "A110" | 5-[2-(4-Fluorophenyl)-5-trifluoromethyl-1H-pyrrolo[2,3-b]pyridin-4-yl]-1H-pyridin-2-one | 12.75 (s, 1H), 11.94 (s, 1H), 8.59 (s, 1H), 8.06-8.03 (m, 2H), 7.52 (t, J = 8.5 Hz, 2H), 7.33-7.29 (m, 2H), 6.88 (d, J = 1.6 Hz, 1H), 6.48 (t, J = 8.5 Hz, 1H). | 3.68 min [374] |

$) 
HPLC
Column: Xbridge C8(50×4.6) mm, 3.5 μm
Mobile Phase:
A: 0.1% of TFA in H$_2$O
B: 0.1% of TFA in ACN
Flow Rate: 2.0 ml/min
Gradien:

| Time | % of B |
|---|---|
| 0 | 5 |
| 8.0 | 100 |
| 8.1 | 100 |
| 8.5 | 5 |
| 10.0 | 5 |

2) LC-MS
Column: XBridge C8, 3.5 μm, 4.6×50 mm; +ve mode
Solvent A: water+0.1% of TFA;
Solvent B: ACN+0.1% of TFA;
Flow: 2 ml/min;
Gradient:

| Min | % of B |
|---|---|
| 0 | 05 |
| 8.0 | 100 |
| 8.1 | 100 |
| 8.5 | 05 |
| 10.0 | 05 |

%
Only 2 min run time
%6
Only 6 min run time

&
Column: Waters Xbridge (C18, 50×2.1 mm, 3.5 micron)
Flow: 0.8 ml/min Column temp: 25° C.
Eluent A: acetonitrile 95%+10 mM ammonium bicarbonate 5%
Eluent B: 10 mM ammonium bicarbonate in water
Lin. Gradient: t=0 min 2% of A, t=3.5 min 98% oif A, t=6 min 98% of A
Detection: DAD (220-320 nm)
Detection: MSD (ESI pos/neg) mass range: 100-800

Pharmacological Test Results

TABLE 1

FAK inhibition of some compunds of the formula I according to the invention

| No. | IC$_{50}$ (enzymatic) | IC$_{50}$ (cellular) |
|---|---|---|
| "A1" | C | |
| "A2" | C | |
| "A3" | C | |
| "A4" | C | |
| "A5" | C | |
| "A6" | C | |
| "A7" | C | |
| "A9" | A | B |
| "A10" | B | C |
| "A11" | A | B |
| "A12" | B | C |
| "A13" | C | C |
| "A14" | C | C |
| "A21" | A | B |
| "A22" | A | A |
| "A24" | B | C |
| "A25" | C | C |
| "A30" | A | C |

TABLE 1-continued

FAK inhibition of some compunds of the formila I according to the invention

| No. | IC$_{50}$ (enzymatic) | IC$_{50}$ (cellular) |
|---|---|---|
| "A31" | A | C |
| "A32" | A | B |
| "A33" | A | A |

IC$_{50}$: <0.3 µM = A 0.3-3 µM = B >3-50 µM = C

TABLE 2

IKKε, PDK1 and TBK1 inhibition of some compounds of the formula according to the invention

| No. | IKKe IC$_{50}$ (enzymatic) | PDK1 IC$_{50}$ (enzymatic) | TBK1 IC$_{50}$ (enzymatic) |
|---|---|---|---|
| "A95" | C | B | B |
| "A96" | B | A | A |
| "A97" | B | B | B |
| "A100" |  |  | B |
| "A102" |  | C |  |
| "A104" |  | B |  |
| "A105" |  | B |  |

IC$_{50}$: <0.3 µM = A 0.3-3 µM = B >3-50 µM = C

The following examples relate to pharmaceutical preparations:

Example A

Injection Vials

A solution of 100 g of an active compound of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active compound.

Example B

Suppositories

A mixture of 20 g of an active compound of the formula I with 100 g of soya lecithin and 1400 g of cocoa butter is melted, poured into moulds and allowed to cool. Each suppository contains 20 mg of active compound.

Example C

Solution

A solution is prepared from 1 g of an active compound of the formula I, 9.38 g of NaH$_2$PO$_4$.2 H$_2$O, 28.48 g of Na$_2$HPO$_4$.12 H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

Example D

Ointment 500 mg of an active compound of the formula I are mixed with 99.5 g of Vaseline under aseptic conditions.

Example E

Tablets

A mixture of 1 kg of active compound of the formula I, 4 kg of lactose, 1.2 kg of potato starch, 0.2 kg of talc and 0.1 kg of magnesium stearate is pressed in a conventional manner to give tablets in such a way that each tablet contains 10 mg of active compound.

Example F

Dragees

Tablets are pressed analogously to Example E and subsequently coated in a conventional manner with a coating of sucrose, potato starch, talc, tragacanth and dye.

Example G

Capsules 2 kg of active compound of the formula I are introduced into hard gelatine capsules in a conventional manner in such a way that each capsule contains 20 mg of the active compound.

Example H

Ampoules

A solution of 1 kg of active compound of the formula I in 60 l of bidistilled water is sterile filtered, transferred into ampoules, lyophilised under sterile conditions and sealed under sterile conditions. Each ampoule contains 10 mg of active compound.

The invention claimed is:

1. A compound selected from the following compounds:

| No. | Name |
|---|---|
| "A1" | N-Methyl-N-{3-[7-(2-oxo-2,3-dihydro-1H-indol-5-ylamino)-1H-pyrrolo-[2,3-c]pyridin-2-yl]pyridin-2-yl}methanesulfonamide |
| "A2" | N-Methyl-N-{3-[7-(4-morpholin-4-ylphenylamino)-1H-pyrrolo[2,3-c]pyridin-2-yl]pyridin-2-yl}methanesulfonamide |
| "A3" | N-Methyl-N-{3-[7-(2-oxo-1,2,3,4-tetrahydroquinolin-6-ylamino)-1H-pyrrolo[2,3-c]pyridin-2-yl]pyridin-2-yl}-methanesulfonamide |
| "A4" | N-{3-[6-(2-Methoxy-4-morpholin-4-ylphenylamino)-7H-purin-8-yl]pyridin-2-yl}-N-methylmethanesulfonamide |
| "A5" | N-Methyl-N-{3-[6-(4-morpholin-4-ylphenylamino)-7H-purin-8-yl]-pyridin-2-yl}methanesulfonamide |
| "A6" | N-Methyl-N-{3-[6-(1-methyl-1H-pyrazol-4-ylamino)-7H-purin-8-yl]pyridin-2-yl}methanesulfonamide |
| "A7" | N-Methyl-N-{3-[4-(2-oxo-1,2,3,4-tetrahydroquinolin-6-ylamino)-3H-imidazo[4,5-c]pyridin-2-yl]pyridin-2-yl}methanesulfonamide |
| "A9" | N-(3-{[5-Cyano-2-(4-fluorophenyl)-1H-pyrrolo[2,3-b]pyridin-4-yl-amino]methyl}pyridin-2-yl)-N-methylmethanesulfonamide |
| "A10" | N-{3-[(3-Chloro-5-cyano-1H-pyrrolo[2,3-b]pyridin-4-ylamino)-methyl]pyridin-2-yl}-N-methylmethanesulfonamide |
| "A11" | N-{3-[(5-Cyano-2-phenyl-1H-pyrrolo[2,3-b]pyridin-4-ylamino)-methyl]pyridin-2-yl}-N-methylmethanesulfonamide |
| "A12" | N-{3-[(5-Cyano-1H-pyrrolo[2,3-b]pyridin-4-ylamino)methyl]-pyridin-2-yl}-N-methylmethanesulfonamide |
| "A13" | N-Methyl-N-{3-[(5-methyl-1H-pyrrolo[2,3-b]pyridin-4-ylamino)-methyl]pyridin-2-yl}methanesulfonamide |
| "A14" | N-Methyl-N-{3-[(7H-pyrrolo[2,3-d]pyrimidin-4-ylamino)-methyl]-pyridin-2-yl}methanesulfonamide |
| "A15" | N-Methyl-N-{3-[(1H-pyrrolo[2,3-b]pyridin-4-ylamino)methyl]-pyridin-2-yl}methanesulfonamide |
| "A16" | N-Methyl-N-{3-[(6-methyl-7H-pyrrolo[2,3-d]pyrimidin-4-ylamino)-methyl]pyridin-2-yl}methanesulfonamide |
| "A17" | N-{3-[4-(2-Methoxy-4-morpholin-4-ylphenylamino)-3H-imidazo[4,5-c]pyridin-2-yl]pyridin-2-yl}-N-methylmethanesulfonamide |
| "A18" | N-Methyl-N-{3-[6-(2-oxo-2,3-dihydro-1H-indol-5-ylamino)-7H-purin-8-yl]pyridin-2-yl}methanesulfonamide |
| "A19" | N-{3-[(5-Cyano-2-cyclohexyl-1H-pyrrolo[2,3-b]pyridin-4-ylamino)-methyl]pyridin-2-yl}-N-methylmethanesulfonamide |
| "A20" | N-(3-{[2-(4-Butylphenyl)-5-cyano-1H-pyrrolo[2,3-b]pyridin-4-ylamino]methyl}pyridin-2-yl)-N-methylmethanesulfonamide |
| "A21" | N-(3-{[2-(4-Fluorophenyl)-5-trifluoromethyl-1H-pyrrolo[2,3-b]-pyridin-4-ylamino]methyl}pyridin-2-yl)-N-methylmethanesulfonamide |
| "A22" | 2-[[5-Cyano-2-(4-fluorophenyl)-1H-pyrrolo[2,3-b]pyridin-4-yl]amino]-N-methylbenzamide |
| "A23" | N-(3-{[5-Cyano-2-(2-methylpyridin-4-yl)-1H-pyrrolo[2,3-b]-pyridin-4-ylamino]methyl}pyridin-2-yl)-N-methylmethanesulfonamide |
| "A24" | N-(3-{[2-(4-Fluorophenyl)-5-methyl-1H-pyrrolo[2,3-b]pyridin-4-ylamino]methyl}pyridin-2-yl)-N-methylmethanesulfonamide |
| "A25" | N-(3-{[2-(4-Fluorophenyl)-1H-pyrrolo[2,3-b]pyridin-4-ylamino]-methyl}pyridin-2-yl)-N-methylmethanesulfonamide |
| "A26" | (2,5-Difluorobenzyl)-[2-(4-fluorophenyl)-5-trifluoromethyl-1H-pyrrolo-[2,3-b]pyridin-4-yl]amine |
| "A27" | N-{2-[2-(4-Fluorophenyl)-5-trifluoromethyl-1H-pyrrolo[2,3-b]pyridin-4-ylethynyl]phenyl}-N-methylmethanesulfonamide |
| "A28" | N-(2-{2-[2-(4-Fluorophenyl)-5-trifluoromethyl-1H-pyrrolo[2,3-b]-pyridin-4-yl]ethyl}phenyl)-N-methylmethanesulfonamide |
| "A29" | N-(3-{[6-Bromo-2-(4-fluorophenyl)-3H-imidazo[4,5-b]pyridin-7-ylamino]methyl}pyridin-2-yl)-N-methylmethanesulfonamide |
| "A30" | 2-[6-Bromo-2-(4-fluorophenyl)-3H-imidazo[4,5-b]pyridin-7-ylamino]-N-methylbenzamide |
| "A31" | N-(3-{[2-(4-Bromophenyl)-6-trifluoromethyl-3H-imidazo[4,5-b]pyridin-7-ylamino]methyl}pyridin-2-yl)-N-methylmethanesulfonamide |
| "A32" | 2-[2-(4-Fluorophenyl)-5-trifluoromethyl-1H-pyrrolo[2,3-b]pyridin-4-ylamino]-N-methylbenzamide |
| "A33" | N-Methyl-2-[2-(6-morpholin-4-ylpyridin-3-yl)-5-trifluoromethyl-1H-pyrrolo[2,3-b]pyridin-4-ylamino]benzamide |
| "A34" | N-Methyl-2-[2-(4-morpholin-4-ylphenyl)-5-trifluoromethyl-1H-pyrrolo-[2,3-b]pyridin-4-ylamino]benzamide |
| "A35" | N-(3-{[2-(4-Fluorophenyl)-6-trifluoromethyl-3H-imidazo[4,5-b]pyridin-7-ylamino]methyl}pyridin-2-yl)-N-methylmethanesulfonamide |
| "A36" | N-Methyl-2-[2-(6-oxo-1,6-dihydropyridin-3-yl)-5-trifluoromethyl-1H-pyrrolo[2,3-b]pyridin-4-ylamino]benzamide |
| "A37" | 2-[[5-(1,1-Difluoroethyl)-2-(2-methoxy-4-morpholinophenyl)-1H-pyrrolo[2,3-b]pyridin-4-yl]amino]-N-methylbenzamide |
| "A38" | 2-[2-[[5-Cyclopropyl-2-(2-methoxy-4-morpholinophenyl)-1H-pyrrolo-[2,3-b]pyridin-4-yl]amino]phenyl]acetonitrile |
| "A39" | 2-[[5-Cyclopropyl-2-(2-methoxy-4-morpholinophenyl)-1H-pyrrolo[2,3-b]pyridin-4-yl]amino]benzonitrile |
| "A40" | 2-[[5-Cyclopropyl-2-(2-methoxy-4-morpholinophenyl)-1H-pyrrolo[2,3-b]pyridin-4-yl]amino]-N-methylbenzamide |
| "A41" | 7-[[2-(2-Methoxy-4-morpholinophenyl)-5-(trifluoromethyl)-1H-pyrrolo[2,3-b]pyridin-4-yl]amino]-2-methylisoindolin-1-one |
| "A42" | 7-[[2-(2-Methoxy-4-morpholinophenyl)-5-(trifluoromethyl)-1H-pyrrolo[2,3-b]pyridin-4-yl]oxy]-2-methylisoindolin-1-one |
| "A43" | 2-[[2-(2-Methoxy-5-morpholinophenyl)-5-(trifluoromethyl)-1H-pyrrolo[2,3-b]pyridin-4-yl]amino]-N-methylbenzamide |
| "A44" | 2-[5-Methoxy-2-(2-methoxy-4-morpholinophenyl)-1H-pyrrolo[2,3-b]-pyridin-4-yl]amino]-N-methylbenzamide |
| "A45" | 2-[[2-(2-Methoxy-4-morpholinophenyl)-5-(trifluoromethoxy)-1H-pyrrolo[2,3-b]pyridin-4-yl]amino]-N-methylbenzamide |
| "A46" | 2-[[2-(2-Methoxy-4-morpholinophenyl)-5-(trifluoromethyl)-1H-pyrrolo[2,3-b]pyridin-4-yl]amino]-N-methylbenzamide |
| "A47" | N-Methyl-N-[3-[[[2-(6-oxo-1H-pyridin-3-yl)-5-(trifluoromethyl)-1H-pyrrolo[2,3-b]pyridin-4-yl]amino]methyl]-2-pyridyl]methanesulfonamide |
| "A48" | N-[3-[[[2-(2-Methoxyphenyl)-5-(trifluoromethyl)-1H-pyrrolo[2,3-b]-pyridin-4-yl]amino]methyl]-2-pyridyl]-N-methylmethanesulfonamide |
| "A49" | N-[3-[[[2-(2-Methoxyphenyl)-5-(trifluoromethyl)-1H-pyrrolo[2,3-b]-pyridin-4-yl]amino]methyl]-2-pyridyl]-N-methylmethanesulfonamide |
| "A50" | N-Methyl-N-[3-[[[2-(6-morpholino-3-pyridyl)-5-(trifluoromethyl)-1H-pyrrolo[2,3-b]pyridin-4-yl]amino]methyl]-2-pyridyl]-methanesulfonamide |
| "A51" | N-[3-[[[5-Cyano-2-(6-oxo-1H-pyridin-3-yl)-1H-pyrrolo[2,3-b]pyridin-4-yl]amino]methyl]-2-pyridyl]-N-methylmethanesulfonamide |
| "A52" | N-[3-[[[2-(2-Methoxy-4-morpholinophenyl)-5-(trifluoromethyl)-1H-pyrrolo[2,3-b]pyridin-4-yl]amino]methyl]-2-pyridyl]-N-methylmethanesulfonamide |
| "A53" | N-[3-[[[5-Cyano-2-(2-methoxy-4-morpholinophenyl)-1H-pyrrolo[2,3-b]pyridin-4-yl]amino]methyl]-2-pyridyl]-N-methylmethanesulfonamide |
| "A54" | N-[3-[[[5-Cyano-2-[5-(3-pyridyl)-1,3,4-oxadiazol-2-yl]-1H-pyrrolo[2,3-b]pyridin-4-yl]amino]methyl]-2-pyridyl]-N-methylmethanesulfonamide |
| "A55" | N-[3-[[[5-Cyano-2-(5-methyl-1,3,4-oxadiazol-2-yl)-1H-pyrrolo[2,3-b]-pyridin-4-yl]amino]methyl]-2-pyridyl]-N-methylmethanesulfonamide |
| "A56" | N-[3-[[[2-(4-Fluorophenyl)-5-(trifluoromethyl)-1H-pyrrolo[2,3-b]-pyridin-4-yl]amino]methyl]-4-methyl-2-pyridyl]-N-methylmethanesulfonamide |
| "A57" | N-[3-[[[5-Cyano-2-(4-fluorophenyl)-1H-pyrrolo[2,3-b]pyridin-4-yl]-amino]methyl]-4-methyl-2-pyridyl]-N-methylmethanesulfonamide |
| "A58" | 2-[[5-Cyano-2-(4-fluorophenyl)-1H-pyrrolo[2,3-b]pyridin-4-yl]amino]-N,3-dimethylbenzamide |
| "A59" | 2-[[2-(4-Fluorophenyl)-5-(trifluoromethyl)-1H-pyrrolo[2,3-b]pyridin-4-yl]amino]-N,3-dimethylbenzamide |
| "A60" | 1,1,1-Trifluoro-N-[3-[[[2-(4-fluorophenyl)-5-(trifluoromethyl)-1H-pyrrolo[2,3-b]pyridin-4-yl]amino]methyl]-2-pyridyl]-N-methylmethanesulfonamide |
| "A61" | (1S)-2-[[5-Cyano-2-(4-fluorophenyl)-1H-pyrrolo[2,3-b]pyridin-4-yl]-amino]-N-methylcyclohexanecarboxamide |
| "A62" | N-[(1S)-2-[[5-Cyano-2-(4-fluorophenyl)-1H-pyrrolo[2,3-b]pyridin-4-yl]amino]cyclohexyl]-N-methylmethanesulfonamide |
| "A63" | 1-[[5-Cyano-2-(4-fluorophenyl)-1H-pyrrolo[2,3-b]pyridin-4-yl]amino]-N-methylcyclopropanecarboxamide |
| "A64" | 1-[[2-(4-Fluorophenyl)-5-(trifluoromethyl)-1H-pyrrolo[2,3-b]pyridin-4-yl]amino]-N-methylcyclopropanecarboxamide |
| "A65" | N-[3-[[[5-(1,1-Difluoroethyl)-2-(4-fluorophenyl)-1H-pyrrolo[2,3-b]-pyridin-4-yl]amino]methyl]-2-pyridyl]-N-methylmethanesulfonamide |
| "A66" | N-[3-[[[5-(1,1-Difluoroethyl)-2-(4-fluorophenyl)-1H-pyrrolo[2,3-b]-pyridin-4-yl]amino]methyl]-2-pyridyl]-1,1,1-trifluoro-N-methyl-methanesulfonamide |

| No. | Name |
|---|---|
| "A67" | N-(2-Aminoethyl)-3-[5-cyano-4-[[2-[methyl(methylsulfonyl)-amino]-3-pyridyl]methylamino]-1H-pyrrolo[2,3-b]pyridin-2-yl]benzamide |
| "A68" | 3-[5-Cyano-4-[[2-[methyl(methylsulfonyl)amino]-3-pyridyl]-methyl-amino]-1H-pyrrolo[2,3-b]pyridin-2-yl]-N-methylbenzamide |
| "A69" | 3-[5-Cyano-4-[[2-[methyl(methylsulfonyl)amino]-3-pyridyl]-methyl-amino]-1H-pyrrolo[2,3-b]pyridin-2-yl]-N-(1-methyl-4-piperidyl)-benzamide |
| "A70" | 4-[5-Cyano-4-[[2-[methyl(methylsulfonyl)amino]-3-pyridyl]-methyl-amino]-1H-pyrrolo[2,3-b]pyridin-2-yl]-N-(1-methyl-4-piperidyl)-benzamide |
| "A71" | N-[3-[[[2-[(2S)-4-(2-Aminoethyl)-2-methylpiperidine-1-carbonyl]-5-cyano-1H-pyrrolo[2,3-b]pyridin-4-yl]amino]-methyl]-2-pyridyl]-N-methylmethanesulfonamide |
| "A72" | N-[3-[[[2-(4-Aminopiperidine-1-carbonyl)-5-cyano-1H-pyrrolo[2,3-b]-pyridin-4-yl]amino]methyl]-2-pyridyl]-N-methylmethanesulfonamide |
| "A73" | N-[3-[[[5-Cyano-2-[3-(dimethylamino)pyrrolidine-1-carbonyl]-1H-pyrrolo[2,3-b]pyridin-4-yl]amino]methyl]-2-pyridyl]-N-methylmethane-sulfonamide |
| "A74" | 5-Cyano-N-(2-dimethylaminoethyl)-4-[[2-[methyl(methyl-sulfonyl)-amino]-3-pyridyl]methylamino]-1H-pyrrolo[2,3-b]pyridine-2-carboxamide |
| "A75" | N-[3-[[[5-Cyano-2-(morpholine-4-carbonyl)-1H-pyrrolo[2,3-b]pyridin-4-yl]amino]methyl]-2-pyridyl]-N-methylmethanesulfonamide |
| "A76" | N-[3-[[[5-Cyano-2-(4-fluorophenyl)-1H-pyrrolo[2,3-b]pyridin-4-yl]-amino]methyl]-2-pyridyl]-1,1,1-trifluoro-N-methylmethane-sulfonamide |
| "A77" | N-[3-[[[5-(1,1-Difluoroethyl)-2-(4-fluorophenyl)-1H-pyrrolo[2,3-b]-pyridin-4-yl]amino]methyl]-2-pyridyl]-N-methylmethanesulfonamide |
| "A78" | N-[3-[[[5-Cyano-2-(2-oxoindan-5-yl)-1H-pyrrolo[2,3-b]pyridin-4-yl]amino]methyl]-2-pyridyl]-N-methylmethanesulfonamide |
| "A79" | N-[3-[[[5-Cyano-2-(6-oxo-1H-pyriclazin-3-yl)-1H-pyrrolo[2,3-b]pyridin-4-yl]amino]methyl]-2-pyridyl]-N-methylmethanesulfonamide |
| "A80" | N-[3-[[(5-Cyano-2-pyridazin-3-yl-1H-pyrrolo[2,3-b]pyridin-4-yl)-amino]methyl]-2-pyridyl]-N-methylmethanesulfonamide |
| "A81" | N-[3-[[(5-Cyano-2-pyridazin-4-yl-1H-pyrrolo[2,3-b]pyridin-4-yl)-amino]methyl]-2-pyridyl]-N-methylmethanesulfonamide |
| "A82" | N-[3-[[(5-Cyano-2-pyrimidin-4-yl-1H-pyrrolo[2,3-b]pyridin-4-yl)-amino]methyl]-2-pyridyl]-N-methylmethanesulfonamide |
| "A83" | N-[3-[[[5-Cyano-2-(6-oxo-5,7-dihydrocyclopenta[b]pyridin-3-yl)-1H-pyrrolo[2,3-b]pyridin-4-yl]amino]methyl]-2-pyridyl]-N-methyl-methanesulfonamide |
| "A84" | N-[3-[[[5-Cyano-2-(2-oxoindolin-6-yl)-1H-pyrrolo[2,3-b]pyridin-4-yl]-amino]methyl]-2-pyridyl]-N-methylmethanesulfonamide |
| "A85" | N-[3-[[[5-Cyano-2-(2-oxoindolin-5-yl)-1H-pyrrolo[2,3-b]pyridin-4-yl]amino]methyl]-2-pyridyl]-N-methylmethanesulfonamide |
| "A86" | N-[3-[[(5-Cyano-2-isoxazol-4-yl-1H-pyrrolo[2,3-b]pyridin-4-yl)amino]-methyl]-2-pyridyl]-N-methylmethanesulfonamide |
| "A87" | N-[3-[[[5-Cyano-2-(1-methylpyrazol-4-yl)-1H-pyrrolo[2,3-b]pyridin-4-yl]amino]methyl]-2-pyridyl]-N-methylmethanesulfonamide |
| "A88" | 2-(3-Methoxyphenyl)-4-(1-methyl-1H-pyrazol-4-yl)-5-trifluoromethyl-1H-pyrrolo[2,3-b]pyridine |
| "A89" | 2-[2-(2-Methoxy-4-morpholin-4-ylphenyl)-5-trifluoromethyl-1H-pyrrolo[2,3-b]pyridin-4-ylamino]benzonitrile |
| "A90" | 4-[4-(3-Morpholin-4-ylphenyl)-5-trifluoromethyl-1H-pyrrolo[2,3-b]-pyridin-2-yl]benzamide |
| "A91" | 4-(4-Fluorophenyl)-2-piperidin-4-yl-5-trifluoromethyl-1H-pyrrolo[2,3-b]pyridine |
| "A92" | (3,5-Difluorobenzyl)-[2-(4-morpholin-4-ylphenyl)-5-trifluoromethyl-1H-pyrrolo[2,3-b]pyridin-4-yl]amine |
| "A93" | 2-[2-(4-Fluorophenyl)-5-trifluoromethyl-1H-pyrrolo[2,3-b]pyridin-4-yloxy]benzonitrile |
| "A94" | 7-[2-(4-Fluorophenyl)-5-trifluoromethyl-1H-pyrrolo[2,3-b]pyridin-4-yl-amino]-2-methyl-2,3-dihydroisoindol-1-one |
| "A95" | {3-[4-(1-Methyl-1H-pyrazol-4-yl)-5-trifluoromethyl-1H-pyrrolo[2,3-b]-pyridin-2-yl]phenyl}morpholin-4-ylmethano |
| "A96" | {4-[4-(1-Methyl-1H-pyrazol-4-yl)-5-trifluoromethyl-1H-pyrrolo[2,3-b]-pyridin-2-yl]phenyl}morpholin-4-ylmethanone |
| "A97" | 5-[2-(4-Morpholin-4-ylphenyl)-5-trifluoromethyl-1H-pyrrolo[2,3-b]-pyridin-4-yl]-1H-pyridin-2-one |
| "A98" | 5-[2-(3-Morpholin-4-ylphenyl)-5-trifluoromethyl-1H-pyrrolo[2,3-b]-pyridin-4-yl]-1H-pyridin-2-one |
| "A99" | 2-(4-Fluorophenyl)-5-trifluoromethyl-6-(1,3,5-trimethyl-1H-pyrazol-4-yl)-1H-pyrrolo[2,3-b]pyridine |
| "A100" | 4-[2-(4-Morpholin-4-ylphenyl)-5-trifluoromethyl-1H-pyrrolo[2,3-b]-pyridin-4-yl]phenylamine |
| "A101" | Methyl 3-[4-(1-methyl-1H-pyrazol-4-yl)-5-trifluoromethyl-1H-pyrrolo-[2,3-b]pyridin-2-yl]benzoate |
| "A102" | 2-(4-Morpholin-4-ylphenyl)-4-(1H-pyrazol-4-yl)-5-trifluoromethyl-1H-pyrrolo[2,3-b]pyridine |
| "A103" | 4-(1-Methyl-1H-pyrazol-4-yl)-2-(4-morpholin-4-ylphenyl)-5-trifluoro-methyl-1H-pyrrolo[2,3-b]pyridine |
| "A104" | 4-(1-Methyl-1H-pyrazol-4-yl)-2-(3-morpholin-4-ylphenyl)-5-trifluoro-methyl-1H-pyrrolo[2,3-b]pyridine |
| "A105" | 2-(4-Fluorophenyl)-4-(1-methyl-1H-pyrazol-4-yl)-5-trifluoromethyl-1H-pyrrolo[2,3-b]pyridine |
| "A106" | 2-(4-Fluorophenyl)-4-(1H-pyrazol-4-yl)-5-trifluoromethyl-1H-pyrrolo-[2,3-b]pyridine |
| "A107" | 2-(3-Morpholin-4-ylphenyl)-4-(1H-pyrazol-4-yl)-5-trifluoromethyl-1H-pyrrolo[2,3-b]pyridine |
| "A108" | 2-(4-Fluorophenyl)-6-(1-methyl-1H-pyrazol-4-yl)-5-trifluoromethyl-1H-pyrrolo[2,3-b]pyridine |
| "A109" | 2-(4-Fluorophenyl)-6-(1H-pyrazol-4-yl)-5-trifluoromethyl-1H-pyrrolo-[2,3-b]pyridine |
| "A110" | 5-[2-(4-Fluorophenyl)-5-trifluoromethyl-1H-pyrrolo[2,3-b]pyridin-4-yl]-1H-pyridin-2-one | or a pharmaceutically usable salt, tautomer or stereoisomer thereof, or a mixture, in any ratio, of any of: the compound, a pharmaceutically usable salt thereof, a tautomer thereof and/or a stereoisomer thereof.

2. A medicament composition comprising at least one compound of claim 1 or a pharmaceutically usable salt, tautomer or stereoisomer thereof, or a mixture, in any ratio, of any of: the compound, a pharmaceutically usable salt thereof, a tautomer thereof and/or a stereoisomer thereof, and optionally excipients and/or adjuvants.

3. A compound according to claim 1, which is one of the compounds from A1-A7, A9-A14, A21-A25, A30-A33, A95-A97, A100-A102 or A104-A105, or a pharmaceutically usable salt, tautomer or stereoisomer thereof, or a mixture, in any ratio, of any of: the compound, a pharmaceutically usable salt thereof, a tautomer thereof and/or a stereoisomer thereof.

\* \* \* \* \*